(12) United States Patent
Tagliatela et al.

(10) Patent No.: US 10,519,465 B2
(45) Date of Patent: *Dec. 31, 2019

(54) TISSUE SELECTIVE TRANSGENE EXPRESSION

(71) Applicant: Encoded Therapeutics, Inc., South San Francisco, CA (US)

(72) Inventors: Stephanie Tagliatela, South San Francisco, CA (US); Andrew Young, South San Francisco, CA (US); Szu-Ying Chen, South San Francisco, CA (US); Kartik Ramamoorthi, South San Francisco, CA (US); David Oberkofler, South San Francisco, CA (US)

(73) Assignee: Encoded Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,433

(22) Filed: Oct. 5, 2018

(65) Prior Publication Data

US 2019/0024120 A1 Jan. 24, 2019

Related U.S. Application Data

(63) Continuation of application No. PCT/US2018/025940, filed on Apr. 3, 2018.

(60) Provisional application No. 62/480,998, filed on Apr. 3, 2017.

(51) Int. Cl.
| | |
|---|---|
| *C12N 15/113* | (2010.01) |
| *C12N 15/86* | (2006.01) |
| *A61K 48/00* | (2006.01) |
| *C12N 15/864* | (2006.01) |
| *C12N 15/85* | (2006.01) |

(52) U.S. Cl.
CPC .......... *C12N 15/85* (2013.01); *A61K 48/0058* (2013.01); *C12N 15/113* (2013.01); *C12N 15/86* (2013.01); *C12N 15/8645* (2013.01); *A61K 48/00* (2013.01); *C12N 2320/32* (2013.01); *C12N 2750/14143* (2013.01); *C12N 2830/008* (2013.01)

(58) Field of Classification Search
CPC ...... C12N 15/85; C12N 15/113; C12N 15/86; C12N 15/8645; C12N 2830/008; C12N 2750/14143; C12N 2320/32; A61K 48/0058; A61K 48/00
USPC .............................. 435/320.1; 536/24.1, 23.2
See application file for complete search history.

(56) References Cited

U.S. PATENT DOCUMENTS

| | | |
|---|---|---|
| 6,180,613 B1 | 1/2001 | Kaplitt et al. |
| 6,303,370 B1 | 10/2001 | Kappen et al. |
| 6,372,500 B1 | 4/2002 | Hu et al. |
| 6,436,708 B1 | 8/2002 | Leone et al. |
| 6,479,626 B1 | 11/2002 | Kim et al. |
| 6,503,888 B1 | 1/2003 | Kaplitt et al. |
| 6,524,851 B1 | 2/2003 | Ellis |
| 6,649,371 B1 | 11/2003 | Jentsch |
| 6,933,113 B2 | 8/2005 | Case et al. |
| 6,994,993 B2 | 2/2006 | Qin et al. |
| 6,998,118 B2 | 2/2006 | Kaspar et al. |
| 7,094,600 B2 | 8/2006 | Wang |
| 7,101,540 B2 | 9/2006 | Kaspar et al. |
| 7,125,676 B2 | 10/2006 | George et al. |
| 7,157,571 B2 | 1/2007 | Wang et al. |
| 7,220,719 B2 | 5/2007 | Case et al. |
| 7,361,635 B2 | 4/2008 | Miller et al. |
| 7,595,376 B2 | 9/2009 | Kim et al. |
| 7,655,460 B2 | 2/2010 | Rouleau et al. |
| 7,943,553 B2 | 5/2011 | Case et al. |
| 8,143,005 B2 | 3/2012 | Rouleau et al. |
| 8,772,453 B2 | 7/2014 | Paschon et al. |
| 8,927,514 B2 | 1/2015 | Chatterjee et al. |
| 8,969,077 B2 | 3/2015 | Head et al. |
| 9,102,949 B2 | 8/2015 | Gao et al. |
| 9,267,151 B2 | 2/2016 | Guerrero et al. |
| 9,315,825 B2 | 4/2016 | Wilson et al. |
| 9,624,498 B2 | 4/2017 | Froelich et al. |
| 9,845,481 B2 | 12/2017 | Marengo et al. |
| 2004/0096885 A1 | 5/2004 | Rouleau et al. |
| 2004/0191791 A1 | 9/2004 | Wallace et al. |
| 2004/0258666 A1 | 12/2004 | Passini et al. |
| 2005/0032219 A1 | 2/2005 | Aubourg et al. |
| 2007/0161031 A1 | 7/2007 | Trinklein et al. |

(Continued)

FOREIGN PATENT DOCUMENTS

| | | |
|---|---|---|
| EP | 1590467 B1 | 10/2009 |
| EP | 1747277 B1 | 8/2011 |

(Continued)

OTHER PUBLICATIONS

Narlikar et al. (2009) Briefings in Functional Genomics and Proteomics, vol. 8(4) 214-230.*

(Continued)

*Primary Examiner* — Anne Marie S Wehbe
(74) *Attorney, Agent, or Firm* — Wilson Sonsini Goodrich & Rosati

(57) ABSTRACT

Provided herein are compositions and methods for selective expression of a transgene. Compositions and methods for selective expression of a transgene comprise one or more human regulatory elements, which, when operably linked to a transgene, can facilitate selective expression of a transgene (e.g., cell-type selective expression) in a target cell as compared to at least one or more non-target cells.

13 Claims, 14 Drawing Sheets

Specification includes a Sequence Listing.

(56) References Cited

U.S. PATENT DOCUMENTS

| | | |
|---|---|---|
| 2009/0018031 A1 | 1/2009 | Trinklein et al. |
| 2009/0311222 A1 | 12/2009 | Baraban et al. |
| 2010/0130594 A1 | 5/2010 | Barkats |
| 2011/0065100 A1 | 3/2011 | Aldred et al. |
| 2011/0135611 A1 | 6/2011 | Huang et al. |
| 2011/0165129 A1 | 7/2011 | Kriegstein et al. |
| 2011/0268747 A1 | 11/2011 | Guerrero et al. |
| 2013/0096183 A1 | 4/2013 | Collard et al. |
| 2013/0224836 A1 | 8/2013 | Muramatsu |
| 2013/0254909 A1 | 9/2013 | Marengo et al. |
| 2014/0037585 A1 | 2/2014 | Wright et al. |
| 2014/0142160 A1 | 5/2014 | Lee et al. |
| 2015/0044187 A1 | 2/2015 | Visel et al. |
| 2015/0111955 A1 | 4/2015 | High et al. |
| 2015/0253339 A1 | 9/2015 | Shekdar |
| 2015/0353917 A1 | 12/2015 | Miller et al. |
| 2016/0032319 A1 | 2/2016 | Wright et al. |
| 2016/0120960 A1 | 5/2016 | McIvor et al. |

FOREIGN PATENT DOCUMENTS

| | | |
|---|---|---|
| EP | 3119878 A2 | 1/2017 |
| WO | WO-2010037143 A1 | 4/2010 |
| WO | WO-2016172155 A1 | 10/2016 |
| WO | WO-2016188112 A1 | 12/2016 |
| WO | WO-2017075335 A1 | 5/2017 |
| WO | WO-2017075338 A2 | 5/2017 |
| WO | WO-2018187363 A1 | 10/2018 |

OTHER PUBLICATIONS

Khan et al. (2013) Genesis, vol. 51(5), 311-324.*
Altschul, et al. Basic local alignment search tool. J Mol Biol. Oct. 5, 1990;215(3):403-10.
Altschul, et al. Gapped BLAST and PSI-BLAST: a new generation of protein database search programs. Nucleic Acids Res. Sep. 1, 1997;25(17):3389-402.
Bagot et al., Epigenetic signaling in psychiatric disorders: stress and depression, Dialogues Clin Neurosci., 16(3): 281-295 (2014).
Bezzina et al., Early Onset of Hypersynchronous Network Activity and Expression of a Marker of Chronic Seizures in the Tg2576 Mouse Model of Alzheimer's Disease, PLoS ONE 10(3): e0119910 (14 pages) (2015).
Challis et al., Raphe GABAergic Neurons Mediate the Acquisition of Avoidance after Social Defeat, The Journal of Neuroscience, 33(35):13978-13988 (2013).
Cheah et al., Specific deletion of Nav1.1 sodium channels in inhibitory interneurons causes seizures and premature death in a mouse model of Dravet syndrome, Proc Natl Acad Sci, 109(36): 14646-14651 (2012).
Connelly. Dravet Syndrome: Diagnosis and Long-Term Course. Can J Neurol Sci. 43: S3-S8 (2016).
Co-pending U.S. Appl. No. 16/153,401, filed Oct. 5, 2018.
Co-pending U.S. Appl. No. 16/153,420, filed Oct. 5, 2018.
Co-pending U.S. Appl. No. 16/153,443, filed Oct. 5, 2018.
CRISPR-Cas9 Epigenome Editing Screen Reveals Regulatory Elements. GenomeWeb. 3 pages. Apr. 3, 2017. Retrieved Nov. 6, 2018 at URL: https://www.genomeweb.com/epigenetics-research/crispr-cas9-epigenome-editing-screen-reveals-regulatory-elements?utm_source=Sailthru&utm_medium=email&utm_campaign=GWDN%20Tues%20AM%202017-04-04&utm_term=GW%20Daily%20News%20Bulletin#.W6XHxntKgdU>.
Dimidschstein et al. A viral strategy for targeting and manipulating interneurons across vertebrate species. Nat Neurosci. 19(12): 1743-1749 (Dec. 2016). doi:10.1038/nn.4430.
Frye et al., Neuropathological Mechanisms of Seizures in Autism Spectrum Disorder, Frontiers in Neuroscience, 10:192 (9 pages) (2016).
Gray et al., Optimizing Promoters for Recombinant Adeno-Associated Virus-Mediated Gene Expression in the Peripheral and Central Nervous System Using Self-Complementary Vectors, Human Gene Therapy, 22:1143-1153 (2011).
Han et al., Autistic behavior in Scn1a+/− mice and rescue by enhanced GABAergic transmission, Nature, 489(7416): 385-390 (2012).
Han et al., Enhancement of Inhibitory Neurotransmission by GABAA Receptors Having α2,3-Subunits Ameliorates Behavioral Deficits in a Mouse Model of Autism, Neuron, 81(6): 1282-1289 (2014).
Hawkins et al. The synthetic neuroactive steroid SGE-516 reduces seizure burden and improves survival in a Dravet syndrome mouse model. Scientific Reports 7:15327. Published online Nov. 10, 2017. 8 pages. DOI:10.1038/s41598-017-15609-w.
Hedrich et al., Impaired Action Potential Initiation in GABAergic Interneurons Causes Hyperexcitable Networks in an Epileptic Mouse Model Carrying a Human Nav1.1 Mutation, The Journal of Neuroscience, 34(45): 14874-14889 (2014).
Irizarry et al., Incidence of New-Onset Seizures in Mild to Moderate Alzheimer Disease, Arch Neurol., 69(3): 368-372 (2012).
Karlin, et al. Applications and statistics for multiple high-scoring segments in molecular sequences. Proc Natl Acad Sci U S A. Jun. 15, 1993;90(12):5873-7.
Karlin, et al. Methods for assessing the statistical significance of molecular sequence features by using general scoring schemes. Proc Natl Acad Sci U S A. Mar. 1990;87(6):2264-8.
Kovacs et al., Alzheimer's secretases regulate voltage-gated sodium channels, Neurosci Lett., 486(2): 68-72 (2010).
Ledri et al. Global Optogenetic Activation of Inhibitory Interneurons during Epileptiform Activity. Journal of Neuroscience 34(9):3364-3377 (Feb. 26, 2014). DOI: https://doi.org/10.1523/JNEUROSCI.2734-13.2014.
Lee et al. The Largest Group of Superficial Neocortical GABAergic Interneurons Expresses Ionotropic Serotonin Receptors. Journal of Neuroscience 30(50):16796-16808 (Dec. 15, 2010). DOI: https://doi.org/10.1523/JNEUROSCI.1869-10.2010.
Maguire et al. Gene Therapy for the Nervous System: Challenges and New Strategies. Neurotherapeutics 11:817-839 (Aug. 27, 2014). DOI: 10.1007/s13311-014-0299-5.
Marini et al. The genetics of Dravet syndrome. Epilepsia 52(Suppl. 2):24-29 (2011).
McLean et al., Widespread neuron-specific transgene expression in brain and spinalcord following synapsin promoter-driven AAV9 neonatalintracerebroventricular injection, Neuroscience Letters, 576: 73-78 (2014).
Meyer et al. In vivo labeling of parvalbumin-positive interneurons and analysis of electrical coupling in identified neurons. J Neurosci 22(16):7055-7064 (Aug. 15, 2002).
Miller et al. Mapping genetic modifiers of survival in a mouse model of Dravet syndrome. Genes, Brain and Behavior 13:163-172 (Feb. 2014). First published Oct. 23, 2013. doi: 10.1111/gbb.12099.
Mo et al. Epigenomic Signatures of Neuronal Diversity in the Mammalian Brain. Neuron 86:1369-1384 (Jun. 17, 2015).
Mo et al. Supplemental Information: Epigenomic Signatures of Neuronal Diversity in the Mammalian Brain. Neuron 86(6) (Jun. 17, 2015). 30 pages.
Nathanson et al., Short promoters in viral vectors drive selective expression in mammalian inhibitory neurons, but do not restrict activity to specifi c inhibitory cell-types, Frontiers in Neural Circuits, 3(19): 1-24 (2009).
Ogiwara et al., Nav1.1 haploinsufficiency in excitatory neurons ameliorates seizure-associated sudden death in a mouse model of Dravet syndrome, Human Molecular Genetics, 22(23): 4784-4804 (2013).
Ogiwara et al. Nav1.1 Localizes to Axons of Parvalbumin-Positive Inhibitory Interneurons: A Circuit Basis for Epileptic Seizures in Mice Carrying an Scn1a Gene Mutation. The Journal of Neuroscience 27(22):5903-5914 (May 30, 2007).
Palop et al., Aberrant Excitatory Neuronal Activity and CompensatoryRemodelingof InhibitoryHippocampal Circuits in MouseModels of Alzheimer's Disease, Neuron, 55: 697-711 (2007).
Palop et al., Epilepsy and Cognitive Impairments in Alzheimer Disease, Arch Neurol., 66(4): 435 (11 pages) (2009).
PCT/US2018/025940 International Search Report and Written Opinion dated Aug. 23, 2018.

(56) References Cited

OTHER PUBLICATIONS

Pelkey et al. Hippocampal GABAergic Inhibitory Interneurons. Physiol Rev 97(4):1619-1747 (Oct. 1, 2017). DOI: 10.1152/physrev.00007.2017.
Puts et al., Reduced GABA and Altered Somatosensory Function in Children with Autism Spectrum Disorder, Autism Res., 10(4): 608-619 (2017).
Pvalb (main page). The Human Protein Atlas. Available at https://www.proteinatlas.org/ENSG00000100362-PVALB/tissue. Accessed on Sep. 27, 2018.
Radde et al. Aβ42-driven cerebral amyloidosis in transgenic mice reveals early and robust pathology. EMBO reports 7(9):940-946 (Sep. 1, 2006). Published online Aug. 11, 2006. DOI 10.1038/sj.embor.7400784.
Ritter et al., Lentiviral expression of GAD67 and CCK promoterdriven opsins to target interneurons in vitro and in vivo, J Gene Med,18: 27-37 (2016).
Shevtsova et al., Promoters and serotypes: targeting of adeno-associated virus vectors for gene transfer in the rat central nervous system in vitro and in vivo, Exp Physiol 90.1 pp. 53-59 (2004).
Sohn et al., A Single Vector Platform for High-Level Gene Transduction of Central Neurons: Adeno-Associated Virus Vector Equipped with the Tet-Off System, PLoS ONE 12(1): e0169611, 22 pages, (2017).
Soukupova et al., Impairment of GABA release in the hippocampus at the time of the first spontaneous seizure in the pilocarpine model of temporal lobe epilepsy, Experimental Neurology, 257: 39-49 (2014).
Sun et al., SCN1A, SCN1B, and GABRG2 gene mutation analysis in Chinese families with generalized epilepsy with febrile seizures plus, J Hum Genet, 53:769-774 (2008).
Tai et al., Impaired excitability of somatostatin- and parvalbumin-expressing cortical interneurons in a mouse model of Dravet Syndrome, Proc Natl Acad Sci, 111(30): E3139-3148 (2014).
Tamamaki et al. Green flourescent protein expression and colocalization with calretinin, parvalbumin, and somatostatin in the GAD67-GFP knock-in mouse. J Comp Neurol 467(1):60-79 (Dec. 1, 2003).
Taniguchi et al., A Resource of Cre Driver Lines for Genetic Targeting of GABAergic Neurons in Cerebral Cortex, Neuron, 71: 995-1013 (2011).
Taniguchi, Genetic dissection of GABAergic neural circuits in mouse neocortex. Front Cell Neurosci vol. 8, Article 8 (Jan. 27, 2014). 22 pages. DOI: .https://doi.org/10.3389/fncel.2014.00008.
Van Den Pol et al. Selective neuronal expression of green fluorescent protein with cytomegalovirus promoter reveals entire neuronal arbor in transgenic mice. J Neurosci 18(24):10640-10651 (Dec. 15, 1998).
Verret et al., Inhibitory Interneuron Deficit Links Altered Network Activity and Cognitive Dysfunction in Alzheimer Model, Cell, 149(3): 708-721 (2012).
Wootton, et al. Statistics of local complexity in amino acid sequences and sequence databases. Computers & Chemistry. vol. 17, Issue 2, Jun. 1993, pp. 149-163.
Xie et al., MicroRNA-regulated, Systemically Delivered rAAV9: A Step Closer to CNS-restricted Transgene Expression, Mol Ther., 19(3):526-535 (2011).
Xu et al. Immunochemical characterization of inhibitory mouse cortical neurons: Three chemically distinct classes of inhibitory cells. J Comp Neurol 518(3):389-404 (Feb. 1, 2010). doi: 10.1002/cne.22229.
Yan et al., Targeting the β secretase BACE1 for Alzheimer's disease therapy, Lancet Neurol., 13(3): 319-329 (2014).
Reetz et al, Development of Adenoviral Delivery Systems to Target Hepatic Stellate Cells In Vivo, PLoS ONE 8(6): e67091, 14 pages (2013).
Zuris et al., Efficient Delivery of Genome-Editing Proteins In Vitro and In Vivo, Nat Biotechnol., 33(1): 73-80 (Jan. 2015).
U.S. Appl. No. 16/153,443 Office Action dated Jul. 29, 2019.
Genbank Accession No. AC007405. *Homo sapiens* BAC clone RP11-570C16 from 2, complete sequence. Washington University Genome Sequencing Center. Priority to at least Apr. 30, 2005.
Genome Reference Consortium Accession No. AL589692. Mouse DNA sequence from clone RP23-385C1 on chromosome 15, complete sequence. Wellcome Trust Sanger Institute. Submitted Dec. 13, 2012.
Schleef et al. The structure of the mouse parvalbumin gene. Mammalian Genome 3:217-225 (1992).
U.S. Appl. No. 16/153,401 Notice of Allowance dated Feb. 21, 2019.
U.S. Appl. No. 16/153,401 Office Action dated Jan. 11, 2019.
U.S. Appl. No. 16/153,420 Notice of Allowance dated Feb. 21, 2019.
U.S. Appl. No. 16/153,420 Office Action dated Dec. 14, 2018.
U.S. Appl. No. 16/153,443 Office Action dated Jan. 11, 2019.

* cited by examiner

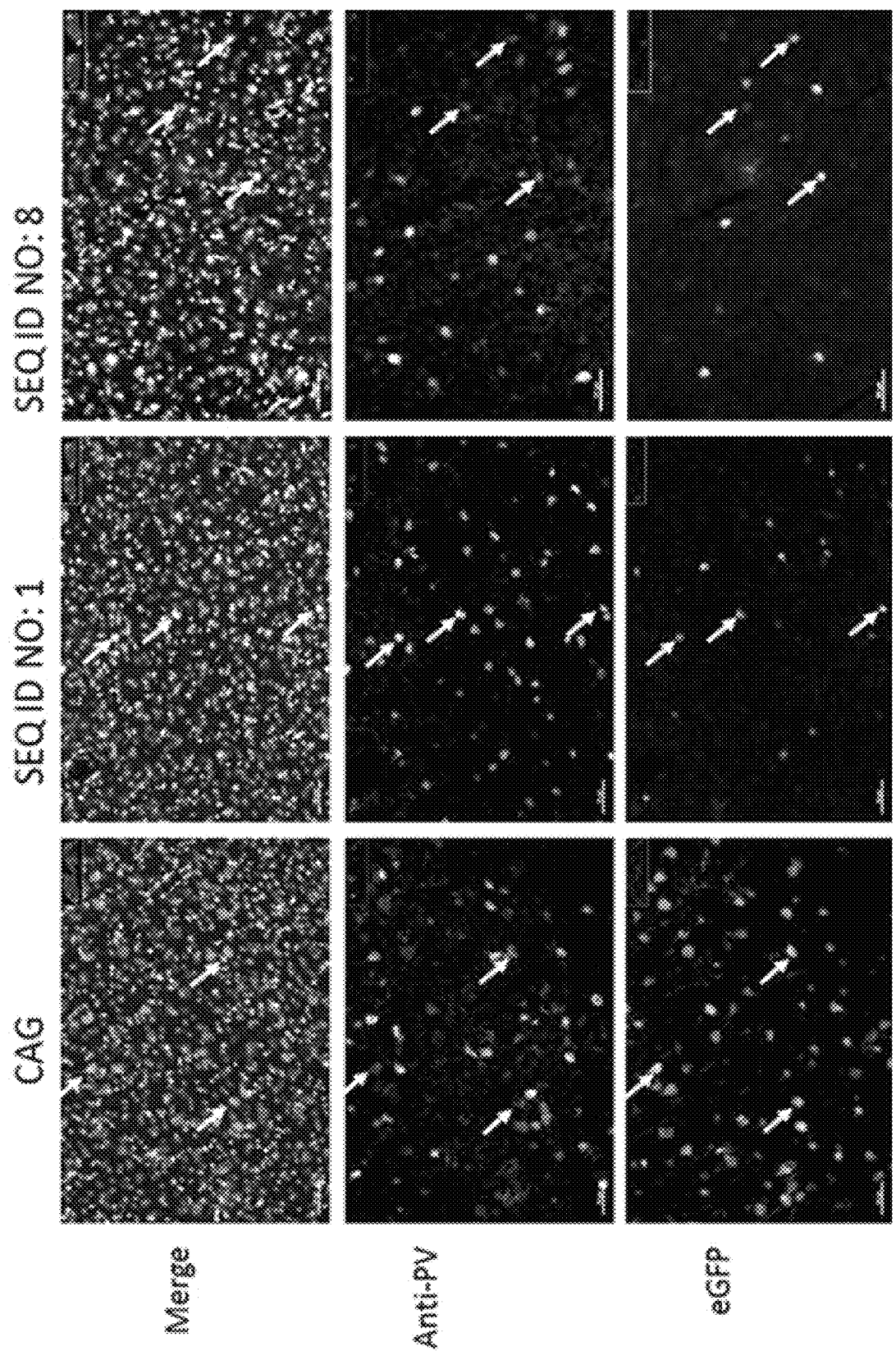

TISSUE SELECTIVE TRANSGENE EXPRESSION

CROSS-REFERENCE

This application is a continuation application of International Application No. PCT/US2018/025940, filed Apr. 3, 2018, which claims the benefit of U.S. Provisional Application No. 62/480,998, filed Apr. 3, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 29, 2018, is named 46482-704_601_SL.txt and is 78,248 bytes in size.

BACKGROUND OF THE DISCLOSURE

Gene therapy has long been recognized for its enormous potential in how we approach and treat human diseases. Instead of relying on drugs or surgery, patients, especially those with underlying genetic factors, can be treated by directly targeting the underlying cause. Furthermore, by targeting the underlying genetic cause, gene therapy has the potential to effectively cure patients or provide sustained treatment over a longer period of time. Yet, despite this, clinical applications of gene therapy still require improvement in several aspects. One area of concern is off target effects. An attractive approach to address off target effects is to target gene expression of gene therapy to cell type(s) or tissue(s) of interest, or the target cell type(s) or tissue(s). As such, there is a need to identify elements and methods of use thereof for targeting gene therapy or gene expression to a tissue or cell type of interest.

SUMMARY OF THE DISCLOSURE

There exists a considerable need for targeting gene therapy and gene/transgene expression thereof to the desired tissue and/or cell type in vivo, which can decrease off-target effects, increase therapeutic efficacy in the target tissue and/or cell type, and increase patient safety and tolerance by lowering the effective dose needed to achieve efficacy.

Provided herein are compositions and methods for selective expression of a transgene in a target tissue or cell type over one or more non-target tissue or cell types. Compositions and methods for selective expression of a transgene comprise one or more regulatory elements (REs) which, when operably linked to a transgene (e.g., an ion channel subunit or a neurotransmitter regulator, or a syntaxin-binding protein), can facilitate or result in selective or preferential expression of the transgene in a target tissue or cell type (e.g., parvalbumin (PV) neurons) as compared to one or more non-target cell types (e.g., non-PV cells). In some cases, the REs are non-naturally occurring sequences. In some cases, the REs are human-derived regulatory elements. In some cases, the REs comprise a sequence from a non-human species, such as a monkey, or a dog, or a rabbit, or a mouse. In some cases, the compositions described herein are delivered into a cell in vivo, ex vivo, or in vitro using a viral vector and/or virus particles, such as adeno-associated virus (AAV) or lentivirus. In some cases, the compositions described herein are delivered into a cell as gene therapy. Also contemplated herein are methods and compositions for treating a neurological condition or disorder associated with a genetic defect in the CNS. In some cases, the relevant cell type or tissue affected by the genetic defect is a PV cell. In some instances, the neurological condition or disease is Dravet syndrome, Alzheimer's disease, epilepsy, and/or seizures. In some cases, the neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated.

In one aspect, the present disclosure contemplates a nucleic acid cassette comprising one or more regulatory elements operably linked to a transgene that results in selective expression in any target cell type, e.g., PV neurons in the CNS, over one or more non-target cell types, or non-PV cells in the CNS. In some cases, each regulatory element comprises (i) a sequence of SEQ ID NOs: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is determined using BLAST. In some cases, at least one of the regulatory elements is human derived. In some cases, at least one of the regulatory elements is derived from a non-human mammal. In some cases, the regulatory elements are non-naturally occurring. In some cases, the regulatory elements result in selective expression of the transgene in PV neurons that is greater than expression of the same transgene when operably linked to a non-selective regulatory element, as measured by a co-localization assay. In some cases, the non-selective regulatory element is a constitutive promoter. In some cases, the non-selective regulatory element is any one of CAG, EF1α, SV40, CMV, UBC, PGK, and CBA. In some instances, the regulatory elements result in selective expression of the transgene in PV neurons at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, or at least 20 fold as compared to selective expression of the transgene in PV neurons when operably linked to a non-selective regulatory element, as measured by the co-localization assay. In some cases, the regulatory elements result in selective expression in PV neurons that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than expression in PV neurons when the transgene is operably linked to a non-selective regulatory element. In some cases, the regulatory elements result in selective expression in PV neurons that is about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 40 times, 50 times, or 100 times higher than expected for natural distribution of PV neurons in the CNS. In some cases, the co-localization assay is an immunohistochemical assay. In some cases, the immunohistochemical assay comprises an anti-PV antibody. In some cases, the co-localization assay is performed as shown in Example 5 below. In some cases, the transgene encodes an ion channel subunit, a neurotransmitter regulator, a DNA binding domain, a gene editing protein, or a variant or a functional fragment thereof. In some cases, the ion channel subunit is an alpha subunit or a beta subunit of a sodium ion channel or a subunit of a potassium ion channel. In some cases, the transgene comprises any one of (i) SEQ ID NOs: 37-43; (ii) a functional fragment thereof; or (iii) a sequence having at least 80% sequence identity to (i) or (ii). In some cases, sequence identity is determined using BLAST. In some cases, the transgene comprises (i) SCN1A, SNC2A, SNC8A, SCN1B, SCN2B, KV3.1, or KV3.3; (ii) a functional fragment thereof; or (iii) a sequence having at least 80% sequence identity to (i) or (ii). In some cases, the transgene is a neurotransmitter regulator that comprises (i) STXBP1, (ii) a functional fragment thereof, or (iii) a sequence having at least 80% sequence identity to (i) or (ii). In some cases, the transgene comprises a DNA binding protein that modulates expression of an endogenous gene. In some cases, the endogenous gene is SCN1A, SNC2A, SNC8A, SCN1B, SCN2B, KV3.1, KV3.2, KV3.3, or STXBP1. In some cases, the transgene comprises a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the transgene comprises a DNA binding domain linked to a transcriptional modulating domain (e.g., a transcriptional activator or repressor domain). In some cases, the gene editing protein is a Cas protein. In some cases, the regulatory elements combined are less than 2.5 kb, less than 2 kb, less than 1.5 kb, less than 1 kb, or less than 500 bp in size. In some cases, the non-PV cells comprise one or more of non-PV cell types in the CNS. In some cases, the non-PV cells comprise one or more of excitatory neurons, dopaminergic neurons, astrocytes, microglia, and motor neurons. In some cases, the nucleic acid cassette is a linear construct. In some cases, the nucleic acid cassette is a vector. In some cases, the vector is a plasmid. In some cases, the vector is a viral vector. In some cases, the viral vector is an adeno-associated virus (AAV) vector. In some cases, the AAV vector is AAV1, AAV8, AAV9, scAAV1, scAAV8, or scAAV9. In some cases, the viral vector is a lentiviral vector.

In one aspect, regulatory elements of any of the nucleic acid cassettes disclosed herein contain less than 600 bp of contiguous sequence from within 10 kb of the transcription start site of GAD2, GAD1, SYN1, NKX2.1, DLX1, DLX5/6, SST, PV, and/or VIP.

In one aspect, a method of treating a neurological disorder or condition in a subject in need thereof comprises delivering a therapeutically effective amount of any of the nucleic acid cassette disclosed herein. In some cases, the neurological disorder or condition is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological disorder or condition is Dravet syndrome or Alzheimer's disease. In some cases, the neurological condition or disease is any seizure and/or epilepsy related condition or disease wherein PV neurons are implicated.

In one aspect, a method of increasing selective expression of a transgene in PV neurons in CNS comprises contacting a cell with a nucleic acid cassette disclosed herein.

In some aspects, the present disclosure contemplates a method of targeting expression of any transgene to PV neurons in the CNS, the method comprising operably linking one or more of PV neuron selective regulatory elements to a transgene. In some cases, each of the regulatory elements comprises (i) a sequence of SEQ ID NOs: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is determined using BLAST. In some cases, the regulatory elements result in selective expression of the transgene in PV neurons that is greater than expression of the same transgene when operably linked to a non-selective regulatory element, as measured by a co-localization assay. In some cases, the immunohistochemical assay comprises an anti-PV antibody (e.g., as described in Example 5 below). In some cases, the non-selective regulatory element is a constitutive promoter. In some cases, the non-selective regulatory element is any one of CAG, EF1α, SV40, CMV, UBC, PGK, and CBA. In some cases, the regulatory elements result in selective expression of the transgene in PV neurons at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, or at least 20 fold as compared to a non-selective regulatory element when operably linked to the transgene, as measured by a co-localization assay. In some cases, the regulatory elements result in selective expression in PV neurons that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than expression in PV neurons when the transgene is operably linked to a non-selective regulatory element. In some cases, the regulatory elements result in selective expression in PV neurons that is about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 40 times, 50 times, or 100 times higher than expected for natural distribution of PV neurons in CNS. In some cases, the transgene is any one of SCN1A, SNC2A, SNC8A, SCN1B, SCN2B, KV3.1, KV3.3, STXBP1, a DNA binding protein, a gene editing protein, or a functional fragment thereof. In some cases, the regulatory elements and the transgene are in an AAV. In some cases, the AAV is AAV1, AAV8, AAV9, scAAV1, scAAV8, or scAAV9.

In another aspect, the present disclosure contemplates a method of treating a neurological condition or disorder in a subject in need thereof, the method comprising contacting a cell with a nucleic acid cassette comprising: one or more regulatory elements operably linked to a transgene that result in selective expression of the transgene in PV neurons over one or more non-PV cells in CNS. In some cases, each of the regulatory elements comprises (i) a sequence of SEQ ID NOs: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is determined using BLAST. In some cases, the transgene is a voltage-gated ion channel subunit, or a variant or a functional fragment thereof. In some cases, the subunit is a beta subunit of a sodium ion channel. In some cases, the subunit is an alpha subunit of a sodium ion channel. In some cases, the subunit is of a potassium ion channel. In some cases, the transgene is any one of (i) SCN1A, SCN1B, SCN2B, KV3.1, or KV3.3; (ii) a functional fragment thereof; or (iii) a sequence having at least 80% sequence identity to (i) or (ii). In some cases, the transgene is a DNA binding protein. In some cases, the DNA binding protein modulates an endogenous gene. In some cases, the endogenous gene is SCN1A, SNC2A, SNC8A, SCN1B, SCN2B, KV3.1, KV3.3, or STXBP1. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the transgene comprises a DNA binding domain linked to a transcriptional modulating domain (e.g., a transcriptional activator or repressor domain). In some cases, the transgene is a gene editing protein. In some cases, the gene editing protein is a Cas protein, e.g., Cas9. In some cases, the neurological condition or disorder is associated with a haploinsufficiency or a mutation in any of SCN1A, SNC2A, SNC8A, SCN1B, SCN2B, KV3.1, KV3.3, or STXBP1. In some cases, the neurological condition or disorder is epilepsy, neurodegeneration, tauopathy, or neuronal hypoexcitability. In some cases, the neurological condition or disorder is Dravet syndrome. In some cases, the neurological condition or disorder is Alzheimer's disease. In some cases, the neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated. In some cases, the regulatory elements of this disclosure result in selective expression of the transgene in PV neurons that is greater than expression of the same transgene when operably linked to a non-selective regulatory element, as measured by a co-localization assay. In some cases, the non-selective regulatory element is a constitutive promoter. In some cases, the non-selective regulatory element is any one of CAG, EF1α, SV40, CMV, UBC, PGK, and CBA. In some cases, the regulatory elements result in selective expression in PV neurons at a level that is at least 1.5 fold, at least 2 fold, at least 3 fold, at least 4 fold, at least 5 fold, at least 6 fold, at least 7 fold, at least 8 fold, at least 9 fold, at least 10 fold, at least 15 fold, or at least 20 fold as compared to a non-selective regulatory element when operably linked to the transgene, as measured by a co-localization assay. In some cases, the regulatory elements result in selective expression in PV neurons that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than expression in PV neurons when the transgene is operably linked to a non-selective regulatory element. In some cases, the regulatory elements result in selective expression in PV neurons that is about 1.5 times, 2 times, 2.5 times, 3 times, 3.5 times, 4 times, 4.5 times, 5 times, 5.5 times, 6 times, 6.5 times, 7 times, 7.5 times, 8 times, 8.5 times, 9 times, 9.5 times, 10 times, 15 times, 20 times, 25 times, 30 times, 40 times, 50 times, or 100 times higher than expected for natural distribution of PV neurons in CNS. In some cases, the nucleic acid cassette is in an AAV. In some cases, the AAV is AAV1, AAV8, AAV9, scAAV1, scAAV8, or scAAV9.

In one aspect, the present disclosure provides a method of treating Dravet syndrome, comprising contacting a cell with an AAV comprising a transgene, wherein the transgene is any one of (i) SCN1A, SNC2A, SNC8A, SCN1B, SCN2B, or a DNA binding protein, (ii) a functional fragment thereof, or (iii) a sequence having at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is measured using BLAST. In some cases, the DNA binding protein modulates an endogenous gene. In some cases, the DNA binding protein is a transcriptional modulator. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9. In some cases, the endogenous gene is SCN1A, SNC2A, SNC8A, SCN1B, or SCN2B. In some cases, the AAV further comprises one or more PV neuron selective regulatory elements or one or more regulatory elements disclosed herein operably linked to the transgene. In some cases, each of the regulatory elements independently comprises (i) a sequence of SEQ ID NOs: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii).

In another aspect, the present disclosure provides a method of treating Alzheimer's disease, comprising contacting a cell with an AAV comprising a transgene, wherein the transgene is any one of (i) SCN1A, SNC2A, SNC8A, SCN1B, SCN2B, KV3.1, KV3.3, STXBP1, or a DNA binding protein; (ii) a functional fragment thereof; or (iii) a sequence having at least 80%, at least 85%, at least 90%, at least 91%, at least 92%, at least 93%, at least 94%, at least 95%, at least 96%, at least 97%, at least 98%, or at least 99% sequence identity to (i) or (ii). In some cases, sequence identity is measured using BLAST. In some cases, the DNA binding protein modulates an endogenous gene. In some cases, the endogenous gene is SCN1A, SNC2A, SNC8A, SCN1B, SCN2B, KV3.1, KV3.3, or STXBP1. In some cases, the transgene is a DNA binding protein comprising a transcriptional modulator. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9. In some cases, the AAV further comprises one or more PV neuron selective regulatory elements or one or more regulatory elements disclosed herein operably linked to the transgene. In some cases, each of the regulatory elements independently comprises each of the regulatory elements independently comprises (i) a sequence of SEQ ID NOs: 1-32, (ii) a functional fragment or a combination thereof, or (iii) a sequence with at least 80%, at least 85%, at least 90%, at least 91%, at least 92%, at least 93%, at least 94%, at least 95%, at least 96%, at least 97%, at least 98%, or at least 99% sequence identity to (i) or (ii).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates immunofluorescence co-localization assay of CNS cells from pups following neonatal systemic injections of AAV9 comprising eGFP transgene operably linked to a regulatory element comprising a sequence of SEQ ID NO: 1 or SEQ ID NO: 8. AAV9 comprising eGFP transgene operably linked to CAG was used as a control. Lower row images illustrate eGFP+ cells. Middle row images illustrate PV+ cells, which were stained with an anti-PV antibody. Top row images (merge) illustrate an overlay of PV+, eGFP+ fluorescence (with representative eGFP+ and PV+ cells which are shown as white or light grey cells indicated by arrowheads) and DAPI+.

FIG. 5A illustrates the immunofluorescence co-localization assay performed with AAVDJ comprising one of SEQ ID NO: 2, SEQ ID NO: 3, SEQ ID NO: 4, and SEQ ID NO: 5 operably linked to eGFP. FIG. 5B illustrates the immunofluorescence co-localization assay performed with AAVDJ comprising one of SEQ ID NO: 6, SEQ ID NO: 7, and SEQ ID NO: 9 operably linked to eGFP. FIG. 5C illustrates the immunofluorescence co-localization assay performed with AAVDJ comprising one of SEQ ID NO: 10, SEQ ID NO: 11, SEQ ID NO: 12, and SEQ ID NO: 13 operably linked to eGFP. FIG. 5D illustrates the immunofluorescence co-localization assay performed with AAVDJ comprising one of SEQ ID NO: 14, SEQ ID NO: 15, SEQ ID NO: 16, and SEQ ID NO: 17 operably linked to eGFP. FIG. 5E illustrates the immunofluorescence co-localization assay performed with AAVDJ comprising one of SEQ ID NO: 18, SEQ ID NO: 19, SEQ ID NO: 20, and SEQ ID NO: 21 operably linked to eGFP. FIG. 5F illustrates the immunofluorescence co-localization assay performed with AAVDJ comprising SEQ ID NO: 22 or SEQ ID NO: 34 operably linked to eGFP, wherein SEQ ID NO: 34 is a previously characterized non-selective regulatory element and was used as a control for comparison.

DETAILED DESCRIPTION OF THE DISCLOSURE

Figure 1:
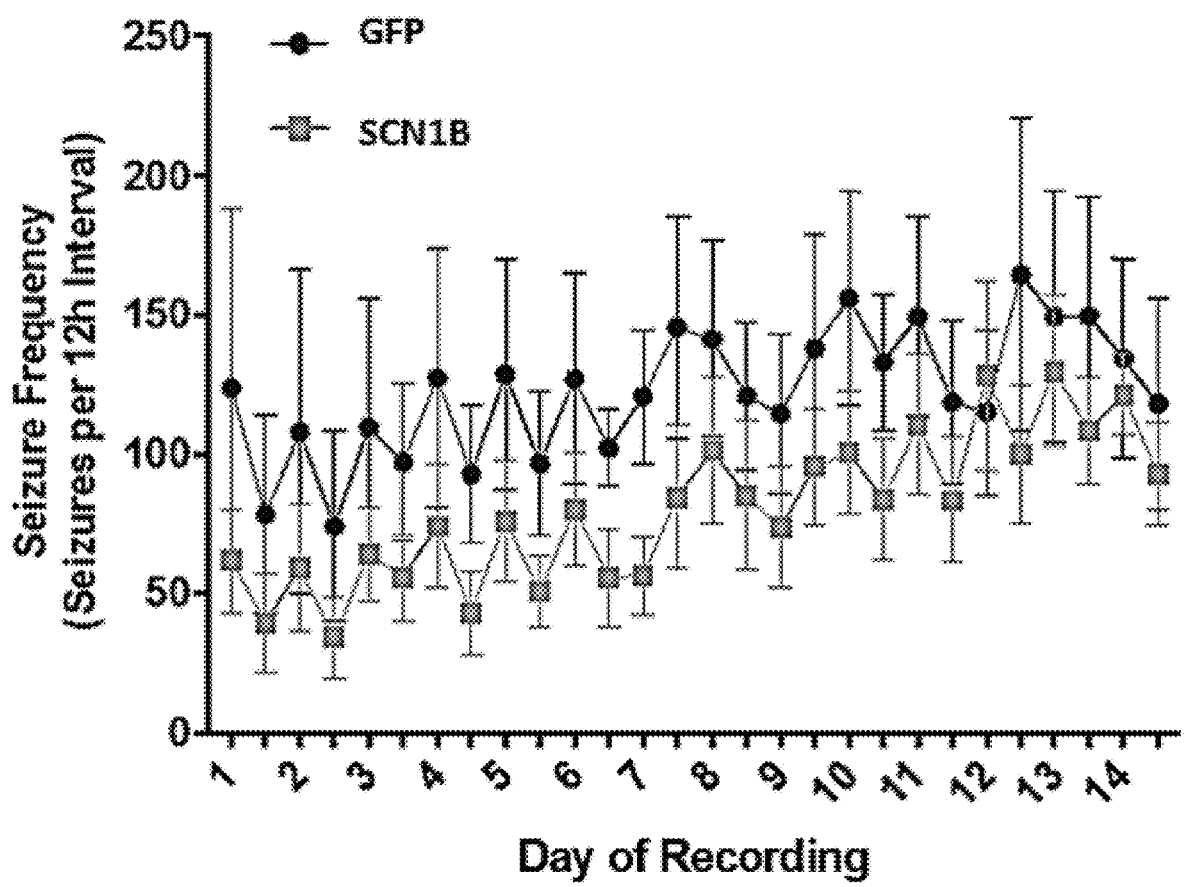
FIG. 1 illustrates the frequency of seizures (seizures per 12 hr interval) in SCN1A heterozygous mice after treatment with a recombinant AAVDJ vector comprising either SCN1B or eGFP operably linked to a regulatory element comprising a sequence of SEQ ID NO: 32. The graph illustrates the mean values at each day of recording with error bars representing the standard error of the mean.

The present disclosure contemplates compositions and methods of using such compositions in gene therapy to treat a disease or condition associated with the central nervous system (CNS), e.g., Dravet syndrome, Alzheimer's disease, epilepsy, and/or seizures.

Gene therapy can replace, modify, delete, or add a gene or a specific nucleic acid sequence, such as an expression cassette, to impart a therapeutic effect in a cell. In some cases, gene therapy is used to deliver an expression cassette into a cell that produces or results in a therapeutic effect. In some cases, a virus, such as AAV, comprising a viral vector that comprises an expression cassette can be used to deliver a transgene into a cell. The expression cassette can contain a transgene that provides a therapeutic effect when expressed in a cell.

One challenge in gene therapy is ensuring that the transgene is expressed in an appropriate cell type of interest, or the target cell type, to effect or target gene expression. Traditional methods for targeting gene therapy have often relied on delivery methods and/or vehicles (e.g., varying the viruses used or capsid sequences of viruses). In addition to targeting, or selective expression, of an expression cassette in the target cell type over one or more non-target cell types, another challenge in the field is increasing gene expression, especially when the gene is large, in a target cell type or tissue to exert a therapeutic effect.

The present disclosure provides a plurality of regulatory elements, which are non-coding nucleotide sequences, that can be operably linked to any transgene to increase or to improve selectivity of the transgene expression in the CNS, e.g., in PV neurons. By increasing selectivity of gene expression using one or more regulatory elements disclosed herein, one can improve the efficacy of a gene therapy, decrease the effective dose needed to result in a therapeutic effect, minimize adverse effects or off-target effect, and/or increase patient safety and/or tolerance.

In one aspect, one or more regulatory elements can be operably linked to any transgene in an expression cassette to modulate gene expression in a cell, such as targeting expression of the transgene in a target cell type or tissue (e.g., PV cells) over one or more non-target cell type or tissue (e.g., non-PV CNS cell-types). In some cases, targeting expression of the transgene in a target cell type or tissue includes increased gene expression in the target cell type or tissue. One or more regulatory elements operably linked to a transgene can be part of an expression cassette, which can be a linear or a circular construct, a plasmid, a vector, a viral vector, e.g., a vector of an adeno-associated virus (AAV). Such expression cassette can be adapted for gene therapy or delivery into a subject (e.g., a human, a patient, or a mammal). In some cases, operably linking one or more regulatory elements to a gene results in targeted expression of the gene in a target tissue or cell type in the CNS, such as a parvalbumin (PV) neuron. In some cases, one or more regulatory elements (e.g., SEQ ID NOs: 1-32, or a functional fragment or a combination thereof, or sequences having at least 80%, at least 90%, at least 95%, or at least 99% sequence identity thereto) increase selectivity of gene expression in a target tissue or cell type in the CNS, such as PV neurons. In some cases, a gene therapy comprises one or more regulatory elements disclosed herein, wherein the regulatory elements are operably linked to a transgene and drive selective expression of the transgene in PV neurons.

In some cases, selective expression of a gene in PV neurons is used to treat a disease or condition associated with a haploinsufficiency and/or a genetic defect in an endogenous gene, wherein the genetic defect can be a mutation in the gene or dysregulation of the gene. Such genetic defect can result in a reduced level of the gene product and/or a gene product with impaired function and/or activity. In some cases, an expression cassette comprises a gene, a subunit, a variant or a functional fragment thereof, wherein gene expression from the expression cassette is used to treat the disease or condition associated with the genetic defect, impaired function and/or activity, and/or dysregulation of the endogenous gene. In some cases, the disease or condition is Dravet syndrome, Alzheimer's disease, epilepsy, neurodegeneration, tauopathy, neuronal hypoexcitability and/or seizures.

In some cases, the transgene is an ion channel or a neurotransmitter regulator, a DNA binding protein, or a subunit, variant, or functional fragment thereof. In some cases, the transgene is a sodium ion channel alpha subunit, sodium ion channel beta subunit, or a variant or functional fragment thereof. In some cases, the transgene is a potassium ion channel or a subunit thereof. In some cases, the transgene is SCN1A, SNC2A, SNC8A, SCN1B, SCN2B, KV3.1, KV3.2, KV3.3, STXBP1, a DNA binding protein (e.g., a DNA binding protein that modulates expression of an endogenous gene), or a variant or functional fragment thereof. In some cases, the transgene comprises a sequence having at least 80%, at least 85%, at least 90%, at least 95%, at least 96%, at least 97%, at least 98%, or at least 99% sequence identity to any one of SCN1A, SNC2A, SNC8A, SCN1B, SCN2B, KV3.1, KV3.2, KV3.3, STXBP1, a DNA binding protein, or a variant or functional fragment thereof. In some cases, the transgene is a DNA binding protein that modulates expression of an endogenous gene, such as any one of SCN1A, SNC2A, SNC8A, SCN1B, SCN2B, KV3.1, KV3.2, KV3.3, and STXBP1.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1%) of a given value.

The terms "determining", "measuring", "evaluating", "assessing", "assaying", "analyzing", and their grammatical equivalents can be used interchangeably herein to refer to any form of measurement, and include determining if an element is present or not (for example, detection). These terms can include both quantitative and/or qualitative determinations. Assessing may be relative or absolute.

The term "expression" refers to the process by which a nucleic acid sequence or a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "operably linked", "operable linkage", "operatively linked", or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

A "vector" as used herein refers to a macromolecule or association of macromolecules that comprises or associates with a polynucleotide and which can be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target. The combination of regulatory elements and a gene or genes to which they are operably linked for expression is referred to as an "expression cassette".

The term "AAV" is an abbreviation for adeno-associated virus, and may be used to refer to the virus itself or a derivative thereof. The term covers all serotypes, subtypes, and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV1, AAV2, AAV3, AAV4, AAV5, AAV6, AAV7, AAV8, AAV9, AAV10, AAV11, AAV12, rh10, and hybrids thereof, avian AAV, bovine AAV, canine AAV, equine AAV, primate AAV, non-primate AAV, and ovine AAV. The genomic sequences of various serotypes of AAV, as well as the sequences of the native terminal repeats (TRs), Rep proteins, and capsid subunits are known in the art. Such sequences may be found in the literature or in public databases such as GenBank. An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs). The term rAAV vector encompasses both rAAV vector particles and rAAV vector plasmids. An rAAV vector may either be single-stranded (ssAAV) or self-complementary (scAAV). An "AAV virus" or "AAV viral particle" or "rAAV vector particle" refers to a viral particle composed of at least one AAV capsid protein and an encapsidated polynucleotide rAAV vector. If the particle comprises a heterologous polynucleotide (i.e., a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

As used herein, the terms "treat", "treatment", "therapy" and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some cases, for prophylactic benefit, the compositions are administered to a subject at risk of developing a particular disease, or to a subject reporting one or more of the physiological symptoms of a disease, even though a diagnosis of this disease may not have been made. The methods of the present disclosure may be used with any mammal. In some cases, the treatment can result in a decrease or cessation of symptoms (e.g., a reduction in the frequency or duration of seizures). A prophylactic effect includes delaying or eliminating the appearance of a disease or condition, delaying or eliminating the onset of symptoms of a disease or condition, slowing, halting, or reversing the progression of a disease or condition, or any combination thereof.

The term "effective amount" or "therapeutically effective amount" refers to that amount of a composition described herein that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in a target cell. The specific dose will vary depending on the particular composition chosen, the dosing regimen to be followed, whether it is administered in combination with other compounds, timing of administration, the tissue to which it is administered, and the physical delivery system in which it is carried.

A "fragment" of a nucleotide or peptide sequence is meant to refer to a sequence that is less than that believed to be the "full-length" sequence.

A "variant" of a molecule refers to allelic variations of such sequences, that is, a sequence substantially similar in structure and biological activity to either the entire molecule, or to a fragment thereof.

The term "functional fragment" is intended to include the "fragments", "variants", "analogues", or "chemical derivatives" of a molecule.

A "functional fragment" of a DNA or protein sequence possesses at least a biologically active fragment of the sequence, which refers to a fragment that retains a biological activity (either functional or structural) that is substantially similar to a biological activity of the full-length DNA or protein sequence. A biological activity of a DNA sequence can be its ability to influence expression in a manner known to be attributed to the full-length sequence. For example, a functional fragment of a regulatory element will retain the ability to influence transcription as the full-length RE.

The terms "subject" and "individual" are used interchangeably herein to refer to a vertebrate, preferably a mammal, more preferably a human. "Subject" refers to an animal, such as a mammal, for example a human. The methods described herein can be useful in human therapeutics, veterinary applications, and/or preclinical studies in animal models of a disease or condition. In some case, the subject is a mammal, and in some cases, the subject is human.

The term "in vivo" refers to an event that takes place in a subject's body.

The term "in vitro" refers to an event that takes places outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

Sequence comparisons, such as for the purpose of assessing identities, mutations, or where one or more positions of a test sequence fall relative to one or more specified positions of a reference sequence, may be performed by any suitable alignment algorithm, including but not limited to the Needleman-Wunsch algorithm (see, e.g., the EMBOSS Needle aligner available at www.ebi.ac.uk/Tools/psa/emboss_needle/, optionally with default settings), the BLAST algorithm (see, e.g., the BLAST alignment tool available at blast.ncbi.nlm.nih.gov/Blast.cgi, optionally with default settings), and the Smith-Waterman algorithm (see, e.g., the EMBOSS Water aligner available at www.ebi.ac.uk/Tools/psa/emboss_water/, optionally with default settings). Optimal alignment may be assessed using any suitable parameters of a chosen algorithm, including default parameters.

In general, "sequence identity" or "sequence homology", which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity", also referred to as "percent homology". The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin and Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values there between. Typically, the percent identities between a disclosed sequence and a claimed sequence are at least 80%, at least 85%, at least 90%, at least 95%, at least 98%, or at least 99%. In general, an exact match indicates 100% identity over the length of the reference sequence. In some cases, reference to percent sequence identity refers to sequence identity as measured using BLAST (Basic Local Alignment Search Tool). In other cases, ClustalW can be used for multiple sequence alignment.

Unless otherwise indicated, all terms used herein have the same meaning as they would to one skilled in the art and the practice of the present invention will employ, conventional techniques of molecular biology, microbiology, and recombinant DNA technology, which are within the knowledge of those of skill of the art.

Regulatory Elements

Regulatory elements are nucleic acid sequences or genetic elements which are capable of influencing (e.g., increasing or decreasing) expression of a gene and/or confer selective expression of a gene (e.g., a reporter gene such as eGFP, a transgene, or a therapeutic gene) in a particular tissue or cell type of interest. In some cases, a regulatory element can be a transgene, an intron, a promoter, an enhancer, UTR, insulator, a repressor, an inverted terminal repeat (ITR) sequence, a long terminal repeat sequence (LTR), stability element, posttranslational response element, or a polyA sequence, or a combination thereof. In some cases, the regulatory element is a promoter or an enhancer, or a combination thereof. In some cases, the regulatory element is derived from a human sequence.

In some cases, the cell type of interest is a PV neuron. Regulatory elements can function at the DNA and/or the RNA level. Regulatory elements can function to modulate gene expression selectivity in a cell type of interest. Regulatory elements can function to modulate gene expression at the transcriptional phase, post-transcriptional phase, or at the translational phase of gene expression. Regulatory elements include, but are not limited to, promoter, enhancer, repressor, silencer, and insulator sequences. At the RNA level, regulation can occur at the level of translation (e.g., stability elements that stabilize mRNA for translation), RNA cleavage, RNA splicing, and/or transcriptional termination. In some cases, regulatory elements can recruit transcriptional factors to a coding region that increase gene expression selectivity in a cell type of interest. In some cases, regulatory elements can increase the rate at which RNA transcripts are produced, increase the stability of RNA produced, and/or increase the rate of protein synthesis from RNA transcripts. In some cases, regulatory elements can prevent RNA degradation and/or increase its stability to facilitate protein synthesis. In some cases, regulatory elements suppress transcription and/or translation processes in off-target cell-types. In some cases, off-target cell-types include, but are not limited to, excitatory neurons, non-PV CNS cell-types, and non-neuronal CNS cell types.

Various assays including, but not limited to, DNAase hypersensitivity, ATAC-Seq, and ChIP-Seq can be used to identify putative non-coding regulatory elements (REs). The enzymatic reaction in each of these assays preferentially targets open/accessible chromatin states, a state which is thought to be predictive of regulatory elements. To discover cell-type selective regulatory elements, one can assay for open chromatin sequence for target cell-type of interest (e.g., parvalbumin neurons) and compare that to open chromatin sequences for non-target cell types (e.g., excitatory neurons). Additional filters can be applied to further refine target selection, including proximity to a cell-type selective gene, species conservation, and/or sequence motifs, such as transcription factor binding sites. DNA sequences that are uniquely identified in the target cell type can be synthesized and cloned into an expression vector. The selectivity of a regulatory element can be determined using immunohistochemical methods to quantify co-localization to known cell-type selective proteins.

For example, one method of isolating a cell-type selective regulatory element includes isolating nuclei from a brain tissue or cell type of interest from an animal model, which can be achieved by using an affinity purification method that isolates the tissue or cell type of interest (e.g., using beads coated to an anti-PV antibody for isolating PV neurons), using high-throughput natural priming and DNA synthesis to generate a pool of sequences from open chromatin regions in the nuclei, sequencing the pool of sequences to identify putative sequences that drive gene expression in the tissue or cell type of interest, and verifying selective expression in a reporter system in a cell line in vitro and/or in an animal model.

Another method for identifying candidate regulatory elements that are selective in a tissue or cell type of interest include using R26-CAG-LSL-Sun1-sfGFP-Myc knockin mouse for harvesting the tissue or cell type of interest, isolating GFP+/Myc+ nuclei from the mouse neocortex of this strain using affinity purification, e.g., using anti-GFP or anti-Myc antibodies and protein G-coated magnetic beads to isolate nuclei from the neocortex. Nuclear RNA from purified nuclei or whole neocortical nuclei can be converted to cDNA and amplified with the Nugen Ovation RNA-seq System V2 (Nugen 7102), followed by sequencing using the Illumina HiSeq 2500. Genomic DNA from purified nuclei can be fragmented and used to make MethylC-seq libraries, which can be sequenced using the Illumina HiSeq 2000. To generate an ATAC-seq library, nuclei bound to beads are transposed using Tn5 transposase (Illumina FC-121-1030). After 9-12 cycles of PCR amplification, libraries are sequenced using an Illumina HiSeq 2500. To generate a ChIP-seq library, excitatory neuron nuclei can be digested to mononucleosomes using micrococcal nuclease, followed by salt extraction of chromatin, and native ChIP and library construction, which can be sequenced on an Illumina HiSeq 2500. After sequencing these libraries, the sequences are mapped to identify, for example, correlation in cell-type-specific hypo-methylation in CG-rich regions, histone modifications, transcriptional factor binding sites, and patterns associated with highly expressed transcriptional factors. Overlapping features and correlations from multiple assays and/or libraries described above provide evidence for identifying candidate sequences within such genomic regions as potential regulatory elements associated with selective expression and/or high expression in the cells isolated from the neocortex. For example, a genomic region characterized by a strong overlap between hypomethylation detected in the methy1C-seq library, ChIP assay, and an enrichment in transcription factor binding motifs in the same region provide convergent data that indicate the genomic region contains a sequence of a putative regulatory element selective for the tissue or cell type isolated. As another example, to identify candidate PV neuron selective regulatory elements, one can isolate PV neurons and purify nuclei from the isolated PV cells so that genomic sequences that are identified as active in multiple sequencing assays described above have a high likelihood of being PV cell-selective regulatory elements, e.g., a genomic region that is identified as active in an ATAC-seq assay (corresponding to regions of open chromatin), active in RNA-seq (indicative of active gene expression and low DNA methylation patterns in the region), and active in methylC-seq assay (which generates single-base resolution methylome maps from a cell type of interest).

Once candidate genomic regions are identified as selectively active in a cell type of interest, sequences within the region can be generated using PCR methods and tested in additional assays in vitro and/or in vivo to validate tissue or cell type selectivity of the sequences. Such validation assays include immunohistochemical co-localization assay, wherein an antibody or any detectable marker is used to label the cell type of interest and a second detectable marker, e.g., a fluorescent transgene, is operably linked to the putative regulatory elements. Expression cassettes comprising such elements are delivered into cells in vitro and/or in vivo. Selective expression driven by one or more putative regulatory elements can be validated by measuring the overlap between the cell type of interest (as measured by the detectable signal or fluorescence from its labeled marker, e.g., an anti-PV antibody) and the second detectable marker corresponding to expression of the transgene (e.g., eGFP or RFP) operably linked to the regulatory elements. An overlap in the signals from both detectable markers indicates cell-type selectivity in the labeled cell type if the amount of overlap observed is higher than the overlap observed when the regulatory elements are replaced with a control, such as CAG, EF1α, a constitutive promoter (e.g., SV40, CMV, UBC, PGK, and CBA), a non-selective regulatory element, or a previously characterized non-selective regulatory element. Various mouse strains adapted for expressing a detectable marker in a cell type of interest allows validation of cell type selectivity of a regulatory element in vivo. For example, a number of mouse lines that express Cre in a particular cell type can be used because cell-type selective Cre expression can drive Cre-induced expression of a fluorescent protein, such as RFP, in a cell type of interest. Labeling such cell type of interest in vivo allows one to determine level of cell-type selective expression that is associated with a putative regulatory element operably linked to a fluorescent or reporter transgene in the same mouse. Similar to the co-localization assay, an overlap of the signals from both markers that exceeds the overlap detected for CAG, EF1α, a constitutive promoter (e.g., SV40, CMV, UBC, PGK, and CBA), or a non-selective regulatory element is indicative of cell type selectivity for the regulatory elements tested. In some cases, the mouse strain used is B6 PV-Cre mouse (Jackson Laboratory), which is a B6 PV-Cre knock-in mouse that expresses Cre recombinase in parvalbumin-expressing neurons (e.g., interneurons in the brain and proprioceptive afferent sensory neurons in the dorsal root ganglia), without disrupting endogenous Pvalb expression.

Upon validation of cell type selectivity of a regulatory element for a particular cell type, sequences of such regulatory elements can be varied using various mutagenesis methods, e.g., error-prone PCR methods, to improve its selectivity. In some cases, two or more regulatory elements having cell selectivity can be combined. In some cases, combined regulatory elements exhibit enhanced cell-type selectivity in driving gene expression in the cell type of interest. In some instances, such regulatory elements are truncated one or more bases at a time to determine the minimal amount of sequence that retains its cell type selectivity. Smaller regulatory elements that retain cell type selectivity are helpful for making gene therapy comprising a large transgene, or where the cloning capacity of a vector or plasmid is limited in view of the size of a transgene that one wishes to deliver using gene therapy.

The present disclosure provides a plurality of nucleotide sequences that are regulatory elements. In some cases, any one or more of the regulatory elements disclosed herein result in increased selectivity in gene expression in a parvalbumin cell. In some cases, regulatory elements disclosed herein are PV-cell-selective. In some cases, PV cell selective regulatory elements are associated with selective gene expression in PV cells more than expression in non-PV CNS cell-types. In some cases, PV cell selective regulatory elements as associated with reduced gene expression in non-PV CNS cell types.

Non-limiting examples of regulatory elements include SEQ ID NOs: 1-32, as provided in TABLE 1 below.

TABLE 1

List of nucleic acid sequences disclosed herein.

| SEQ ID NO: | Nucleic Acid Sequence | Source/ Genomic Location |
|---|---|---|
| 1 | GGAGGAAGCCATCAACTAAACTACAATGACTGTAAGATACAAA<br>ATTGGGAATGGTAACATATTTTGAAGTTCTGTTGACATAAAGAA<br>TCATGATATTAATGCCCATGGAAATGAAAGGGCGATCAACACT<br>ATGGTTTGAAAAGGGGGAAATTGTAGAGCACAGATGTGTTCGT<br>GTGGCAGTGTGCTGTCTCTAGCAATACTCAGAGAAGAGAGAGA<br>ACAATGAAATTCTGATTGGCCCCAGTGTGAGCCCAGATGAGGTT<br>CAGCTGCCAACTTTCTCTTTCACATCTTATGAAAGTCATTTAAGC<br>ACAACTAACTTTTTTTTTTTTTTTTTTTTTTGAGACAGAGTCTTG<br>CTCTGTTGCCCAGGACAGAGTGCAGTAGTGACTCAATCTCGGCT<br>CACTGCAGCCTCCACCTCCTAGGCTCAAACGGTCCTCCTGCATC<br>AGCCTCCCAAGTAGCTGGAATTACAGGAGTGGCCCACCATGCC<br>CAGCTAATTTTTGTATTTTTAATAGATACGGGGGTTTCACCATAT<br>CACCCAGGCTGGTCTCGAACTCCTGGCCTCAAGTGATCCACCTG<br>CCTCGGCCTCCCAAAGTGCTGGGATTATAGGCGTCAGCCACTAT<br>GCCCAACCCGACCAACCTTTTTAAAATAAATATTTAAAAAATT<br>GGTATTTCACATATATACTAGT | Human; hg19: chr2: 171621900- 171622580 |
| 2 | AGTTTGGACAAGAACTATAGTTCTAGCTTTCTCTGGGTCTCCAC<br>CTTGCAGAGAATGCAGCTTTCATTATCTCATGAGCCAAACTCTC<br>ATCATCTCTTTCCATATATCTGTCGGTGCTCTTCCATGAGTACTC<br>TAACACACACAGAAGGAGCACTTACACAGGCTGTTGTTTTCTC<br>TTATTATCATAGCTGTTGTTCAGACATGTGCATTCTGTTCTTGTT<br>GCTTCAATGCTAAAGGAGTCTCAGGATATGAGAACTGTACCAG<br>CCGAGGCATCAGGAAACATGGGTGGAAATTCCCACAGTACTAT<br>TTGTTCACTGTGTGACCTTGGGCCAGTCACATCCCTTTCCTGAG<br>GCTTCGATTCCCCAAGCTATAAAAGAAGCATCTCTTAACCTTTT<br>TTTAGGTCATGAGTCAGGCCCAGCACACTCTCAGGGAGACTCAT<br>GAGAGTACAGATCATTTCCCATAGAAAAACCATAGTTTTATATC<br>CAGAGGCTTTTCTGTAAG | Mouse; mm10: chr2: 36053858- 36054359 |
| 3 | GGTTCCAGTTCAGAGGCAGAGCATTTGGGGTTCCCAGTCAGGA<br>GCTTTCCTCTCTCCGCTCCTTAGTTTCCTCTCTTTAAAAAAAAAT<br>GGGTGATAGTATAGAAAGGAAGCTCTGGGCTCGGGGACCAGGG<br>CCCTGGGATCCCCGCTCCCAGCCACTCGCTCCTGACCCTTCCAG<br>GGACAAGCTCCCCCCCACCCCGTCCTTTCCAGGCTGCCACTAGA<br>AGAGATGGGGACGCGTGGTCAGCCGCTTCTGTCGCCCCCCAGG<br>GAACGGTCTCACGCTGGAGGGGGCAGTGCCCTCGGAACAGGAC<br>AGTCAGCCCAAGCCAGCCAAGCGCGCGCGGACGTCCTTCACCG<br>CAGAGCAATTGCAGGTACCCCGGGCAAGCCCCGAAGCGTGTGG<br>GCGGGGCTTCGGAGTGGGCGTGGTTGTTCGGGACTTGTGACTCC<br>GCCCCTTGTGCGGGGACCCGCGTGAGGCCGCTCCAAGGATGAA<br>GCTGCCTGGGGCGTGGCCTCGGACCCTGAGCCTCTGATTGGGCG<br>GAGGTCTCAGGGCCCTTCTGCGCCCCACAGGTTATGCAGGCGCA<br>GTTCGCGCAGGACAACAACCCGGACGCGCAGACGCTGCAGAAG<br>CTGGCGGACATGACGGGCCTCAGTCGCAGGGTCATCCAGGTGG<br>GGCTCCGGGGTCTCGGCCTTCAGGTCTAGGGTGAACCTTAGGGA<br>AGCGCTGAAGCTCGTAGTGGTACGGATGGTCGCGCGTGCACGT<br>GGCCGCCCCTCTCCAGTGTGGCCTAAGGACCCCAGTCGGCACG<br>GGTTGACCCTTTTCCTTGATTACTGAGAGTGCAGAGGCTGT | Mouse; chr2: 36,091,144- 36,091,966 |
| 4 | TGGTGGGAAGACATGTCCAGGGAAGAAATGGCCTCCAGAGGCC<br>TGAGGTGGGAAATGCTGGAGGTGGAGAGAGGAACAACTGACT<br>GAAAATGAGCTTCCACTGTGGCTTAGTAGCCTATACCAAGTCTA<br>GAGTATAGGGTAGGAGAAGATTAGGAAAGCGATGGGTCTGAGA<br>ATGATGTGGCTGTTGACTTTTGTAAACCCAAAGCACCTTGGAC<br>TAAACCCTATGAACAGTGTGGTGCCACCAAAGACTATAATGAG<br>CTCAGGGAACAGAATTCTGTGTGCATGGTGATTTTTTTTTTTTT<br>TTCTGCTAACTGCAGTCTGGGTGATGCATTGACAAACCAATCCT<br>GGAAAGTAAGAGGCAAGGGCAGCTGGGACGGTGAGAGGAGCC<br>TGATGGGAACCAGGCCAAGCAGGGCAGCAGAGGCGATGAAGA | Mouse; chr2: 36,095,396- 36,096,028 |

TABLE 1-continued

List of nucleic acid sequences disclosed herein.

| SEQ ID NO: | Nucleic Acid Sequence | Source/ Genomic Location |
|---|---|---|
| | GGATGTGGTGCATCCAGAGACTCACTTCATTAGCTGGAGGCACT GCTGGATAGGGTCTGAAGGTTCTGGTATCTGAGTTGGCGGGCTG GGTGAGTGGTGGCTCTGCTTCCTGAACAGTGTGTGCAAGAGGA AACAGGGTTAAGGGCTAGGACAGTCACAGGTGAGTCAGCCTCA CAAGAGCAACCTTCCCCTAGTGCAGA | |
| 5 | GGAGGTCTCCTTTTGCCCCGGTTCCAACAAGAGAATGCAAGGCT GTATCTCAATTTCCTTGAGCCTCTCTGTATTATAGAAGAAAAGT AGGGGAAGCCATACGCCCCTTCTGAGCTTCAGTGTCTCTCTGTCT CTGCAAATGAGGCTGGGGAGGCTGGGGCGGGCGTGAAAGAG GCCCGCGCCAAGCCGACCCCCACCTCTGCCCCCTCCCCAGGTCA ACAACCTCATCTGGCACGTGCGGTGCCTCGAGTGCTCCGTGTGT CGCACATCGCTGAGGCAGCAGAATAGCTGCTACATCAAGAACA AGGAGATCTACTGCAAGATGGACTACTTCAGGTAGGCAGCGGC CATCCCGCCAGCAAGCGCTGGAGCATGAACGCCTTGCACACGC GTGCCTAGGCCACTTGTGTGGCCTGTGCTCTCCAATTCCTGAGC CCTGCTGTTCAGAGTGCACAACGCGGCTCAGCGCACTGGCCCG GCCCTCCTACTCAGCACGTCTTACACAGAAGGGAGCGCCAGTCT CAGCCTGAGTTCTGGCGGGGATCTGCCTCGGGTTCCTCCGATC TGACAGGCGCTGGCCACGGGTCTGGTTCCATCTCTGGTCTTTTC TGGCCCCGAGCACCAGTGTGTTCTGTTGAGCTCTGATGTCCGAG GCTCTGGCCCGGATCA | Mouse; mm10: chr2: 36102524- 36103193 |
| 6 | CTCTGGCTACCTCTTATCTTGGGCATTCACGACAATTTCTAATTG CAGGTAGTTTGTGTGTGTGCGCGTGTTTTTTTTCCCCCTCAGAGG CTTGGATTGCAAAGGAACTAAGCGATTACTTCAAGAGCCACGG GTTAAGTGCAGGGAGAGGGGGAGAGAGAGGGAAAAAAACCCA ATCCAAATTCAAATTGCTTCATTAGAGAGACACCGCTTTTGTGG GGAAGGGCTTTAAATGCCCACTACAAAGTTAGGACTCATTGTTC AGCGCCGGTTTATATAACAGGCGAGGGGAGGCGCTGGGCTCTG ACAGCTCCGAGCCAGTTCAGCAGCCGCCGTCGCCTGCATTCCCT CCCCCTCCCCCAGGTGATGGCCCAGCCAGGGTCCGGCTGCAAA GCGACCACCCGCTGTCTCGAAGGGACCGCTCCGCCTGCCATGGT GAGTCCTTTCGGTCCTGCTTTCGGCCCCGAGTCCCCCCAACAGC ACAGGCCAGGGCTTCTGGCTCAGCCTTCCGGCTACCAACCTCTA CCCCTGCGCTGGAAAACTGCCGATAGGAGCCGCCTCTCGTTGAG CCTTGGTTTTTCTGGCCTGGAATGTGAGCTTTGGCTGCTTCCTGC ACCCAGGATGCGCTGTGTTAAAAGTTGGGGGCCGTCCCTTCTTC TCCAATAGGTCCTTTCATTCTTGTACTCCAGCCTAGGGCGCGAC ATCCCTGGCACATTTCGGTGTCAGTCGGTGCGCGAGGAAACCA GATTCAACTCTGAGTACTCGGCTAAGCGCTTCGCTGTTCCTCTCT CCCATTTCAGGCTCAGTCAGACGCAGAGGCCTTGGCAGGCGCTC TGGACAAGGACGAAGGTAGAGCCTCCCCATGTACGCCCAGCAC ACCGTCTGTCTGCTCGCCGCCCTCTGCTGCCTCTTCCGTGCCGTC TGCCGGCAAGAATATCTGCTCCAGTTGCGGTCTGGAGATCCTGG ACCGGTATCTGCTCAAGGTGAGTCAGGGTAGGTGTGCCTGCTTG CCCACGGGTGTGGTTTGCAGCCCCAAGAGCTGT | Mouse; mm10: chr2: 36103286- 36104328 |
| 7 | CAAGACTTTTAAAAGTTTAGATAAATAAACAAACATTTGACGGC TTTCCATCACATCTAGACTATAATCCAAAGATCTATATGGTCCC AAACGACTTACACTTAACTACCGTCTCCCATATGGCTTCTTCCC CCATCAGTCATTGTCCTCAGCCATAGTGGCCTCCCTGTTCCTTTG GGTACAAGGGAACAACTCCCTGAGAGGTTCCATTAGCTGCTGTT GCCTGAGATGCTCTTGAGCCCACACCATCTGCTCATTTCTCTCCT CACGTGTCAGTGATTAAGAGGCTGTCCTTGGCCTCCCGTCAAAA TTACATCCCTGCCGCTTTCCACTTCTTGCCTTCTTATTTTCTAAAT AGAACTAACTCACCACTACCCAACATTCTATATAATTGGATATC TGTCCTCTGTTTAAATATAATGTTGACTTCAAGAAAGAACGTTG TCACTGCCCTGTCACCAGACTTTTAAACAGTGCCTATCGTGTGG CACATGCTCAGTGAAATTG | Mouse; mm10: chr2: 36114311- 36114817 |
| 8 | TCAACAGGGGACACTTGGGAAAGAAGGATGGGACAGAGCC GAGAGGACTGTTACACATTAGAGAAACATCAGTGACTGTGCCA GCTTTGGGGTAGACTGCACAAAAGCCCTGAGGCAGCACAGGCA GGATCCAGTCTGCTGGTCCCAGGAAGCTAACCGTCTCAGACAG AGCACAAAGCACCGAGACATGTGCCACAAGGCTTGTGTAGAGA GGTCAGAGGACAGCGTACAGGTCCCAGAGATCAAACTCAACCT CACCAGGCTTGGCAGCAAGCCTTTACCAACCCACCCCCACCCCA CCCACCCTGCACGCGCCCCTCTCCCCTCCCCATGGTCTCCCATG GCTATCTCACTTGGCCCTAAAATGTTTAAGGATGACACTGGCTG CTGAGTGGAAATGAGACAGCAGAAGTCAACAGTAGATTTTAGG AAAGCCAGAGAAAAGGCTTGTGCTGTTTTTAGAAAGCCAAGG GACAAGCTAAGATAGGGCCCAAGTAAT | Mouse; mm10: chr15: 78179109- 78179610 |

TABLE 1-continued

List of nucleic acid sequences disclosed herein.

| SEQ ID NO: | Nucleic Acid Sequence | Source/ Genomic Location |
| --- | --- | --- |
| 9 | AAATAGAACTGTGAGATAGGGGGAGAGGGGGCAGGAAGGACA AGAGACCCCTGTCTCATTGTGATCCCCACCTGTCTGCTCTGTGG GAGGGTACCCATGAGGGCCAGCCCACAGCCCTTAGGTGGACAT TGTCTGGTCCTGTCTCACTGTCCCTCCCAGCAGCCCCAGAGGCC AGGAGACAGGGGTCTCAGTCCTCACTGAGAGATGTGTAAACTG AGGCCCAGTGAATGTTGAGGGCCAGGGCATGCCCTTGGTGGGA TGTGACCTGGGTCTCCTTCGCACGGGCTTCCTCCCCGAAGCCGA GCTGAGCATTTGGAGTTTGAAATGTTTCCGTACTTAGCAATCTG CTCCTCTATTCCCGGGCGGACTTCCGATAGCTCCGGCCTTATGC TGCACTAGATAAGATGGAGCAGGGAGAGGACACGGCACTACTT ATGTAACCGGCCTCTTGAAAAATGGAGCAGCGGTCAGGGCGGA ACAAGACGTCCTCTCTCTACGCATCCCTCTCCTTTCCCTGCTAAG GCTGCAGCTGGAGTCAGAGGCAGGGCTGTTCCAATCTGTCTTTG ATCAGTAACGCAGCCAGCCTCCAGCCTCCGTCAGCCTCCTCATG GCTGAGACCCGGCCTCAGTTTCCCCCACTTACATCCCGAGGATC AGAGCCTGTGAGGATGAAATGGGATAAGGTAGCTGGAACCGTC TGGCAGAGAGCGAGTCCTCAGGACTGTTGATGCCTGTGGCTGCC TGGCTTGACCCCAAGTGACCCCGCCTCCTCATCCTGCAGCAGGA GAA | Mouse; mm10: chr15: 78195347- 78196134 |
| 10 | TCTATAGAATGTGTCCCCAGCCTTGTTTTCCACACTTGATACGC AAGGAATGCATACCACAGAGAGGGATGAGGGTAGCATCCAGCC TGCTTCCTGTGTGTCGGGGCGCTACAGCCACATCTCCCCAGTCC ATCTCAGACCGTCACAGAGCTTCGCCGAATGTATAGCTTTGTTC TCTGTGCAGACAGGGAGACAGAGCCTTGGGAAGCATAGGTGCT TGCTTCTTTGCCCACTGAGTCTTAGCTGGACTTGCACACCACAT GCCTCACAGCCGGGCGCACTTGCATTTGTCACCCAGGCCCAGTG ATGATGGCTCTGCTTGCTTTGTGCTTTGTGCCAACTACAGCTCCA GCACCTGTGCCCTGGGTTTTCACTCCTTTAGTTGAACACGTAGTT ACTGGGGTTGTAGGGATGGAGCCTTTCTGCTTCCTTCTGGCAAA GTCCTTAGCGGCCTGCTGCGGGGGTGGGGGGTGTTCAGGGGAG TGGTGATGAAGTATGACAG | Mouse; mm10: chr15: 78196305- 78196806 |
| 11 | TCTCCAGTTGGAGAAACAGATGCTGTAACTGGGGCCACAGTAT AAAGAGAGCCCAGACATTGAACTGTCAACACAGAAGCCTGGCA CACTGGAACTGGCAGTCCAGCTGGGAACAAGGGGTAGAGGCTG AGGCCACTAAGTCAACTGAGGCAGGAGACATAGGAGCTAAAGC AGCTGAAGGGTGCAGGACAGCTGGGGGGTCTGAAGTGGGCCTC ATGCCCAGAGCTATGAAGTCAGGGGCTGTAGCCTAGGAGCCTT GGAAGCCAGCTGGCAAGCTGTGGCCCAAAGACGCTGACTCACC AGGAGGGGGCAGCTGGAGCCAGGCACTCCTAAGGTTTCCAGGA AGGGCAGCCTTCCAGGGCTCAGCTAGGGGAGACAGTGTTGACA GCAAGTTGTCAGGCAACTTGAGCTACTGGGCAGCTGGGAAGCT GTCCCTTGGTCCCCAGTATCATCATCACCCCAGACGCTGCCCAC CTGCCTCAGGTCCCACACAGTGATCCTCCCATCTTTAACACAAC ACATGACCAGAGAGA | Mouse; mm10: chr15: 78205234- 78205766 |
| 12 | GTCACCCTCCCCCCAAACAACCCCTTCTTCTCTGGTTCGAGAAA TTACAGGCATGAAAGATATAAATCGGGATGCTTGACTTGGGAA TATAAATCACTAAAGCTTGGGGGCAGGGGTGGGCGACCTTTGT GACCGTCCTTGTGCGTGCCAGTAAATCCTGTGGTCCAGGGGAGA AGAAAAGGCTGTGTGGCTTCTGCTCACAAAGCTGCAGAAACCA TTCTTTAAGCCCAAAAGCACTTCCAGAGAGAGCAGAGCATCCC CAGGCTGCTGGCTCAGCAAGTTCACTGTGCTCAATCTCAGGAAG TGAGGATAAGAGCAGTGCCTGGAGAGTGCCTGGTGCTGAGCTG AGGGTTTCTGAACACATTAAAGCGGGGAGCATGGACCGGGCCT CAGGAGGGGTGTTGAACATCCCTAGGCAGAGGAGTCTAGCTTC CTGGGAAAAGATATCAGGTTAAGCACACACATGTCCTCTGGAA TAAGATAATCTTTCTGATCACACACTATACACACAAAAGCCT GCTC | Mouse; mm10: chr15: 78224841- 78225364 |
| 13 | GCCCTCTAGGCCACCTGACCAGGTCCCCTCAGTCCCCCCCTTCC CACACTCCCACACTCAGCCCCCTCCCCCCCCCCGACCCCTGC AGGATTATCCTGTCTGTGTTCCTGACTCAGCCTGGGAGCCACCT GGGCAGCAGGGGCCAAGGGTGTCCTAGAAGGGACCTGGAGTCC ACGCTGGGCCAAGCCTGCCCTTTCTCCCTCTGTCTTCCGTCCCTG CTTGCGGTTCTGCTGAATGTGGTTATTTCTCTGGCTCCTTTTACA GAGAATGCTGCTGCTAATTTTATGTGGAGCTCTGAGGCAGTGTA ATTGGAAGCCAGACACCCTGTCAGCAGTGGGCTCCCGTCCTGA GCTGCCATGCTTCCTGCTCTCCTCCCGTCCCGGCTCCTCATTTCA TGCAGCCACCTGTCCCAGGGAGAGAGGAGTCACCCAGGCCCCT CAGTCCGCCCCTTAAATAAGAAAGCCTCCGTTGCTCGGCACACA TACCAAGCAGCCGCTGGTGCAATCT | Mouse; mm10:chr15: 78241348- 78241856 |

TABLE 1-continued

List of nucleic acid sequences disclosed herein.

| SEQ ID NO: | Nucleic Acid Sequence | Source/ Genomic Location |
| --- | --- | --- |
| 14 | GTGTTCTTCCCTTCCCCTTTGGACCCCCGAGACAAGCCAATAAA ATACTCGGCAGGGTGGCTTCTCTCCTTTTTTGCCAGTAATAAA CAGACTCAGAGCAAGTTAAGGGTCTGGTCCAAGGTCATGGCTG GGATCAGTGACAGAGCCCAGAAGAGAACCTGAGACTTCTTGCT GAGCCAAGCTGGAGAGGACAGAAAGGAATGCGTCTACTCCATG CATGACCCTCTGCCAGCTTTGCTCCTTCCTAAGGGACCATGAAC GATATGTGCACACCGCTCATACGTATGTGCACACCTGCAAGAG GAGGCATCCCATGTACACCTATGAGACGCACAGAGAAACATAT ATGTAGCCATAGGCTAGAAATTCTTTCTCTTTCTAGGTCTGCCCC TCTGCA | Mouse; mm10: chr9: 107340928- 107341325 |
| 15 | GGACCACTCAGTGTACACGGAATGTAGAATTGAGTCTGCCATTG GTCTTCCCTCAAAGTCTTGGAGGCTTGGGACTGATATTGGGAGC ATCTGGGCAGAGAAGGCCACAAAGACAGGGTGGTTTTTCTACA CTGGGACATACTCGTGAGCATGCACAGAGGCGTGTCCCCAACTT CCCTGTCACCCCTGTCCTCTGCCGGCTAGAGGGGATGCGGGGT GGACATATGCTGCTATTGGGCAGATATCACATGTTAAGAGGTGG GGGGGGCTCAAGAGGCGGAGGGCTAGGAGCATCCCATGGGG AGAGGTTCTGGTTTTCTTGCTGCCTCTAGCTGCTATAAATACGTT AGCACTTGAGCAACTGGAAAGCTCTGAGTAATTTAGGATGCAC AAAGCTGTAATTTAACTCCAGCATCTCAGTGTGCGAGAGCATTA AAGATGTAATTAAGATGTTTACACAAAGAGATTGGAGTCTGTG ACACTTGGGGTGCAAAACCCCAGGAAGGGACACAATGGGTGAG GTGAGGATCTGTGGGAGGCCTGGGACAGTCACTTGGATCCCA GCTATGAGATGGCAGGCCACCCAGCTGTTTCTCCTTGGAAATGT TTTGGCCTGGGGGTTGGGGTGGGCATCACACTTTGATATGGA GATGGGGCAACAAAGCCTGCAATATCTGGGGGTGGAGAGGTCA AGTGGATGGAGTCTTTTGAGATCATGTCAGGAAGAGGGCTCGA TCCCCCAAAATCATGGTGACATATGGTGTCTCGGGGTTCACAGG AGCTATGTCTAAAATACAAAAGTAAA | Mouse; mm10: chr9: 107349227- 107350036 |
| 16 | TCTGCAGAAGCCTGCCATTCCACCATTTAAACCTGTGACTCCAG GCCTTAAGCCTGTTGAAGGTCGAGTCCCAGAAGGGTCATATGTG CAACTGCCTAGGGAGAGTTCCCACTCGCAGGGCAAGAGGAGT CCCCCGGTCTGAGGTGTGGGGGCGGGGACGTGCACTGGGCGCT GGGACCACGGCTGGGGCTCAGGACTCGC | Mouse; mm10: chr9: 107399438- 107399639 |
| 17 | TGCCTCAGTTTCTTCGCCTAGAAAGCCGGGTCTAAGGGTACATG CCCTGATTCTTTTCTGGGGTGTCTCGAATTTTAAACAACACATA CTGTTCTGGGCTGATGACAAGAGGAAGTACTGGTCGGTGGCTG ATGGACATCCACCATGGTGGCAACTGGAGGGAGGGGGAACGGA CGTTGAAACCCTGCCCTCCTGGAATCTGTCGCATGCACGCACGT TGACAATGCTTGGCACTGGGGACAGGCTGGGATGGATGGAGCG GAGCGTGAGGAGGAGTGGGCATGCAGGCCCGAGTGTCTGTTTT GCTGATTGCTCCTTTTGCTTTCAAGGAGATTAAACTATTTTTAGT CCATGCCTACTGCTGGTGAGACGCTGGAGGAAGCCTTTCCATCG TTGAGATTTTCTGGAAGCTGCCAAGTGTGGTCTTCAGCTCAATT CTGGGAGCCTCCCAGAGTGGGAGGGAGGAACATTTCCATCTGG GGGCTTCGGGGACAGGCTAAGATCTTCCCTGGGGTCCTTGCTGC GCTGGCCTCCTCAAACCACGCTGCCTCGGCCTGCATAAAGCAGT AATCTGATGTGCCCGATGTTTGTAACGCTGTGTTTAAAAAAAGT AATTTATTTTCTAATTATTCCTTGTCTTGCATAACCATGCATTGC CAAAGTGTCGCTATTTAAAATATTTATCTCTCCACGCCGCAGGA GCAGCTCTGGAGCGTGGAGGGGGAAGAAATAAAAGTCCGCGTG CCAGTCGCAGGCATATTACTTTGACTCGTCCTGGTGGCTTTGAC GTCTCCCTGTAAATACATTTATTTTTCATTAGGACGTTTCTGAGC TTGTGGCCCCCGGAGAGCGGAGTGATTACGCTGTTCATCTGCAA GCGATGCAATAGAGGGGTACTCGCAGAATGACTTCCGCCCAGA GCATCCTGCGCCTGTCT | Mouse; mm10: chr9: 107443292- 107444228 |
| 18 | TAAAATACCTTATTTTTTTCCAGTCTCTAAACTGCTAATCTCCCA GGCTAAGGGATTCTGGGACAAAGGCAAGGCCTGGAAGTGGAAA TCTGTAAAATTAGCTTCAGCGGTATTAGTGTTTGCAGTTGAAGA TTGAAAAACTGCTTTCCCAGGGCCTGATTGGAGGCTCCACTCTC CTCCAGGAAGAGGCAAGGACTCTGGGCTGGCACTGAGGACAAA TCCTGGGAGGCTGCTATGGGGCCTGGGAGCCAGGCTGCCTTGTG CTAGAGGCTAGAGAGTGTCTGTGTCCCAAGTCCCAAGCTACCC CCAGCAGCTAACAGCTTTTCCAGTTCTCAGGCACAGCAGGTGCC AAGATCACGCTCTGGAGTCCAGCTGGGCCCCTTCCTCTTCTTTTT TTTTTTTTTTTTTAAGACCTCCTGGACACTGTTCCTCTCCCCCCC CCCGTGACCCCCCCCTCAGTTCTCAAACACGTGAGGGTTGGGG GAGGGTTCCACAGCCAGAGAGAGGGGCCAGCTCTGGTGCCTGT GGGTACGCCCGCCCGTATGGCCCATCAGGCCTCTTGTGTGCTTG ATTGCCTCTGATTGGCTGCAGCTGAATTCAGCAAAAGCTATTAT | Mouse; mm10: chr9: 107444825- 107445746 |

TABLE 1-continued

List of nucleic acid sequences disclosed herein.

| SEQ ID NO: | Nucleic Acid Sequence | Source/ Genomic Location |
|---|---|---|
|  | TTGCCCTTGATGAGCCAATCAGATGGCCTCATTGGCCATTCAGA GCAGGCACCGGAACCTGAGGGTGGGGTGGGGGGTGGGGGATG GAGATGGGACTCAGTGAGGGGGTGGGAAGCTCTAAAACAGATG CAGGACCTGAGCCTGTCTGTGTCCACCACGACCTTCACACAGGT CACACCCCCTTCCCCTGACTTGTCACCCCAAACCAGGGCTTGTT GCCCAACCCCACCTCACAATTCCCTCACTCTGTAACACCTTTCC ATATACCTCTGCATGTCTAAACCCAAGACTTGCTCTATGAAATC |  |
| 19 | AGACCCTGCTTAGCACAGCTCTTAGCGGGTCCTTTAGGGGTCT CCCAGCGGGCCCAGTGGGAATGAGATAAGGAAGGACACAGCTG TCCATTCTCCCGTGCCTGCTAAGGAGGAAATGGGGCCGCCTTAC ATAATTGGGGCAATTTGTTCCACTCTTGTCCTCCTGGTATCATGG CTATCACCCCCTCCTTGCTCAGGGAGTCCTTGATTGAGCGAGAA GCTCAGGCCTCCCTCTCTCCCTCCTGCTGGGGGTTGCTGAACAG AGGGTGTAGGAGCCATAGGCTCTGTCACTGCTGAGATCTGCCA GATGTCTAGGCCAGGAGAAAATGGAAAGGGCTAAGTCACAGCA TATGTGGCCACTCAGGCCTATAGCCCCAAATCTGCCTGGTAACC CATTATGTCCCCAGAGAATTTGCATGGGCGGACACCCTCATGCC GGGTCTCAGTAAGGGAAGGGGTGGGAGGCAAAAATATCCCTCC CCACCCTGAATCTCCACCCCCTCCCCCCAGAAACTGACACTTGG CCTTGTCTAAGGATGGGTTTTCCCAAAATCCTTCTGAAAAAAAC AGAATTTCAAGAGTCACTCCCTCCGGGTCTCAGCCTAGAACATA TGCAGTATCCCCTGACGTCCATAGGG | Mouse; mm10: chr9: 107452080- 107452718 |
| 20 | AAACTGGCACAGTAATGGCGGGCTGACAGACAAGGGAGTCTGT AGCACCCGCTGCCTCCGCCCACCCCTTCTCCGAGCAATTAAAAG GTGTTTATGTGGGGCTGGCAGTGGCTTCTGCCTCCCTTCCATTAC GAACATTAAGAGATCTTGACCCTTCCACTTTCCCCGCTCTTGAA AGGAGCTGCAGACACGTGGAGCCAATTAGGCGCACGCGTGGGC GCCAAGGGCCTGAGCAGCTTTTTCTCCCTGATTGCGGCGTTTAC AGCTGATTATTCTCCCCTCACCCAAACAGTGCTGCTTCCTGGCA AGGTGCCACCCAGAGGAGCCGGCTGGGGGCCCCTGGGGACAGG GGAGGACTGGATTAGTAAATGGGCATCTATCGAATGGCTTTCAT ATGTGTGGCTGGAAGGGAGAAGGGTAGGGCCAGGAATGGTGGC AGCAAGGGCCCAGGTAGCAATGAGGGTTCTTCTAACCCACCAT TTAGGGATAGCGATCAGAAAAGGGCCCTCGAGGAGGTGACCTA AATGTGTGTAGAAGCTGACGGCCACTACACACACACACACACA CACACACACACATACACAAGCATCCTTGTCCTTGGAGTCGGTCA GCATGAGCAAGAGAAAGATGTTCCCAGTGGCCATGAGAGTGGA GCCCTCCTCCCTACTTACATCCAGGTTGGATGGCCAGGAGATCC TGAGATCCTTCAAGACTCC | Mouse; mm10: chr9: 107470414- 107471129 |
| 21 | AAGCCACATCCTGGGTGGAAATATATGGCTTCAATTCCCACTCT TCCGGATGACCTCTGTGGGGAGCCCTGGCTTCACCTTGGTCAG CTTCATCCCTTAGCCTCGCTGCCAGGAAGGCAGTGAGGTCAGAG GCTGGTGCTGGCGTG | Mouse; mm10: chr9: 107484887- 107485033 |
| 22 | CCTACCTGGTGCCCGCCAACATCTGGGGGCCATCCTGGCCAGCG CCAGCGTGGTGGTGAAGGCACTGTGCGCCGTGGTACTGTTTCTC TACCTGCTTTCCTTCGCTGTGGACACGGGCTGCCTGGCCGTCAC CCCAGGCTACCTTTTCCCACCCAACTTCTGGATCTGGACCCTGG CCACCCACGGGCTCATGGAACAGCACGTGTGGGACGTGGCCAT TAGCCTGGCCACAGTGGTTGTGGCCGGGCGATTACTGGAGCCCC TCTGGGGAGCCTTGGAGCTGCTCATCTTCTTCTC | Mouse; mm10: chr9: 107534490- 107534786 |
| 23 | AAACGGACGGGCCTCCGCTGAACCAGTGAGGCCCCAGACGTGC CTGGGGAGAGGGGGGCATAAATAACCCCTGCGTGCTGCACCAC AGGACCACGGTAAAT | Human; hg19: chr2: 171672063- 171672163 |
| 24 | GGAGCGAGCGCATAGCAAAAGGGACGCGGGGTCCTTTTCTCTG CCGGTGGCACTGGGTAGCTGTGCCAGGTGTGGTACTTTGATGG GGCCCAGGGCTGGA | Human; hg19: chr2: 171672697- 171672797 |
| 25 | GCTCAAGGAAGCGTCGCAGGGTCACAGATCTGGGGGAACCCCG GGGAAAAGCACTGAGGCAAAACCGCCGCTCGTCTCCTACAATA TATGGGAGGGGAGG | Human; hg19: chr2: 171672918- 171673018 |

TABLE 1-continued

List of nucleic acid sequences disclosed herein.

| SEQ ID NO: | Nucleic Acid Sequence | Source/ Genomic Location |
|---|---|---|
| 26 | TTGAGTACGTTCTGGATTACTCATAAGACCTTTTTTTTTCCTTC CGGGCGCAAAACCGTGAGCTGGATTTATAATCGCCCTATAAAG CTCCAGAGGCGGTCAGGCACCTGCAGAGGAGCCCCGCCGCTCC GCCGACTAGCTGCCCCCGCGAGCAACGGCCTCGTGATTTCCCCG CCGATCCGGTCCCCGCCTCCCCACTCTGCCCCCGCCTACCCCGG AGCCGTGCAGCCGCCTCTCCGAATCTCTCTCTTCTCCTGGCGCTC GCGTGCGAGAGGGAACTAGCGAGAACGAGGAAGCAGCTGGAG GTGACGCCGGGCAGATTACGCCTGTCAGGGCCGAGCCGAGCGG ATCGCTGGGCGCTGTGCAGAGGAAAGGCGGGAGTGCCCGGCTC GCTGTCGCAGAGCCGAGGTGGGTAAGCTAGCGACCACCTGGAC TTCCCAGCGCCCAACCGTGGCTTTTCAGCCAGGTCCTCTCCTCC CGCGGCTTCTCAACCAACCCCATCCCAGCGCCGGCCACCCAACC TCCCGAAATGAGTGCTTCCTGCCC | Human; hg19: chr2: 171673150- 171673696 |
| 27 | CAGCAGCCGAAGGCGCTACTAGGAACGGTAACCTGTTACTTTTC CAGGGGCCGTAGTCGACCCGCTGCCCGAGTTGCTGTGCGACTGC GCGCGCGGGGCTA | Human; hg19: chr2: 171673900- 171674000 |
| 28 | GAGTGCAAGGTGACTGTGGTTCTTCTCTGGCCAAGTCCGAGGGA GAACGTAAAGATATGGGCCTTTTTCCCCCTCTCACCTTGTCTCA CCAAAGTCCCTAGTCCCCGGAGCAGTTAGCCTCTTTCTTTCCAG GGAATTAGCCAGACACAACAACGGGAACCAGACACCGAACCA GACATGCCCGCCCCGTGCGCCCTCCCC | Human; hg19: chr2: 171674400- 171674600 |
| 29 | GCTCGCTGCCTTTCCTCCCTCTTGTCTCTCCAGAGCCGGATCTTC AAGGGGAGCCTCCGTGCCCCGGCTGCTCAGTCCCTCCGGTGTG CAGGACCCCGGAAGTCCTCCCCGCACAGCTCTCGCTTCTCTTTG CAGCCTGTTTCTGCGCCGGACCAGTCGAGGACTCTGGACAGTAG AGGCCCCGGGACGACCGAGCTG | Human; hg19: chr2: 171674903- 171675101 |
| 30 | AAACGGACGGGCCTCCGCTGAACCAGTGAGGCCCCAGACGTGC GCATAAATAACCCCTGCGTGCTGCACCACCTGGGGAGAGGGGG AGGACCACGGTAAATGGAGCGAGCGCATAGCAAAAGGGACGC GGGGTCCTTTTCTCTGCCGGTGGCACTGGGTAGCTGTGGCCAGG TGTGGTACTTTGATGGGGCCCAGGGCTGGAGCTCAAGGAAGCG TCGCAGGGTCACAGATCTGGGGGAACCCCGGGGAAAAGCACTG AGGCAAAACCGCCGCTCGTCTCCTACAATATATGGGAGGGGGA GGTTGAGTACGTTCTGGATTACTCATAAGACCTTTTTTTTTTCCT TCCGGGCGCAAAACCGTGAGCTGGATTTATAATCGCCCTATAAA GCTCCAGAGGCGGTCAGGCACCTGCAGAGGAGCCCCGCCGCTC CGCCGACTAGCTGCCCCCGCGAGCAACGGCCTCGTGATTTCCCC GCCGATCCGGTCCCCGCCTCCCCACTCTGCCCCCGCCTACCCCG GAGCCGTGCAGCCGCCTCTCCGAATCTCTCTCTTCTCCTGGCGC TCGCGTGCGAGAGGGAACTAGCGAGAACGAGGAAGCAGCTGG AGGTGACGCCGGGCAGATTACGCCTGTCAGGGCCGAGCCGAGC GGATCGCTGGGCGCTGTGCAGAGGAAAGGCGGGAGTGCCCGGC TCGCTGTCGCAGAGCCGAGGTGGGTAAGCTAGCGACCACCTGG ACTTCCCAGCGCCCAACCGTGGCTTTTCAGCCAGGTCCTCTCCT CCCGCGGCTTCTCAACCAACCCCATCCCAGCGCCGGCCACCCAA CCTCCCGAAATGAGTGCTTCCTGCCCCAGCAGCCGAAGGCGCTA CTAGGAACGGTAACCTGTTACTTTTCCAGGGGCCGTAGTCGACC CGCTGCCCGAGTTGCTGTGCGACTGCGCGCGCGGGGCTAGAGT GCAAGGTGACTGTGGTTCTTCTCTGGCCAAGTCCGAGGGAGAA CGTAAAGATATGGGCCTTTTTCCCCCTCTCACCTTGTCTCACCAA AGTCCCTAGTCCCCGGAGCAGTTAGCCTCTTTCTTTCCAGGGAA TTAGCCAGACACAACAACGGGAACCAGACACCGAACCAGACAT GCCCGCCCCGTGCGCCCTCCCCGCTGCTGCCTTTCCTCCCTCTT GTCTCTCCAGAGCCGGATCTTCAAGGGGAGCCTCCGTGCCCCCG GCTGCTCAGTCCCTCCGGTGTGCAGGACCCCGGAAGTCCTCCCC GCACAGCTCTCGCTTCTCTTTGCAGCCTGTTTCTGCGCCGGACC AGTCGAGGACTCTGGACAGTAGAGGCCCCGGGACGACCGAGCT G | Human |
| 31 | GGAGGAAGCCATCAACTAAACTACAATGACTGTAAGATACAAA ATTGGGAATGGTAACATATTTTGAAGTTCTGTTGACATAAAGAA TCATGATATTAATGCCCATGGAAATGAAAGGGCGATCAACACT ATGGTTTGAAAAGGGGGAAATTGTAGAGCACAGATGTGTTCGT GTGGCAGTGTGCTGTCTCTAGCAATACTCAGAGAAGAGAGAGA ACAATGAAATTCTGATTGGCCCCAGTGTGAGCCCAGATGAGGTT CAGCTGCCAACTTTCTCTTTCACATCTTATGAAAGTCATTTAAGC ACAACTAACTTTTTTTTTTTTTTTTTTTTTGAGACAGAGTCTTG CTCTGTTGCCCAGGACAGAGTGCAGTAGTGACTCAATCTCGGCT | Human |

TABLE 1-continued

List of nucleic acid sequences disclosed herein.

| SEQ ID NO: | Nucleic Acid Sequence | Source/ Genomic Location |
|---|---|---|
|  | CACTGCAGCCTCCACCTCCTAGGCTCAAACGGTCCTCCTGCATC<br>AGCCTCCCAAGTAGCTGGAATTACAGGAGTGGCCCACCATGCC<br>CAGCTAATTTTTGTATTTTTAATAGATACGGGGGTTTCACCATAT<br>CACCCAGGCTGGTCTCGAACTCCTGGCCTCAAGTGATCCACCTG<br>CCTCGGCCTCCCAAAGTGCTGGGATTATAGGCGTCAGCCACTAT<br>GCCCAACCCGACCAACCTTTTTTAAAATAAATATTTAAAAAATT<br>GGTATTTCACATATATACTAGTATTTACATTTATCCACACAAAA<br>CGGACGGGCCTCCGCTGAACCAGTGAGGCCCCAGACGTGCGCA<br>TAAATAACCCCTGCGTGCTGCACCACCTGGGGAGAGGGGGAGG<br>ACCACGGTAAATGGAGCGAGCGCATAGCAAAAGGGACGCGGG<br>GTCCTTTTCTCTGCCGGTGGCACTGGGTAGCTGTGTGGCCAGGTGT<br>GGTACTTTGATGGGGCCCAGGGCTGGAGCTCAAGGAAGCGTCG<br>CAGGGTCACAGATCTGGGGGAACCCCGGGGAAAAGCACTGAGG<br>CAAAACCGCCGCTCGTCTCCTACAATATATGGGAGGGGGAGGT<br>TGAGTACGTTCTGGATTACTCATAAGACCTTTTTTTTTTCCTTCC<br>GGGCGCAAAACCGTGAGCTGGATTTATAATCGCCCTATAAAGC<br>TCCAGAGGCGGTCAGGCACCTGCAGAGGAGCCCCGCCGCTCCG<br>CCGACTAGCTGCCCCCGCGAGCAACGGCCTCGTGATTTCCCCGC<br>CGATCCGGTCCCCGCCTCCCCACTCTGCCCCCGCCTACCCCGGA<br>GCCGTGCAGCCGCCTCTCCGAATCTCTCTCTTCTCCTGGCGCTCG<br>CGTGCGAGAGGGAACTAGCGAGAACGAGGAAGCAGCTGGAGG<br>TGACGCCGGGCAGATTACGCCTGTCAGGGCCGAGCCGAGCGGA<br>TCGCTGGGCGCTGTGCAGAGGAAAGGCGGGAGTGCCCGGCTCG<br>CTGTCGCAGAGCCGAGGTGGGTAAGCTAGCGACCACCTGGACT<br>TCCCAGCGCCCAACCGTGGCTTTTCAGCCAGGTCCTCTCCTCCC<br>GCGGCTTCTCAACCAACCCCATCCCAGCGCCGGCCACCCAACCT<br>CCCGAAATGAGTGCTTCCTGCCCCAGCAGCCGAAGGCGCTACT<br>AGGAACGGTAACCTGTTACTTTTCCAGGGGCCGTAGTCGACCCG<br>CTGCCCGAGTTGCTGTGCGACTGCGCGCGCGGGGCTAGAGTGC<br>AAGGTGACTGTGGTTCTTCTCTGGCCAAGTCCGAGGGAGAACGT<br>AAAGATATGGGCCTTTTTCCCCCTCTCACCTTGTCTCACCAAAG<br>TCCCTAGTCCCCGGAGCAGTTAGCCTCTTTCTTTCCAGGGAATT<br>AGCCAGACACAACAACGGGAACCAGACACCGAACCAGACATG<br>CCCGCCCCGTGCGCCTCCCCGCTCGCTGCCTTTCCTCCCTCTTG<br>TCTCTCCAGAGCCGGATCTTCAAGGGGAGCCTCCGTGCCCCCGG<br>CTGCTCAGTCCCTCCGGTGTGCAGGACCCCGGAAGTCCTCCCCG<br>CACAGCTCTCGCTTCTCTTTGCAGCCTGTTTCTGCGCCGGACCA<br>GTCGAGGACTCTGGACAGTAGAGGCCCCGGGACGACCGAGCTG |  |
| 32 | TCAACAGGGGACACTTGGGAAAGAAGGATGGGGACAGAGCC<br>GAGAGGACTGTTACACATTAGAGAAACATCAGTGACTGTGCCA<br>GCTTTGGGGTAGACTGCACAAAAGCCCTGAGGCAGCACAGGCA<br>GGATCCAGTCTGCTGGTCCCAGGAAGCTAACCGTCTCAGACAG<br>AGCACAAAGCACCGAGACATGTGCCACAAGGCTTGTGTAGAGA<br>GGTCAGAGGACAGCGTACAGGTCCCAGAGATCAAACTCAACCT<br>CACCCAGGCTTGGCAGCAAGCCTTTACCAACCCACCCCCACCCCA<br>CCCACCCTGCACGCGCCCCTCTCCCCTCCCCATGGTCTCCCATG<br>GCTATCTCACTTGGCCCTAAAATGTTTAAGGATGACACTGGCTG<br>CTGAGTGGAAATGAGACAGCAGAAGTCAACAGTAGATTTTAGG<br>AAAGCCAGAGAAAAGGCTTGTGCTGTTTTAGAAAGCCAAGG<br>GACAAGCTAAGATAGGGCCCAAGTAATGCTAGTATTTACATTTA<br>TCCACACAAAACGGACGGGCCTCCGCTGAACCAGTGAGGCCCC<br>AGACGTGCGCATAAATAACCCCTGCGTGCTGCACCACCTGGGG<br>AGAGGGGGAGGACCACGGTAAATGGAGCGAGCGCATAGCAAA<br>AGGGACGCGGGGTCCTTTTCTCTGCCGGTGGCACTGGGTAGCTG<br>TGGCCAGGTGTGGTACTTTGATGGGGCCCAGGGCTGGAGCTCA<br>AGGAAGCGTCGCAGGGTCACAGATCTGGGGGAACCCCGGGGAA<br>AAGCACTGAGGCAAAACCGCCGCTCGTCTCCTACAATATATGG<br>GAGGGGGAGGTTGAGTACGTTCTGGATTACTCATAAGACCTTTT<br>TTTTTTCCTTCCGGGCGCAAAACCGTGAGCTGGATTTATAATCG<br>CCCTATAAAGCTCCAGAGGCGGTCAGGCACCTGCAGAGGAGCC<br>CCGCCGCTCCGCCGACTAGCTGCCCCCGCGAGCAACGGCCTCGT<br>GATTTCCCCGCCGATCCGGTCCCCGCCTCCCCACTCTGCCCCCG<br>CCTACCCCGGAGCCGTGCAGCCGCCTCTCCGAATCTCTCTCTTC<br>TCCTGGCGCTCGCGTGCGAGAGGGAACTAGCGAGAACGAGGAA<br>GCAGCTGGAGGTGACGCCGGGCAGATTACGCCTGTCAGGGCCG<br>AGCCGAGCGGATCGCTGGGCGCTGTGCAGAGGAAAGGCGGGA<br>GTGCCCGGCTCGCTGTCGCAGAGCCGAGGTGGGTAAGCTAGCG<br>ACCACCTGGACTTCCCAGCGCCCAACCGTGGCTTTTCAGCCAGG<br>TCCTCTCCTCCCGCGGCTTCTCAACCAACCCCATCCCAGCGCCG<br>GCCACCCAACCTCCCGAAATGAGTGCTTCCTGCCCCAGCAGCCG<br>AAGGCGCTACTAGGAACGGTAACCTGTTACTTTTCCAGGGGCCG<br>TAGTCGACCCGCTGCCCGAGTTGCTGTGCGACTGCGCGCGCGGG<br>GCTAGAGTGCAAGGTGACTGTGGTTCTTCTCTGGCCAAGTCCGA | Human and mouse |

TABLE 1-continued

List of nucleic acid sequences disclosed herein.

| SEQ ID NO: | Nucleic Acid Sequence | Source/ Genomic Location |
|---|---|---|
|  | GGGAGAACGTAAAGATATGGGCCTTTTTCCCCCTCTCACCTTGT CTCACCAAAGTCCCTAGTCCCCGGAGCAGTTAGCCTCTTTCTTT CCAGGGAATTAGCCAGACACAACAACGGGAACCAGACACCGA ACCAGACATGCCCGCCCCGTGCGCCCTCCCCGCTCGCTGCCTTT CCTCCCTCTTGTCTCTCCAGAGCCGGATCTTCAAGGGGAGCCTC CGTGCCCCCGGCTGCTCAGTCCCTCCGGTGTGCAGGACCCCGGA AGTCCTCCCCGCACAGCTCTCGCTTCTCTTTGCAGCCTGTTTCTG CGCCGGACCAGTCGAGGACTCTGGACAGTAGAGGCCCCGGGAC GACCGAGCTG |  |
| 33 | ATTTACATTTATCCACACA | Human |
| 34 | TGCCGCTGGACTCTCTTCCAAGGAACTAGGAGAACCAAGATCC GTTTTTCTGCCAAGGGCTGCCCCCCCCACGCCCCCAACCCCCTC ACCCCGATCCCCACAGAAAGAAATCTTGAGGTAGCTGGAGCTT CTTCTGTGGGTGTGACAGGACTGCCATTCTCCTCTGTAGTCTGC AGAAGCCTGCCATTCCACCATTTAAACCTGTGACTCCAGGCCTT AAGCCTGTTGAAGGTCGAGTCCCAGAAGGGTCATATGTGCAAC TGCCTAGGGAGAGTTCCCACTCGCAGGGCCAAGAGGAGTCCCC CGGTCTGAGGTGTGGGGGCGGGACGTGCACTGGGCGCTGGGA CCACGGCTGGGGCTCAGGACTCGCGAGCTTGGATTCGGATCGG TTTGCGCGAGCCAGTAGGGCAGGCTCCGGGGTGAACGGGGACG AGGGGCGCGCGGGCACAGGCGGGCGCGTGACCGCGGCGGGGG CGCGCGGAGGCGGGCCGGCCAAGGAGAGGGAGGGAGGGAATG AGGGAGGGAGCGACAGGGGAGGGCGGCGCCGGCAGGTTGGCG GCGGCCGCTATTTGAGCGCAGGTCCCGGGCCAGGCGCTCAAAG CGCTTGGAGCCAGCGCGGCGGGGAGATCGCTGCGCGCAGCCCG CAGAGGCGCTGCGCCAGTGCAGCCCCGGAGGCCCCGCGCGGA GAAGGAGGTGGAGAAGAGGCCGGCTTTTCGCCCGCCGCCCGCG CCCCCCCACCTCCATCCCGCCGCCGCCGTCCCCCCTCCCTCCCC GCGGCGCCGCATCTTGAATGGAAAC | Mouse; chr9: 107,399,268- 107,400,067 |
| 35 | GAGTAATTCATACAAAAGGACTCGCCCCTGCCTTGGGGAATCCC AGGGACCGTCGTTAAACTCCCACTAACGTAGAACCCAGAGATC GCTGCGTTCCCGCCCCCTCACCCGCCCGCTCTCGTCATCACTGA GGTGGAGAAGAGCATGCGTGAGGCTCCGGTGCCCGTCAGTGGG CAGAGCGCACATCGCCCACAGTCCCCGAGAAGTTGGGGGGAGG GGTCGGCAATTGAACCGGTGCCTAGAGAAGGTGGCGCGGGGTA AACTGGGAAAGTGATGTCGTGTACTGGCTCCGCCTTTTTCCCGA GGGTGGGGGAGAACCGTATATAAGTGCAGTAGTCGCCGTGAAC GTTCTTTTTCGCAACGGGTTTGCCGCCAGAACACAGGTAAGTGC CGTGTGTGGTTCCCGCGGGCCTGGCCTCTTTACGGGTTATGGCC CTTGCGTGCCTTGAATTACTTCCACGCCCCTGGCTGCAGTACGT GATTCTTGATCCCGAGCTTCGGGTTGGAAGTGGGTGGGAGAGTT CGAGGCCTTGCGCTTAAGGAGCCCCTTCGCCTCGTGCTTGAGTT GAGGCCTGGCTTGGGCGCTGGGGCCGCCGCGTGCGAATCTGGT GGCACCTTCGCGCCTGTCTCGCTGCTTTCGATAAGTCTCTAGCC ATTTAAAATTTTTGATGACCTGCTGCGACGCTTTTTTTCTGGCAA GATAGTCTTGTAAATGCGGGCCAAGATCTGCACACTGGTATTTC GGTTTTTGGGGCCGCGGGCGGCGACGGGGCCCGTGCGTCCCAG CGCACATGTTCGGCGAGGCGGGGCCTGCGAGCGCGGCCACCGA GAATCGGACGGGGGTAGTCTCAAGCTGGCCGGCCTGCTCTGGT GCCTGGCCTCGCGCCGCCGTGTATCGCCCCGCCCTGGGCGGCAA GGCTGGCCCGGTCGGCACCAGTTGCGTGAGCGGAAAGATGGCC GCTTCCCGGCCCTGCTGCAGGGAGCTCAAAATGGAGGACGCGG CGCTCGGGAGAGCGGGCGGGTGAGTCACCCACACAAAGGAAA AGGGCCTTTCCGTCCTCAGCCGTCGCTTCATGTGACTCCACGGA GTACCGGGCGCCGTCCAGGCACCTCGATTAGTTCTCGAGCTTTT GGAGTACGTCGTCTTTAGGTTGGGGGAGGGGTTTTATGCGATG GAGTTTCCCCACACTGAGTGGGTGGAGACTGAAGTTAGGCCAG CTTGGCACTTGATGTAATTCTCCTTGGAATTTGCCCTTTTTGAGT TTGGATCTTGGTTCATTCTCAAGCCTCAGACAGTGGTTCAAAGT TTTTTTCTTCCATTTCAGGTGTCGTGA |  |

In one aspect, regulatory elements disclosed herein are cell-type selective. In some cases, regulatory elements disclosed herein are selective for PV neurons. In some cases, regulatory elements disclosed herein are selective for PV neurons in the CNS. In some cases, PV-cell selective regulatory elements or any regulatory elements disclosed herein can result in selective gene expression in PV neurons over at least one, two, three, four, five, or more non-PV CNS cell-types.

In some cases, any one or more of the regulatory elements disclosed herein are operably linked to a transgene in an expression cassette to result in selective expression in a target cell-type, e.g., a PV neuron. In some cases, a regulatory element of any of the embodiments herein comprises or consists of any one of (i) SEQ ID NOs: 1-33; (ii) a variant, functional fragment, or a combination thereof; or (iii) a sequence having at least 80%, at least 85%, at least 90%, at least 91%, at least 92%, at least 93%, at least 94%, at least 95%, at least 96%, at least 97%, at least 98%, at least 99%, or 100% sequence identity to any one of (i) or (ii). In some cases, a regulatory element comprises any one of SEQ ID NOs: 1-32. In some cases, sequence identity is measured by BLAST.

In some cases, two or more, three or more, four or more, five or more, six or more, seven or more, eight or more, nine or more, or ten or more of SEQ ID NOs: 1-32, or a functional fragment or a combination thereof, or sequences having at least 80%, at least 90%, at least 95%, or at least 99% sequence identity thereto, are combined to form a larger regulatory element, or are operably linked to a gene in an expression cassette. In some cases, two or more, three or more, four or more, five or more, six or more, seven or more, eight or more, nine or more, or ten or more of SEQ ID NOs: 1-32, or a functional fragment or a combination thereof, or sequences having at least 80%, at least 90%, at least 95%, or at least 99% sequence identity thereto, are combined using a linker sequence of 1-50 nucleotides. In some cases, two or more, three or more, four or more, five or more, six or more, seven or more, eight or more, nine or more, or ten or more of SEQ ID NOs: 1-32, or a functional fragment or a combination thereof, or sequences having at least 80%, at least 90%, at least 95%, or at least 99% sequence identity thereto, are combined without a linker sequence. In some cases, a sequence of SEQ ID NO: 33 is used as a linker between any two regulatory elements. In some cases, a linker sequence between any two regulatory elements comprises SEQ ID NO: 33 or a sequence having at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 33. In some cases, sequence identity is measured by BLAST.

In some cases, when two or more regulatory elements are combined or used in an expression cassette, the regulatory elements need not be adjacent or linked in an expression cassette. For example, one regulatory element can be located upstream of a transgene, while a second regulatory element and/or additional regulatory elements can be located downstream of the transgene. In some cases, one or more regulatory elements can be located upstream of a transgene. In some cases, one or more regulatory elements can be located downstream of a transgene.

In some cases, any one or more of SEQ ID NOs: 1-22, or a functional fragment or a combination thereof, or sequences having at least 80%, at least 90%, at least 95%, or at least 99% sequence identity thereto, can be combined with any one or more of SEQ ID NO: 23-30, or a functional fragment or a combination thereof, or sequences having at least 80%, at least 90%, at least 95%, or at least 99% sequence identity thereto, to form a larger regulatory element. For example, a regulatory element comprises SEQ ID NO: 1 and SEQ ID NO: 30. A regulatory element comprises SEQ ID NO: 8 and SEQ ID NO: 30. A regulatory element comprises SEQ ID NO: 1 and SEQ ID NOs: 23-29. A regulatory element comprises SEQ ID NO: 8 and SEQ ID NOs: 23-29. In some cases, a regulatory element comprises SEQ ID NO: 30 or any one or more of SEQ ID NOs: 23-29, or a functional fragment or a combination thereof, or sequences having at least 80%, at least 90%, at least 95%, or at least 99% sequence identity thereto.

In some cases, one or more regulatory elements of the present disclosure result in selective gene expression in a PV cell. In some cases, regulatory elements that show selective activity or function in a target cell type also show minimal activity or function in one or more off-target cell-types, e.g., non-PV CNS cell-types, non-inhibitory neurons or excitatory neurons, non-PV cells.

In some cases, one or more regulatory elements operably linked to a gene modulates gene expression in a cell, including but not limited to, selective expression in a target cell-type over non-target cell-types. Selective expression in a target cell or cell type can also be referred to as cell-selective expression or cell-type selective expression.

Selective expression generally refers to expression in a high fraction of cells of the cell type of interest (or the target cell type) as compared to other cells (or non-target cell type). Selective expression can also be viewed as preferential expression in a target cell or target cell type over one or more non-target cells or cell-types. In some cases, selective expression of one or more regulatory elements of this disclosure is compared to CAG, EF1α, a constitutive promoter (e.g., SV40, CMV, UBC, PGK, and CBA), or a non-selective regulatory element that is known to drive expression in any cell or cell type without selectivity. In some cases, selective expression of one or more regulatory elements of this disclosure is compared to CAG, EF1α, a constitutive promoter (e.g., SV40, CMV, UBC, PGK, and CBA), a non-selective regulatory element, or an expression cassette without the regulatory elements.

Non-target cell types can include a different subset, subtype, or type of cells as compared to the target cell or target cell type, or all non-target cell types. In some cases, one or more regulatory elements operably linked to a gene result in selective expression in a target cell type over at least one type of non-target cells, or at least two, at least three, at least four, at least five, or more than five types of non-target cells. In some cases, non-target cell types refer to all other cell types not including the target cell type. In some cases, non-target cell types are all other cell types within a relevant tissue or organ not including the target cell type, e.g., all non-target cell types in the CNS, all non-target cell types in the hippocampus. In some cases, a non-target cell or non-target cell type encompasses a subset or subtype of cells that is not the target cell. For example, non-PV CNS cell-types can include GABAergic cells that express calretinin and/or somatostatin instead of parvalbumin, or all GABAergic cells that do not express parvalbumin. In some cases, cell types are distinguished by having a different cell marker, morphology, phenotype, genotype, function, and/or any other means for classifying cell types.

Selectivity of expression driven by a regulatory element in a cell or cell type of interest can be measured in a number of ways. Selectivity of gene expression in a target cell type over non-target cell types can be measured by comparing the number of target cells that express a detectable level of a transcript from a gene that is operably linked to one or more regulatory elements to the total number of cells that express the gene. Such measurement, detection, and quantification can be done either in vivo or in vitro.

In some instances, selectivity for PV neurons can be determined using a co-localization assay. In some cases, the co-localization assay is based on immunohistochemistry. In some cases, a detectable reporter gene is used as a transgene to allow the detection and/or measurement of gene expression in a cell. In some cases, a detectable marker, e.g., a fluorescent marker or an antibody, which specifically labels the target cell is used to detect and/or measure the target cells. In some cases, a co-localization assay employs imaging, e.g., fluorescent imaging, to determine the overlap between different fluorescent labels, e.g., overlap between a fluorescence signal indicative of a target cell and another fluorescence signal indicative of gene expression. In some cases, fluorescent labels used for a co-localization assay include a red fluorescent protein (RFP), such as a tdTomato reporter gene, and a green fluorescent reporter protein, such as eGFP.

In some instances, a gene operably linked to one or more regulatory elements is a fluorescent protein, e.g., eGFP or RFP, wherein expression of the transgene provides a detectable signal. In some cases, tissue is stained for eGFP or fluorescence from eGFP is detected directly using a fluorescence microscope. A second fluorescent marker or reporter gene having a different fluorescence or detectable signal can be used to indicate the target cells, such as an antibody that identifies the target cells. For example, an anti-PV antibody that interacts specifically with PV neurons can be used to yield a detectable signal that is distinguishable from the fluorescence used to measure gene expression, such as a red fluorescence or a red stain. Thus, in an example wherein eGFP is a transgene operably linked to one or more regulatory elements that drive selective expression in PV neurons, and wherein the PV neurons are labeled with an anti-PV antibody, selectivity of gene expression in PV cells is measured as percentage of eGFP+ cells that are also PV+. In such assay, PV+ cells that are also eGFP+ are indicated by the overlap of both fluorescence signals, i.e., an overlap of the red and green fluorescence. Such measurement, analysis, and/or detection can be done by eye inspection or by a computer.

In some cases, one can also measure the proportion of a cell type of interest (or target cell type) that expresses a transgene as compared to the proportion of non-target cell types (or other cells) that express the transgene to assess the selectivity of one or more regulatory elements operably linked to the transgene. Similarly, selectivity of expression can also be measured by comparing the number of target cells that express a transgene operably linked to one or more regulatory elements to the total number of all cells that express the transgene. In both approaches, the higher the number of target cells that express the transgene, the more selective are the regulatory elements for the target cells. In some cases, the target cells are PV neurons.

In some cases, one or more regulatory elements disclosed herein result in increased selectivity in gene expression in a PV neuron. In some cases, one or more regulatory elements disclosed herein result in increased selectivity in gene expression in PV neurons as compared to non-PV CNS cell-types. In some cases, one or more regulatory elements disclosed herein result in increased selectivity in gene expression in PV neurons as compared to non-PV GABAergic cells, wherein non-PV GABAergic cells can be any one or more of GABAergic cells that express calretinin (CR), somatostatin (SOM), cholecystokinin (CCK), neuropeptide Y (NPY), vasointestinal polypeptide (VIP), choline acetyltransferase (ChAT), or a combination thereof. In some cases, one or more regulatory elements disclosed herein result in increased selectivity in gene expression in PV neurons as compared to at least one, at least two, at least three, at least four, at least five, or more than five non-PV GABAergic subtypes. In some cases, one or more regulatory elements disclosed herein result in increased selectivity in gene expression in PV neurons as compared to all other non-PV GABAergic cells, or all other GABAergic cells that do not express PV, or all other CNS cells that do not express PV, or all other neurons that do not express PV. In some cases, one or more regulatory elements disclosed herein result in increased selectivity in gene expression in PV neurons as compared to all non-PV cells in the CNS or all non-PV neurons.

In some cases, one or more regulatory elements operably linked to a transgene result in selective expression of the transgene in PV cells, wherein the percentage of PV cells expressing the transgene is at a percentage higher than gene expression in PV cells wherein the transgene is operably linked to CAG, EF1α, a constitutive promoter (e.g., SV40, CMV, UBC, PGK, and CBA), or a non-selective regulatory element, such as SEQ ID NO: 34, or a functional fragment thereof, or a sequence having at least 80% sequence identity thereto. In some cases, one or more regulatory elements result in selective expression in PV neurons at a level that is at least 1.5 fold, at least 2 hold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, or at least 50 fold as compared to expression of a gene operably linked to CAG, EF1α, a constitutive promoter (e.g., SV40, CMV, UBC, PGK, and CBA), or a non-selective regulatory element such as SEQ ID NO: 34, or a functional fragment thereof, or a sequence having at least 80%, at least 85%, at least 90%, at least 95%, or at least 99% sequence identity thereto.

In some aspects, a regulatory element is human derived or comprises a sequence that is human derived. In some cases, a regulatory element is mouse derived or comprises a sequence that is mouse derived. In some cases, a regulatory element comprises a non-naturally occurring sequence. In some cases, a regulatory element is non-naturally occurring. In some cases, one or more human derived regulatory elements are combined with another regulatory element to generate a non-naturally occurring regulatory element. In some cases, a human derived regulatory element is combined with a mouse derived regulatory element.

The term "human derived" as used herein refers to sequences that are found in a human genome (or a human genome build), or sequences homologous thereto. A homologous sequence may be a sequence which has a region with at least 80% sequence identity (e.g., as measured by BLAST) as compared to a region of the human genome. For example, a sequence that is at least 80%, at least 85%, at least 90%, at least 91%, at least 92%, at least 93%, at least 94%, at least 95%, at least 96%, at least 97%, at least 98%, or at least 99% homologous to a human sequence is deemed human derived. In some cases, a regulatory element contains a human derived sequence and a non-human derived sequence such that overall the regulatory element has low sequence identity to the human genome, while a part of the regulatory element has 100% sequence identity (or local sequence identity) to a sequence in the human genome.

In some cases, a human-derived regulatory element is a sequence that is 100% identical to a human sequence. In some instances, the sequence of a cell-type selective regulatory element is 100% human derived.

In other instances, at least 5%, 10%, 20%, 30%, 40%, 50%, 60%, 70%, 80%, 90%, 95%, 98%, or 99% of the regulatory element sequence is human derived. For example, a regulatory element can have 50% of its sequence be human derived, and the remaining 50% be non-human derived (e.g., mouse derived or fully synthetic). For further example, a regulatory element that is regarded as 50% human derived and comprises 300 bp may have an overall 45% sequence identity to a sequence in the human genome, while base pairs 1-150 of the RE may have 90% identity (local sequence identity) to a similarly sized region of the human genome.

In some instances, a sequence that is homologous to a human derived regulatory sequence is at least 90% identical to a human sequence. In some cases, a regulatory element herein comprises a sequence that has at least 80%, at least 85%, at least 90%, at least 91%, at least 92%, at least 93%, at least 94%, at least 95%, at least 96%, at least 97%, at least 98%, or at least 99% identity to any one of SEQ ID NOs: 1, 23-31, and 33. In some cases, sequence identity is measured by BLAST. When a regulatory element comprises a sequence that is homologous (e.g., at least 80%, at least 85%, at least 90%, at least 95%, or at least 99% sequence identity) to any one or more of SEQ ID NOs: 23-29, or a functional fragment or combination thereof, such regulatory element results in higher expression of an operably linked transgene (when a promoter is also present in the expression vector or cassette), as compared to a similar vector without the regulatory element. Such higher expression of a transgene can be observed, e.g., in HEK293T or CHO cells.

In some cases, one or more regulatory elements comprise any one or more of SEQ ID NO: 23-29 combined with or used in combination with any one or more of SEQ ID NOs: 1-22 with or without a linker sequence such as SEQ ID NO: 33. In some cases, any two regulatory elements of this disclosure are linked together using a polynucleotide linker comprising 1-50 nucleotides, such as SEQ ID NO: 33 or a variant thereof. In some cases, the linker sequence is a human derived sequence. In some cases, the linker sequence is mouse derived or non-naturally occurring. In some cases, two regulatory elements are joined without a linker or without any intervening sequence. In some cases, a linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides. In some cases, the linker sequence is a result of restriction enzyme site, ligation, PCR, and/or cloning.

In some cases, a human derived regulatory element is combined with a mouse derived regulatory element, such as SEQ ID NO: 32, which is a combination of SEQ ID NO: 8 (a mouse derived sequence) and SEQ ID NOs: 23-29 (human derived sequences). In some cases, cell-type selective regulatory elements are combined directly with no additional linker sequence. In other cases, cell-type selective regulatory elements are combined with one or more short linker sequences which can be either deliberate or cloning artifacts. In some cases, a linker sequence comprises 1-50 bases. For example, SEQ ID NO: 31 comprises the sequence of SEQ ID NOs: 1 and 23-29 along with an additional 19 bp of the genomic sequence (SEQ ID NO: 33) immediately following the sequence of SEQ ID NO: 1. SEQ ID NO: 32 also includes these 19 bp but without the sequence of SEQ ID NO: 1. In other examples, the combined cell-type selective regulatory elements can include short sequences, generally less than 50 bp, less than 20 bp, less than 15 bp, or less than 10 bp, from a cloning plasmid or restriction enzyme recognition site.

In some cases, regulatory elements can be derived from non-coding DNA sequences. In some cases, regulatory elements derived from non-coding DNA are associated with genes, such as upstream sequences, introns, 3' and 5' untranslated regions (UTRs), and/or downstream regions. In other cases, regulatory elements derived from non-coding DNA sequences are not associated with a gene. In some cases, regulatory elements are derived from coding sequences. In some cases, the genomic region from which a regulatory element is derived is distinct from the genomic region from which an operably linked transgene is derived. In some cases, a RE is derived from a distal genomic region or location with respect to the genomic region or location from which the transgene is derived (such as a naturally occurring or an endogenous version of the transgene).

In one aspect, a regulatory element is any non-coding sequence that modulates gene expression, e.g., selectivity of expression in a target cell. In some cases, the target cell is a PV neuron. In some cases, a regulatory element is derived from a genomic sequence upstream of a transcription initiation site, a 5' UTR sequence, an exonic sequence, an intronic sequence, or a 3' UTR sequence. In some cases, a human derived regulatory element comprises an intronic human derived sequence. In some cases, a regulatory element comprises an enhancer, and its presence in an expression cassette along with a promoter increases expression of an operably linked transgene in the target cell-type (e.g., PV neurons) as compared to expression of the same transgene by the promoter without the enhancer. In some cases, an enhancer increases expression of an operably linked transgene through either a transcriptional mechanism, posttranscriptional mechanism, or both. In some cases, a regulatory element comprises an enhancer sequence, a promoter sequence, or a combination of the enhancer and promoter sequences. In some cases, a regulatory element comprises one or more of a human derived enhancer sequence, a human derived promoter sequence, a human derived intronic sequence, and/or a combination thereof.

In some cases, a regulatory element comprises one or more of SEQ ID NOs: 1-32, or a fragment or a combination thereof, or sequences having at least 80%, at least 85%, at least 90%, at least 95%, or at least 99% sequence identity thereto. In some cases, a regulatory element comprises one or more of SEQ ID NOs: 1-22, or a fragment or a combination thereof, or sequences having at least 80%, at least 85%, at least 90%, at least 95%, or at least 99% sequence identity thereto. In some cases, a regulatory element comprises one or more of SEQ ID NOs: 23-29, or a fragment or a combination thereof, or sequences having at least 80%, at least 85%, at least 90%, at least 95%, or at least 99% sequence identity thereto. In some cases, a regulatory element comprises one or more of SEQ ID NOs: 30-32, or a fragment or a combination thereof, or sequences having at least 80%, at least 85%, at least 90%, at least 95%, or at least 99% sequence identity thereto. In some cases, a regulatory element comprises a sequence of SEQ ID NOs: 30-32, or a fragment or a combination thereof, or sequences having at least 80%, at least 85%, at least 90%, at least 95%, or at least 99% sequence identity thereto.

In some instances, a regulatory element is derived from non-human DNA sequences or both human and non-human genomic sequences. In some cases, cell-type selective regulatory elements, or parts thereof, are homologous to a mammalian genomic sequence. In some cases, the regulatory elements have at least 80%, at least 85%, at least 90%, at least 91%, at least 92%, at least 93%, at least 94%, at least 95%, at least 96%, at least 97%, at least 98%, or at least 99% identity to a mammalian genomic sequence. In some cases, a regulatory element is derived from a mouse genomic sequence. In some cases, a regulatory element, or fragments thereof, has at least about 80%, 85%, 90%, 91%, 92%, 93%, 94%, 95%, 96%, 97%, 98%, 99% or more than 99% identity to a mouse genomic sequence or a non-human mammalian genomic sequence. In some cases, sequence identity is measured by BLAST. In some cases, the regulatory elements may comprise any of SEQ ID NOs: 1-33, or a fragment or a combination thereof, or sequences having at least 80%, at least 85%, at least 90%, at least 95%, or at least 99% sequence identity thereto.

In some cases, cell-type selective regulatory elements are short. In some cases, the size of the regulatory elements is compatible with the cloning capacity of a vector, e.g., a viral vector or rAAV, such that the combined size of a transgene and one or more regulatory elements does not exceed the cloning capacity of a vector. In some cases, the cell-type selective regulatory elements have a length of up to about 2050 bp, 2000 bp, 1900 bp, 1800 bp, 1700 bp, 1600 bp, 1500 bp, 1400 bp, 1300 bp, 1200 bp, 1100 bp, 1000 bp, 900 bp, 800 bp, 700 bp, 600 bp, 500 bp, 400 bp, 300 bp, 200 bp, or 100 bp. In some cases, the cell-type selective regulatory elements have a total length of no more than about 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1000 bp, 1010 bp, 1020 bp, 1030 bp, 1040 bp, 1050 bp, 1060 bp, 1070 bp, 1080 bp, 1090 bp, 1100 bp, 1200 bp, 1300 bp, 1500 bp, 1600 bp, 1700 bp, 1800 bp, 1900 bp, or 2000 bp. In some cases, the cell-type selective regulatory elements have a length of about 100 bp-1100 bp, 100 bp-1000 bp, 100 bp-900 bp, 200 bp-900 bp, 200 bp-800 bp, 300 bp-600 bp, 400 bp-800 bp, 500 bp-600 bp, or 600 bp-900 bp. In some cases, a regulatory element is between about 400-600 bp, 400-600 bp, 400-700 bp, 400-800 bp, 400-900 bp, 400-1000 bp, or 400-1500 bp. In some cases, a regulatory element is between about 500-600 bp, 500-700 bp, 500-800 bp, 500-900 bp, 500-1000 bp, or 500-1500 bp. In some cases, two or more regulatory elements are combined to form a larger cell-type selective regulatory element of 1300-2500 bp, 1300-2060 bp, about 1350 bp, about 2050 bp, or about 1880 bp.

In some cases, two or more cell-type selective regulatory elements can be combined. For example, two, three, four, five, six, seven, eight, nine, ten or more cell-type selective regulatory elements can be combined. For example, SEQ ID NO: 30 comprises sequences from seven regulatory elements, i.e., SEQ ID NOs: 23-29, all of which are derived from human genomic sequence. In some cases, cell-type selective regulatory elements refer to PV-neuron selective regulatory elements.

In some cases, a cell-type selective regulatory element is repeated two or more times to make a combined regulatory element that is also cell-type selective or has enhance cell-type selective property. In some cases, two or more regulatory elements with different cell-type selectivity are combined. In some cases, a cell-type selective regulatory element is combined with a non-selective regulatory element, e.g., a non-selective enhancer element that drives high gene expression. For example, a promoter regulatory element with high selectivity for a target cell can be combined with a regulatory element with high efficiency of expression. In some cases, one or more cell type-selective regulatory elements are combined with one or more high efficiency regulatory elements. For example, any one or more of SEQ ID NOs: 1-32, or a fragment or a combination thereof, or sequences having at least 80%, at least 85%, at least 90%, at least 95%, or at least 99% sequence identity thereto, can be combined with a constitutive promoter, such as a GAD2 promoter, a human synapsin promoter, a minCMV promoter, a TATA box, a super core promoter, or an EF1a promoter, or a combination thereof.

In some aspects, the present disclosure provides a list of regulatory elements that can be added to any gene therapy to result in selective gene expression in a target cell type, such as a PV neuron over one or more non-target cell types, such as non-PV CNS cells, including but not limited to excitatory cells and/or non-PV GABAergic cells.

In some cases, cell-type selective regulatory elements can be combined with other regulatory elements such as a high expressing promoter or a sequence that increases mRNA stability. In some cases, one or more cell-type selective regulatory elements are combined with a human, a non-human, or a non-mammalian sequence, for example a hSyn1 promoter, CBA promoter, a CMV promoter, an EF1a promoter, a polyA signal (e.g., SV40 polyA signal), or a post-transcriptional regulatory element such as woodchuck hepatitis virus post-transcriptional regulatory element (WPRE).

In some cases, the combined regulatory elements can come from different species. The combined regulatory elements can come from different genomic regions within a species. In some cases, regulatory elements are derived from distal genomic sequences, e.g., sequences that do not normally or naturally associate with each other or with a cell type of interest, are combined. In some cases, individual regulatory elements used to make a combined regulatory element can come from different human chromosomes.

In one aspect, a regulatory element of the disclosure comprises a functional fragment of any of SEQ ID NOs: 1-32, or a combination thereof, or sequences having at least 80%, at least 85%, at least 90%, at least 95%, or at least 99% sequence identity thereto. Such functional fragment can increase expression of a transgene in an expression cassette or vector when compared to a similar expression cassette or vector without the regulatory element. Such a functional fragment can function as an enhancer to increase cell-type selective expression when the fragment is operably linked to a transgene as compared to a similar vector or cassette without the functional fragment. A fragment is preferably more than 30, 40, 50, or 60 bp in length.

In some cases, a PV cell selective regulatory element or any regulatory element of this disclosure comprises any one of SEQ ID NOs: 1-32, (ii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 1-32, (iii) a functional fragment of any sequence of (i) or (ii), or (iv) a combination of any sequence of (i), (ii) and/or (iii). In some cases, sequence identity is measured by BLAST. In some cases, two or more of SEQ ID NOs: 1-29, or a functional fragment or a combination thereof, or sequences having at least 80%, at least 85%, at least 90%, at least 95%, or at least 99% sequence identity thereto, are used as a regulatory element to increase transgene expression selectively in PV cells as compared to non-PV CNS cells, or to in any target cell type as compared to non-target cell type. In some cases, a functional fragment is one that results in selective expression in a target cell type over one or more non-target cell types.

In some cases, two or more copies of a regulatory element can be used to enhance selective expression in a target cell, e.g., two or more copies of any one of SEQ ID NOs: 1-29, or a fragment or a combination thereof, or sequences having at least 80%, at least 85%, at least 90%, at least 95%, or at least 99% sequence identity thereto.

In other cases, one or more of SEQ ID NOs: 1-32, or a fragment or a combination thereof, or sequences having at least 80%, at least 85%, at least 90%, at least 95%, or at least 99% sequence identity thereto, are operably linked to another regulatory element, such as a promoter or enhancer, to further increase selective expression in a target cell. In some cases, one can enhance any gene therapy by adding one or more regulatory elements as disclosed herein to improve or increase expression from the gene therapy in a target cell as compared to non-target cells. In some cases, the target cell is PV neurons or GABAergic cells that express parvalbumin.

In some aspects, one or more regulatory elements (e.g., any one or more of SEQ ID NOs: 1-32, or a fragment or a combination thereof, or sequences having at least 80%, at least 85%, at least 90%, at least 95%, or at least 99% sequence identity thereto) disclosed herein show cell-type selectivity for a target cell type over at least one, at least two, at least three, at least four, at least five, or more than five non-target cell types. In some cases, a regulatory element drives selective expression or preferential expression in a target cell subtype over at least one, at least two, at least three, at least four, at least five, or more than five non-target subtypes, or all other known subtypes of the cell. For example, GABAergic cells comprise different subtypes, including PV cells. In some cases, the target cell type is a PV cell. In some cases, one or more regulatory elements are selective for PV cells over at least one, at least two, at least three, at least four, at least five, or more than five non-target cell types. In some instances, one or more regulatory elements are selective for PV cells over all other known CNS cell-types.

In some cases, any one or more of SEQ ID NOs: 1-32, or a fragment or a combination thereof, or sequences having at least 80%, at least 85%, at least 90%, at least 95%, or at least 99% sequence identity thereto, can be combined with any one or more of SEQ ID NOs: 1-32, or a fragment or a combination thereof, or sequences having at least 80%, at least 85%, at least 90%, at least 95%, or at least 99% sequence identity thereto. In some cases, such combined regulatory elements are linked using a linker of 1-50 nucleotides. In some cases, such combined regulatory elements are not linked.

In some cases, one or more regulatory elements disclosed herein, when operably linked to any transgene (e.g., a reporter transgene or a therapeutic transgene), drives selective expression or preferential expression in at least one target cell type at a level that is statistically significantly higher than the expression driven by CAG, EF1α, a constitutive promoter (e.g., SV40, CMV, UBC, PGK, and CBA), or a non-selective regulatory element (e.g., SEQ ID NO: 34, or a fragment thereof, or a sequence having at least 80%, at least 85%, at least 90%, at least 95%, or at least 99% sequence identity thereto) when operably linked to the same transgene, or by the same construct without the regulatory elements. In some cases, statistically significantly higher means the regulatory elements drive selective expression in the target cell type at a level that is at least 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, or 100 times the expression level by CAG, EF1α, a constitutive promoter (e.g., SV40, CMV, UBC, PGK, and CBA), or a non-selective regulatory element when operably linked to the same transgene, or by the same construct without the regulatory elements. In some cases, such cell-type selective expression is assayed using a co-localization assay as described herein. In some cases, the target cell type is a parvalbumin cell. In some cases, such co-localization assay is conducted using an anti-PV antibody. In some cases, such co-localization assay is conducted using a PV-Cre mouse as disclosed herein. In some cases, the non-selective regulatory element is SEQ ID NO: 34, or a fragment thereof, or a sequence having at least 80%, at least 85%, at least 90%, at least 95%, or at least 99% sequence identity thereto.

Expression Cassettes

The terms "expression cassette" and "nucleic acid cassette" are used interchangeably to refer to a polynucleotide molecule or a nucleic acid sequence. In some cases, an expression cassette comprises one or more regulatory elements disclosed herein operably linked to a transgene. In some cases, an expression cassette comprises one or more regulatory elements. In some cases, an expression cassette comprises one or more cell type selective regulatory elements disclosed herein. In some cases, an expression cassette comprises one or more PV cell selective regulatory elements disclosed herein. In some cases, the expression cassette further comprises a promoter. In some cases, an expression cassette comprises one or more sequences of SEQ ID NOs: 1-32 and/or any combination thereof. In some cases, an expression cassette comprises one or more of SEQ ID NOs: 1-32, (ii) a nucleic acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 1-32, (iii) a functional fragment of any sequence of (i) or (ii), or (iv) a combination of any sequence of (i), (ii) and/or (iii). In some cases, sequence identity is measured by BLAST. In some cases, a regulatory element is located upstream of a transgene in an expression cassette. In some cases, a regulatory element is located downstream of a transgene in an expression cassette. In some cases, an expression cassette further comprises a promoter, e.g., a hSyn1 promoter, CBA promoter, a CMV promoter, an EF1a promoter, a polyA signal (e.g., SV40 polyA signal), or a post-transcriptional regulatory element such as woodchuck hepatitis virus post-transcriptional regulatory element (WPRE).

In some aspects, one or more regulatory elements described herein are operably linked to a transgene in an expression cassette. In some cases, a gene therapy comprises an expression cassette comprising a transgene operably linked to one or more, two or more, three or more, four or more, or five or more regulatory elements of the present disclosure to result in selective expression of the transgene in a target tissue or cell type, such as PV neurons. In some cases, an expression cassette comprises one or more PV cell selective regulatory elements or one or more regulatory elements disclosed herein operably linked to a transgene, e.g., a reporter gene, eGFP, SCN1A, SNC2A, SNC8A, SCN1B, SCN2B, KV3.1, KV3.2, KV3.3, STXBP1, a DNA binding protein, or a variant or a fragment thereof, or sequences having at least 80%, at least 85%, at least 90%, at least 95%, or at least 99% sequence identity thereto.

In some cases, an expression cassette is adapted for delivery via gene therapy. In some cases, an expression cassette is a linear or a circular construct. In some cases, an expression cassette is part of a plasmid, vector, a viral vector, or rAAV.

In some cases, a gene therapy is administered directly to the CNS of a subject in need thereof or systematically via injection and/or infusion. In some cases, such subject has been diagnosed with a disease or condition associated with a haploinsufficiency or a genetic mutation, such as a haploinsufficiency or a mutation in any one of the following genes: SCN1A, SNC2A, SNC8A, SCN1B, SCN2B, KV3.1, KV3.2, KV3.3, or STXBP1. In some cases, the subject is at risk for or has Dravet syndrome, Alzheimer's disease, epilepsy, neurodegeneration, tauopathy, neuronal hypoexcitability and/or seizures. In some cases, such gene therapy is delivered using a virus or a viral vector, such as rAAV. In some cases, an AAV serotype with a tropism for CNS cells and/or ability to cross the blood brain barrier is used, such as AAV9 or a variant thereof.

In some cases, one or more regulatory elements (e.g., one or more of SEQ ID NOs: 1-32, or a fragment or a combination thereof, or sequences having at least 80%, at least 85%, at least 90%, at least 95%, or at least 99% sequence identity thereto) operably linked to a transgene in an expression cassette result in selective gene expression in PV cells as compared to non-PV CNS cells, or as compared to a control element, such as a CAG, EF1α, a constitutive promoter (e.g., SV40, CMV, UBC, PGK, and CBA), or a non-selective regulatory element (e.g., SEQ ID NO: 34, or a functional fragment thereof, or a sequence having at least 80%, at least 85%, at least 90%, at least 95%, or at least 99% sequence identity thereto). In some cases, regulatory elements result in at least 50%, at least 60%, at least 70%, at least 80%, or at least 90% of all cells expressing the transgene are PV neurons. In some cases, regulatory elements result in selective gene expression in PV neurons that is about 1.5 times, 2 times, 3 times, 4 times, 5 times, 6 times, 7 times, 7.5 times, 8 times, 9 times, or 10 times higher than expected for natural distribution of PV neurons in CNS. In some cases, a regulatory element drives selective expression in PV cells, wherein the percentage of PV cells expressing the transgene is at a percentage that is at least 1.5 fold, at least 2 fold, at least 3 fold, at least 4 fold, at least 5 fold, at least 6 fold, at least 7 fold, at least 8 fold, at least 9 fold, or at least 10 fold higher than the expected distribution of PV cells in the CNS, or at least 1-5%, 5%-10%, 10-15%, 15-20%, 20-25%, 25-30%, 30-35%, 35-40%, 40-45%, 45-50%, 50-55%, 55-60%, 65-70%, 70-75%, 75-80%, 80-85%, 85-90%, or 90-95% higher than the expression in PV cells when the transgene is operably linked to CAG, EF1α, a constitutive promoter (e.g., SV40, CMV, UBC, PGK, and CBA), or a non-selective regulatory element having a sequence of SEQ ID NO: 34, or a functional fragment thereof, or a sequence having at least 80%, at least 85%, at least 90%, at least 95%, or at least 99% sequence identity thereto, and as measured in an immunohistochemical co-localization assay. In some cases, a regulatory element in an expression cassette, or use of such regulatory element in an expression cassette, results in selective gene expression in PV cells, or PV cells in the CNS, or PV neurons, wherein about 10%, 15%, 20%, 25%, 30%, 35%, 40%, 45%, 50%, 55%, 60%, 65%, 70%, 75%, 80%, 85%, 90%, or 95% of the cells expressing the transgene are PV positive.

In some cases, an expression cassette or a gene therapy comprises one or more, two or more, three or more, four or more, five or more, six or more, seven or more, eight or more, nine or more, or ten or more regulatory elements as described in TABLE 1, e.g., SEQ ID NOs: 1-32, or a functional fragment or a combination thereof, or sequences having at least 80%, at least 85%, at least 90%, at least 95%, or at least 99% sequence identity thereto.

In some cases, one or more PV cell selective regulatory elements or one or more regulatory elements disclosed herein are operably linked to any transgene in an expression cassette. In some cases, the expression cassette is a gene therapy. In some cases, the expression cassette is part of a vector or a plasmid, e.g., a viral vector or rAAV vector. In some cases, the expression cassette is part of AAV1, AAV8, AAV9, or AAVDJ or a variant or hybrid thereof. In some cases, the expression cassette comprises one or more PV cell selective regulatory elements or one or more regulatory elements disclosed herein operably linked to a transgene, wherein the transgene is SCN1A, SNC2A, SNC8A, SCN1B, SCN2B, KV3.1, KAV3.2, KV3.3, STXBP1, DNA binding protein (e.g., transcriptional modulator of an endogenous gene), or a variant or a functional fragment thereof, or a sequence having at least 80%, at least 85%, at least 90%, at least 95%, or at least 99% sequence identity thereto. In some cases, such regulatory elements increase the selective expression of the transgene in PV neurons as compared to non-PV CNS cell-types. In some cases, such regulatory elements increase the expression of the transgene selectively in a target cell type, such as a PV neuron. In some cases, the target cell type is a PV cell.

Techniques contemplated herein for gene therapy of somatic cells include delivery via a viral vector (e.g., retroviral, adenoviral, AAV, helper-dependent adenoviral systems, hybrid adenoviral systems, herpes simplex, pox virus, lentivirus, and Epstein-Barr virus), and non-viral systems, such as physical systems (naked DNA, DNA bombardment, electroporation, hydrodynamic, ultrasound, and magnetofection), and chemical system (cationic lipids, different cationic polymers, and lipid polymers).

The cloning capacity of vectors or viral expression vectors is a particular challenge for expression of large transgenes. For example, AAV vectors typically have a packaging capacity of ~4.8 kb, lentiviruses typically have a capacity of ~8 kb, adenoviruses typically have a capacity of ~7.5 kb and alphaviruses typically have a capacity of ~7.5 kb. Some viruses can have larger packaging capacities, for example herpesvirus can have a capacity of >30 kb and vaccinia a capacity of ~25 kb. Advantages of using AAV for gene therapy include low pathogenicity, very low frequency of integration into the host genome, and the ability to infect dividing and non-dividing cells.

To address the size constraints of certain viral vectors or to improve expression from viral vectors, the present disclosure contemplates the use of regulatory elements that are shorter than 2.5 kb, 2 kb, 1.5 kb, 1 kb, 900 bp, 800 bp, 700 bp, 600 bp, 500 bp, 400 bp, 300 bp, 200 bp, 150 bp, or 110 bp, but at least 10 bp, 50 bp or 100 bp in length. In some cases, the size of the combined regulatory element is about 2500 bp, 2000 bp, 1500 bp, 1400 bp, 1300 bp, 1200 bp, 1100 bp, or 1000 bp. In some cases, each combined regulatory element has a total length of about 100 bp, 200 bp, 300 bp, 400 bp, 500 bp, 600 bp, 700 bp, 800 bp, 900 bp, 1000 bp, 1100 bp, 1200 bp, 1300 bp, 1400 bp, 1500 bp, 1600 bp, 1700 bp, 1800 bp, 1900 bp, 2000 bp, 2100 bp, 2200 bp, 2300 bp, 2400 bp, or 2500 bp. In some cases, the size of a combined RE has a total length of about 200 bp-3000 bp, 200 bp-2500 bp, 200 bp-2100 bp, 500 bp-2500 bp, 1000 bp-2500 bp, 1500 bp-2500 bp, 1500b-2000 bp, or 2000 bp-2500 bp.

In some cases, a regulatory element of the disclosure is preferably (i) one that selectively drives expression in a cell-type of interest, such as PV cells; (ii) includes a human derived sequence, and (iii) is smaller than 2.5 kb, 2 kb, 1.5 kb, or 1 kb.

Also contemplated herein are expression cassettes, which can be a circular or linear nucleic acid molecule. In some cases, an expression cassette is delivered to cells (e.g., a plurality of different cells or cell types including target cells or cell types and/or non-target cell types) in a vector (e.g., an expression vector). A vector can be an integrating or non-integrating vector, referring to the ability of the vector to integrate the expression cassette and/or transgene into a genome of a cell. Either an integrating vector or a non-integrating vector can be used to deliver an expression cassette containing a transgene operably linked to a regulatory element. Examples of vectors include, but are not limited to, (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs); episomal vectors; transposons (e.g., PiggyBac); and (b) viral vectors such as retroviral vectors, lentiviral vectors, adenoviral vectors, and AAV vectors. Viruses have several advantages for delivery of nucleic acids, including high infectivity and/or tropism for certain target cells or tissues. In some cases, a virus is used to deliver a nucleic acid molecule or expression cassette comprising one or more regulatory elements, as described herein, operably linked to a transgene.

Preferred characteristics of viral gene therapy vectors or gene delivery vectors include the ability to be reproducible and stably propagated and purified to high titers; to mediate targeted delivery (e.g., to deliver the transgene specifically to a tissue or organ of interest without widespread vector dissemination elsewhere or off-target delivery); and to mediate gene delivery and/or transgene expression without inducing harmful side effects or off-target effects. To avoid potential harmful side effects, targeted expression or tissue/cell type selective expression can be achieved by placing the transgene under the control of a cell-type-selective regulatory element, e.g., one or more of SEQ ID NOs: 1-32, or a functional fragment or a combination thereof, or sequences having at least 80%, at least 85%, at least 90%, at least 95%, or at least 99% sequence identity thereto, an enhancer, promoter, stability element, UTR, or a combination thereof. For example, viral particles containing a viral vector can be designed to infect many different cell types but expression of the transgene is enhanced and/or optimized in a cell type of interest (e.g. PV neurons), and expression of the transgene is reduced and/or minimized in other non-target cell types (e.g., non-PV CNS cells). The differential expression of the transgene in different cell types can be controlled, engineered, or manipulated using different transcription factors or regulatory elements that are selective for one or more cell types. In some cases, one or more regulatory elements, such as a promoter or enhancer, or a combination thereof, are operably linked to a transgene to drive tissue- or cell-selective expression of the transgene. In some cases, one or more regulatory elements used in a gene therapy or a vector drive gene expression in a cell type selective manner, i.e., confer selective gene expression in a target cell, cell type, or tissue, and/or do not drive gene expression in one or more (e.g., at least one, two, three, or four) off-target cells or cell types. In some cases, one or more regulatory elements operably linked to a transgene enhances selective expression of the transgene in a target cell, cell type, or tissue, while the one or more regulatory elements suppress transgene expression in off-target cells, cell type, or tissue, or confers significantly lower, de minimis, or statistically lower gene expression in one or more off-target cells, cell types, or tissue.

Several serotypes of AAV, non-pathogenic parvovirus, have been engineered for the purposes of gene delivery, some of which are known to have tropism for certain tissues or cell types. Viruses used for various gene-therapy applications can be engineered to be replication-deficient or to have low toxicity and low pathogenicity in a subject or a host. Such virus-based vectors can be obtained by deleting all, or some, of the coding regions from the viral genome, and leaving intact those sequences (e.g., inverted terminal repeat sequences) that are necessary for functions such as packaging the vector genome into the virus capsid or the integration of vector nucleic acid (e.g., DNA) into the host chromatin. An expression cassette comprising a transgene, for example, can be cloned into a viral backbone such as a modified or engineered viral backbone lacking viral genes, and used in conjunction with additional vectors (e.g., packaging vectors), which can, for example, when co-transfected, produce recombinant viral vector particles. In some cases, an AAV serotype that can cross the blood brain barrier or infect cells of the CNS is preferred. In some cases, AAV9 or a variant thereof is used to deliver an expression cassette of this disclosure, comprising one or more PV selective regulatory elements operably linked to a transgene.

One advantage of delivering expression cassettes of this disclosure using gene therapy, e.g., rAAV, as described herein, is that such therapies can provide more targeted and sustained therapeutic effects over time. Additionally, viral gene therapies can be engineered to have tropism for a cell type or tissue of interest over non-target cell types or tissues. For example, viral gene therapies can be engineered to infect and deliver a payload or a therapeutic agent, e.g., a transcriptional modulator or a transgene, to one or more regions, tissues, or cell types within the CNS (e.g., PV cells), while having minimal effects on off-target tissues or cell types (e.g., non-CNS tissue or cell types, non-PV CNS cells). In some cases, viral gene therapies can be engineered to deliver a transgene across the blood brain barrier and/or target a specific region or tissue within the CNS (e.g., hippocampus) or a cell type within the CNS, e.g., PV cells.

In some cases, an AAV vector or an AAV viral particle, or virion, used to deliver one or more regulatory elements and a transgene into a cell, cell type, or tissue, in vivo or in vitro, is preferably replication-deficient. In some cases, an AAV virus is engineered or genetically modified so that it can replicate and generate virions only in the presence of helper factors.

In some cases, the expression cassette is designed for delivery by an AAV or a recombinant AAV (rAAV). In some cases, an expression cassette is delivered using a lentivirus or a lentiviral vector. In some cases, larger transgenes, i.e., genes that exceed the cloning capacity of AAV, are preferably delivered using a lentivirus or a lentiviral vector.

The AAV used in the compositions and methods described herein can be of any serotype (e.g., AAV1, AAV2, AAV5, AAV8, AAV9, and AAVDJ), including hybrid or chimeric AAV serotypes. In some cases, AAV is used to deliver and/or express a transgene operably linked to one or more regulatory elements that are selective for PV neurons as compared to non-PV CNS cells. In some cases, an AAV with a high tropism for CNS cells and/or crosses the blood brain barrier is used. In some cases, AAV1, AAV8, AAV9, and/or AAVDJ are used to deliver to deliver an expression cassette described herein.

In some cases, an expression cassette comprises one or more PV cell selective regulatory elements or one or more regulatory elements disclosed herein operably linked to a transgene that is known to be insufficiently expressed in vivo, such as in a disease or condition associated with haploinsufficiency in the gene. In some cases, the transgene is a voltage-gated ion channel (e.g., a sodium ion channel or a potassium ion channel), a neurotransmitter regulator, or a subunit or functional fragment thereof. In some aspects, the transgene is a DNA binding protein, an ion channel, a neurotransmitter regulator, or a subunit of the ion channel or neurotransmitter regulator. In some cases, the transgene is a DNA binding protein that comprises one or more zinc fingers. In some cases, the DNA binding protein comprises a domain of Cas9, a Cas family protein, nuclease-inactivated Cas9 (or dCas9), a dCas family protein, or a transcriptional activator like effector (TALE). In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9.

In some aspects, the transgene is a voltage-gated ion channel or a subunit thereof, such as SCN1A, SNC2A, SNC8A, SCN1B, SCN2B, KV3.1, KV3.2, or KV3.3, or a functional fragment or variant thereof. In some cases, the transgene is an alpha subunit of a sodium ion channel. In some cases, the transgene is a beta subunit of a sodium ion channel. In some aspects, the neurotransmitter regulator is STXBP1 or a functional fragment or variant thereof.

In some aspects, an expression cassette is delivered as a viral vector, such as AAV. In some aspects, the AAV is AAV1, AAV8, AAV9, AAV-DJ, scAAV1, scAAV8, or scAAV9. In some aspects, a gene therapy comprising an expression cassette of this disclosure is administered to a subject in need thereof (e.g., a human patient, a mammal, a transgenic animal, or an animal model). In some cases, the subject in need thereof has symptoms of, has been diagnosed with, or is at risk of developing Alzheimer's disease, Dravet syndrome, epilepsy, neurodegeneration, tauopathy, neuronal hypoexcitability, and/or seizures. In some cases, the subject in need thereof has an insufficient gene expression or a mutation in any one or more of SCN1A, SNC2A, SNC8A, SCN1B, SCN2B, KV3.1, KV3.2, KV3.3, and STXBP1.

In some cases, a gene therapy, such as rAAV9, is used to deliver an expression cassette comprising one or more PV cell selective regulatory elements or one or more regulatory elements disclosed herein operably linked a transgene, wherein the transgene is SCN1A, SNC2A, SNC8A, SCN1B, SCN2B, KV3.1, KV3.2, KV3.3, STXBP1, a DNA binding protein, or a functional fragment thereof, or a sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SCN1A, SNC2A, SNC8A, SCN1B, SCN2B, KV3.1, KV3.2, KV3.3, STXBP1, a DNA binding protein, or a functional fragment thereof. In some cases, the transgene comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 37-43, or a functional fragment thereof, as provided in TABLE 2 below.

In some cases, the transgene is any one of SEQ ID NOs: 36-43, or a functional fragment thereof, or sequences having at least 80%, at least 85%, at least 90%, at least 95%, or at least 99% sequence identity thereto. In some cases, one or more regulatory elements disclosed herein are operably linked to any one of SEQ ID NOs: 36-43 in an expression cassette, or a functional fragment thereof, or sequences having at least 80%, at least 85%, at least 90%, at least 95%, or at least 99% sequence identity thereto.

TABLE 2

List of amino acid sequences disclosed herein.

| SEQ ID NO. | Gene | Amino Acid Sequence |
|---|---|---|
| 36 | eGFP | MVSKGEELFTGVVPILVELDGDVNGHKFSVSGEGEGDATYGKLTLKF ICTTGKLPVPWPTLVTTLTYGVQCFSRYPDHMKQHDFFKSAMPEGYV QERTIFFKDDGNYKTRAEVKFEGDTLVNRIELKGIDFKEDGNILGHKL EYNYNSHNVYIMADKQKNGIKVNFKIRHNIEDGSVQLADHYQQNTPI GDGPVLLPDNHYLSTQSALSKDPNEKRDHMVLL |
| 37 | SCN1B | MGTLLALVVGAALVSSAWGGCVEVDSDTEAVYGMTFKILCISCKRRS ETTAETFTEWTFRQKGTEEFVKILRYENEVLQLEEDERFEGRVVWNG SRGTKDLQDLSIFITNVTYNHSGDYECHVYRLLFFDNYEHNTSVVKKI HLEVVDKANRDMASIVSEIMMYVLIVVLTIWLVAEMVYCYKKIAAA TEAAAQENASEYLAITSESKENCTGVQVAE |
| 38 | SCN2B | MHRDAWLPRPAFSLTGLSLFFSLVPPGRSMEVTVPATLNVLNGSD ARLPCTFNSCYTVNHKQFSLNWTYQECNNCSEEMFLQFRMKIINLKL ERFQDRVEFSGNPSKYDVSVMLRNVQPEDEGIYNCYIMNPPDRHRGH GKIHLQVLMEEPPERDSTVAVIVGASVGGFLAVVILVLMVVKCVRRK KEQKLSTDDLKTEEEGKTDGEGNPDDGAK |
| 39 | SCN1A | MEQTVLVPPGPDSFNFFTRESLAAIERRIAEEKAKNPKPDKKDDDENG PKPNSDLEAGKNLPFIYGDIPPEMVSEPLEDLDPYYINKKTFIVLNKGK AIFRFSATSALYILTPFNPLRKIAIKILVHSLFSMLIMCTILTNCVFMTMS NPPDWTKNVEYTFTGIYTFESLIKIIARGFCLEDFTFLRDPWNWLDFTV ITFAYVTEFVDLGNVSALRTFRVLRALKTISVIPGLKTIVGALIQSVKK LSDVMILTVFCLSVFALIGLQLFMGNLRNKCIQWPPTNASLEEHSIEKN ITVNYNGTLINETVFEFDWKSYIQDSRYHYFLEGFLDALLCGNSSDAG |

TABLE 2-continued

List of amino acid sequences disclosed herein.

| SEQ ID NO. | Gene | Amino Acid Sequence |
|---|---|---|
| | | QCPEGYMCVKAGRNPNYGYTSFDTFSWAFLSLFRLMTQDFWENLYQ LTLRAAGKTYMIFFVLVIFLGSFYLINLILAVVAMAYEEQNQATLEEA EQKEAEFQQMIEQLKKQQEAAQQAATATASEHSREPSAAGRLSDSSS EASKLSSKSAKERRNRRKKRKQKEQSGGEEKDEDEFQKSESEDSIRRK GFRFSIEGNRLTYEKRYSSPHQSLLSIRGSLFSPRRNSRTSLFSFRGRAK DVGSENDFADDEHSTFEDNESRRDSLFVPRRHGERRNSNLSQTSRSSR MLAVFPANGKMHSTVDCNGVVSLVGGPSVPTSPVGQLLPEVIIDKPA TDDNGTTTETEMRKRRSSSFHVSMDFLEDPSQRQRAMSIASILTNTVE ELEESRQKCPPCWYKFSNIFLIWDCSPYWLKVKHVVNLVVMDPFVDL AITICIVLNTLFMAMEHYPMTDHFNNVLTVGNLVFTGIFTAEMFLKIIA MDPYYYFQEGWNIFDGFIVTLSLVELGLANVEGLSVLRSFRLLRVFKL AKSWPTLNMLIKIIGNSVGALGNLTLVLAIIVFIPAVVGMQLFGKSYK DCVCKIASDCQLPRWHMNDFFHSFLIVFRVLCGEWIETMWDCMEVA GQAMCLTVFMMVMVIGNLVVLNLFLALLLSSFSADNLAATDDDNEM NNLQIAVDRMHKGVAYVKRKIYEFIQQSFIRKQKILDEIKPLDDLNNK KDSCMSNHTAEIGKDLDYLKDVNGTTSGIGTGSSVEKYIIDESDYMSF INNPSLTVTVPIAVGESDFENLNTEDFSSESDLEESKEKLNESSSSSEGS TVDIGAPVEEQPVVEPEETLEPEACFTEGCVQRFKCCQINVEEGRGKQ WWNLRRTCFRIVEHNWFETFIVFMILLSSGALAFEDIYIDQRKTIKTML EYADKVFTYIFILEMLLKWVAYGYQTYFTNAWCWLDFLIVDVSLVSL TANALGYSELGAIKSLRTLRALRPLRALSRFEGMRVVVNALLGAIPSI MNVLLVCLIFWLIFSIMGVNLFAGKFYHCINTTTGDRFDIEDVNNHTD CLKLIERNETARWKNVKVNFDNVGFGYLSLLQVATFKGWMDIMYA AVDSRNVELQPKYEESLYMYLYFVIFIIFGSFFTLNLFIGVIIDNFNQQK KKFGGQDIFMTEEQKKYYNAMKKLGSKKPQKPIPRPGNKFQGMVFD FVTRQVFDISIMILICLNMVTMMVETDDQSEYVTTILSRINLVFIVLFTG ECVLKLISLRHYYFTIGWNIFDFVVVILSIVGMFLAELIEKYFVSPTLFR VIRLARIGRILRLIKGAKGIRTLLFALMMSLPALFNIGLLLFLVMFWAIF GMSNFAYVKREVGIDDMFNFETFGNSMICLFQITTSAGWDGLLAPILN SKPPDCDPNKVNPGSSVKGDCGNPSVGIFFFVSYIIISFLVVVNMYIAVI LENFSVATEESAEPLSEDDFEMFYEVWEKFDPDATQFMEFEKLSQFA AALEPPLNLPQPNKLQLIAMDLPMVSGDRIHCLDILFAFTKRVLGESG EMDALRIQMEERFMASNPSKVSYQPITTTLKRKQEEVSAVIIQRAYRR HLLKRTVKQASFTYNKNKIKGGANLLIKEDMIIDRINENSITEKTDLTM STAACPPSYDRVTKPIVEKHEQEGKDEKAKGK |
| 40 | STXBP1 | MAPIGLKAVVGEKIMHDVIKKVKKKGEWKVLVVDQLSMRMLSSCC KMTDIMTEGITIVEDINKRREPLPSLEAVYLITPSEKSVHSLISDFKDPPT AKYRAAHVFFTDSCPDALFNELVKSRAAKVIKTLTEINIAFLPYESQV YSLDSADSFQSFYSPHKAQMKNPILERLAEQIATLCATLKEYPAVRYR GEYKDNALLAQLIQDKLDAYKADDPTMGEGPDKARSQLLILDRGFDP SSPVLHELTFQAMSYDLLPIENDVYKYETSGIGEARVKEVLLDEDDDL WIALRHKHIAEVSQEVTRSLKDFSSSKRMNTGEKTTMRDLSQMLKK MPQYQKELSKYSTHLHLAEDCMKHYQGTVDKLCRVEQDLAMGTDA EGEKIKDPMRAIVPILLDANVSTYDKIRIILLYIFLKNGITEENLNKLIQH AQIPPEDSEIITNMAHLGVPIVTDSTLRRRSKPERKERISEQTYQLSRWT PIIKDIMEDTIEDKLDTKHYPYISTRSSASFSTTAVSARYGHWHKNKAP GEYRSGPRLIIFILGGVSLNEMRCAYEVTQANGKWEVLIGSTHILTPTK FLMDLRHPDFRESSRVSFEDQAPTME |
| 41 | Kv3.1 | MGQGDESERIVINVGGTRHQTYRSTLRTLPGTRLAWLAEPDAHSHFD YDPRADEFFFDRHPGVFAHILNYYRTGKLHCPADVCGPLYEEELAFW GIDETDVEPCCWMTYRQHRDAEEEALDSFGGAPLDNSADDADADGPG DSGDGEDELEMTKRLALSDSPDGRPGGFWRRWQPRIWALFEDPYSSR YARYVAFASLFFILVSITTFCLETHERFNPIVNKTEIENVRNGTQVRYY REAETEAFLTYIEGVCVVWFTFEFLMRVIFCPNKVEFIKNSLNIIDFVAI LPFYLEVGLSGLSSKAAKDVLGFLRVVRFVRILRIFKLTRHFVGLRVL GHTLRASTNEFLLLIIFLALGVLIFATMIYYAERIGAQPNDPSASEHTHF KNIPIGFWWAVVTMTTLGYGDMYPQTWSGMLVGALCALAGVLTIA MPVPVIVNNFGMYYSLAMAKQKLPKKKKKHIPRPPQLGSPNYCKSV VNSPHHSTQSDTCPLAQEEILEINRAGRKPLRGMSI |
| 42 | Kv3.2 | MGKIESNERVILNVGGTRHETYRSTLKTLPGTRLALLASSEPQGDCLT AAGDKLQPLPPPLSPPPRPPPLSPVPSGCFEGGAGNCSSHGGNGGNGG SDHPGGGREFFFDRHPGVFAYVLNYYRTGKLHCPADVCGPLFEEELA FWGIDETDVEPCCWMTYRQHRDAEEEALDIFETPDLIGGDPGDDEDLA AKRLGIEDAAGLGGPDGKSGRWRKLQPRMWALFEDPYSSRAARFIAF ASLFFILVSITTFCLETHEAFNIVKNKTEPVINGTSPVLQYEIETDPALTY VEGVCVVWFTFEFLVRIVFSPNKLEFIKNLLNIIDFVAILPFYLEVGLSG LSSKAAKDVLGFLRVVRFVRILRIFKLTRHFVGLRVLGHTLRASTNEF LLLIIFLALGVLIFATMIYYAERVGAQPNDPSASEHTQFKNIPIGFWWA VVTMTTLGYGDMYPQTWSGMLVGALCALAGVLTIAMPVPVIVNNFG MYYSLAMAKQKLPRKRKKHIPPAPLASSPTFCKTELNMACNSTQSDT CLGKENRLLEHNRSVLSGDDSTGSEPPLSPPPERLPIRRSSTRDKNRRGE |

TABLE 2-continued

List of amino acid sequences disclosed herein.

| SEQ ID NO. | Gene | Amino Acid Sequence |
|---|---|---|
| | | TCFLLTTGDYTCASDGGIRKASTLEPMESTAQTKGDTRPEAHWNCAH LLNFGCPTGSSFPTL |
| 43 | Kv3.3 | MLSSVCVSSFRGRQGASKQQPAPPPQPPESPPPPPLPPQQQQPAQPGPA ASPAGPPAPRGPGDRRAEPCPGLPAAAMGRHGGGGGDSGKIVINVGG VRHETYRSTLRTLPGTRLAGLTEPEAAARFDYDPGADEFFFDRHPGVF AYVLNYYRTGKLHCPADVCGPLFEEELGFWGIDETDVEACCWMTYR QHRDAEEALDSFEAPDPAGAANAANAAGAHDGGLDDEAGAGGGGL DGAGGELKRLCFQDAGGGAGGPPGGAGGAGGTWWRRWQPRVWAL FEDPYSSRAARYVAFASLFFILISITTFCLETHEGFIHISNKTVTQASPIP GAPPENITNVEVETEPPFLTYVEGVCVVWFTFEFLMRITFCPDKVEFLKS SLNIIDCVAILPFYLEVGLSGLSSKAAKDVLGFLRVVRFVRILRIFKLTR HFVGLRVLGHTLRASTNEFLLLIIFLALGVLIFATMIYYAERIGADPDDI LGSNHTYFKNIPIGFWWAVVTMTTLGYGDMYPKTWSGMLVGALCA LAGVLTIAMPVPVIVNNFGMYYSLAMAKQKLPKKKNKHIPRPPQPGS PNYCKPDPPPPPPHPFIHGSGGISPPPPITPPSMGVTVAGAYPAGPHTH PGLLRGGAGGLGIMGLPPLPAPGEPCPLAQEEVIEINRADPRPNGDPA AAALAHEDCPAIDQPAMSPEDKSPITPGSRGRYSRDRACFLLTDYAPS PDGSIRKATGAPPLPPQDWRKPGPPSFLPDLNANAAAWISP |

In some cases, the one or more PV cell selective regulatory elements comprise sequences of SEQ ID NOs: 1-32, a functional fragment or a combination thereof, or sequences comprising at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity thereto. In some cases, sequence identity is measured by BLAST. In some cases, such gene therapy is used to treat epilepsies, neurodegeneration, tauopathy, neuronal hypoexcitability, Dravet syndrome and/or Alzheimer's disease. In some cases, such gene therapy is used to treat epilepsy and/or seizures associated with Dravet syndrome and/or Alzheimer's disease. In some cases, treatment using a gene therapy described herein results in reduced seizure frequency and/or duration. In some cases, treatment using a gene therapy described herein results in increased formation of functional sodium ion channels, functional potassium ion channels, or functional neurotransmitter regulatory in vivo.

In some cases, AAV serotypes 1, 8, and/or 9, or a hybrid thereof can be used with an expression cassettes described herein to target selective expression in PV cells. In some cases, an expression cassette designed for delivery by an AAV comprises a 5' ITR, one or more cell-type selective regulatory elements, an optional enhancer, an optional minimal promoter, a transgene, optionally one or more introns, an optional polyA signal, and a 3' ITR. In some instances, an expression cassette can contain a 5' ITR, two cell-type selective REs, a basal promoter, a transgene, one or more post-transcriptional RNA regulatory elements, and a 3' ITR.

Figure 7:
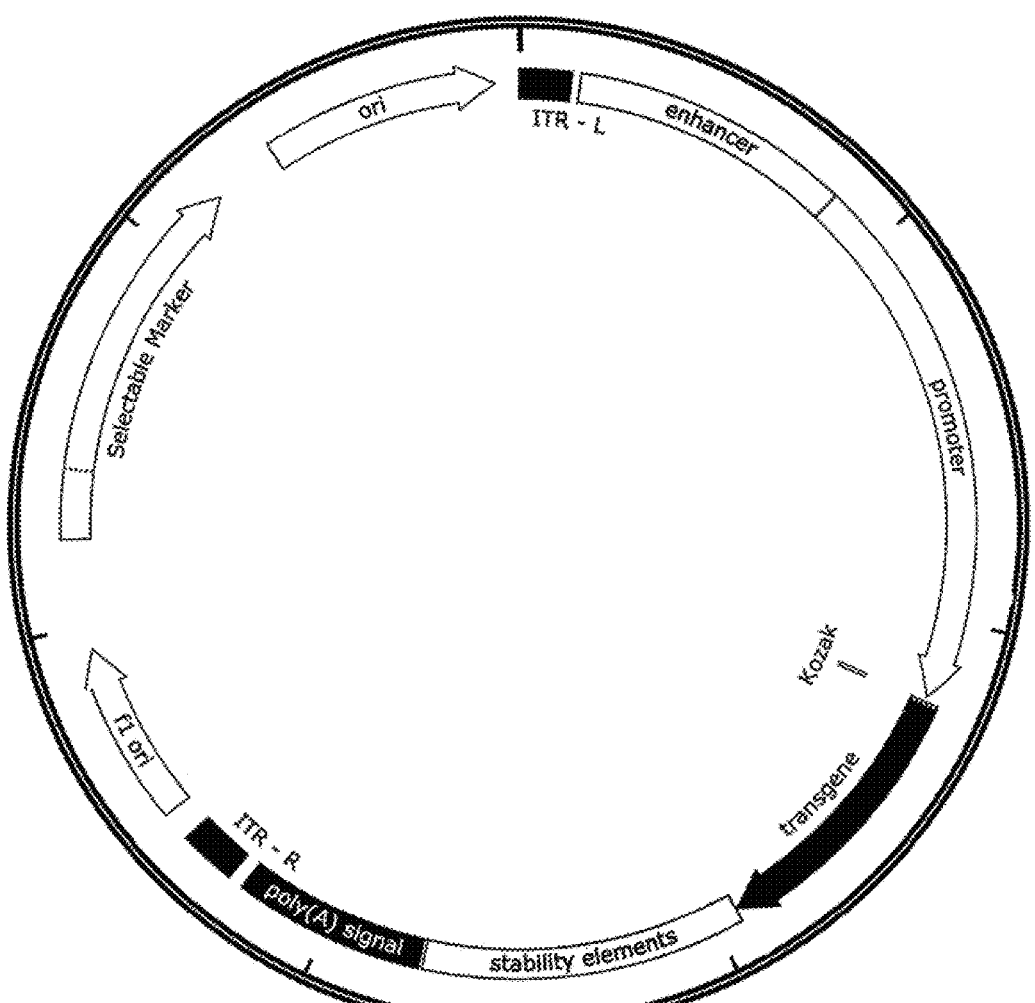
FIG. 7 illustrates a schematic of an example of an expression cassette containing REs of this disclosure, e.g., an enhancer, a promoter, and stability elements. REs can be located upstream and/or downstream of a transgene in an expression cassette, which can be a plasmid, vector, or a viral vector.

An exemplary AAV expression cassette is illustrated in FIG. 7. In some cases, the expression cassette contains a 5' AAV ITR, an enhancer (e.g., PV cell selective enhancer or one or more combined regulatory elements), a promoter (e.g., one or more PV cell selective promoters or regulatory elements), a transgene (e.g., SCN1A, SNC2A, SNC8A, SCN1B, SCN2B, KV3.1, KV3.2, KV3.3, STXBP1, or a DNA binding protein), a post-transcriptional regulatory element, and a 3' AAV ITR. The promoter can be PV cell selective, or a constitutive promoter. In some cases, the transgene is a reporter gene, e.g., a coding sequence for eGFP, RFP, or a fluorescent marker. In other cases, the transgene is a DNA binding protein that modulates gene expression.

In some cases, the transgene is a therapeutic transgene, e.g., a coding sequence for SCN1A, SNC2A, SNC8A, SCN1B, SCN2B, KV3.1, KV3.2, KV3.3, STXBP1, or a DNA binding protein, or a functional fragment or a sequence having at least 80%, at least 85%, at least 90%, at least 95%, or at least 99% sequence identity thereto. The post-transcriptional regulatory element can be any sequence which influences the expression of a protein from an mRNA or stability of an RNA, for example, an intron, an internal ribosome entry site (IRES), or a woodchuck hepatitis virus post-transcriptional regulatory element. In some cases, the post-transcriptional regulatory element is a combination of two or more post-transcriptional regulatory elements.

The expression cassette can be designed for delivery by an optimized therapeutic retroviral vector, e.g., a lentiviral vector. The retroviral vector can be a lentiviral vector comprising a left (5') LTR; sequences which aid packaging and/or nuclear import of the virus, at least one cell-type selective regulatory element, optionally a lentiviral reverse response element (RRE); optionally a promoter or active portion thereof; a transgene operably linked to one or more regulatory elements; optionally an insulator; and a right (3') retroviral LTR.

In some cases, the expression cassette comprises one or more cell-type selective regulatory elements disclosed herein. In some cases, the expression cassette comprises two or more regulatory elements combined. In some examples, the expression cassette comprises two or more regulatory elements that are not combined, for example, a promoter upstream of the transgene and an enhancer or stability element located downstream of the transgene.

In some cases, the expression cassette contains a putative cell-type selective regulatory element that has selective activity in a cell type of interest, for example, a putative PV cell selective regulatory element. The expression cassette containing the putative regulatory element can be packaged in a viral vector and transfected into an animal model to assess the activity of the putative cell-type selective regulatory element. In some cases, a putative cell type selective regulatory element can be assessed in vitro or ex vivo by delivering a vector containing the putative cell type selective regulatory element into a plurality of cells or cell types that include a target cell or cell type, and then comparing the cell type selective activity of the putative regulatory element to a control regulatory element, such as a constitutive promoter or regulatory element, or a previously known regulatory element.

In some cases, selective expression is used to selectively express a therapeutic moiety or a transgene in a cell-type of interest (or tissue-type of interest), such as PV neurons in the CNS. In some cases, a vector comprising a cell-type selective regulatory element operably linked to a transgene results in an increased selective expression of the transgene in the cell-type of interest as compared to one or more (e.g., at least two, three, four, or five) other cells, cell types, tissues, or tissue types, or results in a preferred expression of the transgene in the cell-type of interest as compared to one or more cells or cell types, e.g., at least one, two, three, four, or five non-target cell types.

Any known technique can be used to deliver the regulatory elements and a transgene, or compositions comprising regulatory elements and a transgene, to cells of interest (or a target cell or cell type) to confer or induce in vitro, in vivo, or ex vivo expression of the transgene in a cell-type selective manner.

The expression cassettes containing cell-type selective regulatory elements of this disclosure further comprise one or more transgenes. The transgenes can be protein-coding genes. In some cases, the expression cassette contains a transgene. The transgene can replace an absent or defective gene, or compensate for deficient expression of a protein inside a cell. The transgene can be involved in a cell signaling pathway. In some cases, a transgene can encode a wild-type protein, a functional fragment thereof, a variant or mutant protein having enhanced therapeutic properties, e.g., enhanced activity. In some cases, the transgene can encode a DNA binding protein comprising one or zinc finger or a domain of dCas9, an ion channel, such as a potassium ion channel or a sodium ion channel, or a subunit thereof, a neurotransmitter factor or a neurotransmitter regulator. In some cases, a transgene can encode an ion channel subunit, a variant, or a mutant thereof. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9.

The regulatory elements disclosed herein can be located at any position within an expression vector or cassette. For example, the regulatory elements can be positioned upstream of an enhancer, downstream of an enhancer but upstream of a promoter, within the 5' UTR of a transgene, within an intron in the transgene, in the 3' UTR of the transgene, or downstream of the transgene. In some cases, one or more regulatory elements are positioned upstream or downstream of the operably linked transgene.

In some examples, a regulatory element of this disclosure results in selective expression of an operably linked transgene at a level that is at least 0.5, 1.0, 1.1, 1.2, 1.3, 1.4, 1.5, 1.6, 1.7, 1.8, 1.9, 2.0, 2.5, or 3 IU/ml in a target cell type (e.g., PV cells) as measured by ELISA. In some cases, a regulatory element's ability to increase transgene expression can be assessed in a mouse wherein the total amount of transgene expression in the whole mouse and/or the total number of cell types or tissue types having transgene expression are measured.

When assessing the activity of an expression cassette or vector, the activity or expression can be represented as an activity or expression level per unit dose, or normalized to a dose of expression cassette or vector administered or delivered to a cell, mouse, or a subject. In some cases, expression or activity of a transgene is normalized to an amount of plasmid or DNA (e.g., µg/kg per mouse), or viral particles (e.g., normalized to an amount of genome copies/kg per mouse or subject) used to allow comparison across different expression vectors or cassettes with or without a regulatory element. For example, when assessing a regulatory element's activity in a mouse, selective expression or activity in PV cells assayed can be normalized to a dose of about 5, 6, 7, 8, 9, 10, 11, 12, 13, 14, 15, 16, 17, 18, 19, 20, or greater than 10 or 720 µg of expression vector, cassette, or plasmid per mouse. In some cases, the expression level or activity can be normalized to $10^{10}$, $10^{11}$, $10^{12}$, $10^{13}$, $10^{14}$, or $10^{15}$ gc/kg of viral particles containing an expression vector or cassette as disclosed herein per mouse.

In some aspects, an expression cassette comprises one or more regulatory elements (e.g., any one or more of SEQ ID NOs: 1-32, or a functional fragment or a combination thereof, or sequences having at least 80%, at least 85%, at least 90%, at least 95%, or at least 99% sequence identity thereto) disclosed herein operably linked to a transgene to result in cell-type selective expression, or preferential expression, of the transgene in a target cell type over at least one, at least two, at least three, at least four, at least five, or more than five non-target cell types. In some cases, an expression cassette comprises one or more regulatory elements operably linked to a transgene to result in cell-type selective expression or preferential expression in a target cell subtype over at least one, at least two, at least three, at least four, at least five, or more than five non-target subtypes, or all other known subtypes of the cell. In some cases, the transgene is any one of SCN1A, SNC2A, SNC8A, SCN1B, SCN2B, KV3.1, KV3.3, and STXBP1, or a functional fragment thereof, or sequences having at least 80%, at least 85%, at least 90%, at least 95%, or at least 99% sequence identity thereto. In some cases the transgene is a DNA binding protein that modulates an endogenous gene (e.g., an endogenous SCN1A, SNC2A, SNC8A, SCN1B, SCN2B, KV3.1, KV3.2, KV3.3, or STXBP1). In some cases, the transgene is any one of SEQ ID NOs: 36-43, or a functional fragment thereof, or sequences having at least 80%, at least 85%, at least 90%, at least 95%, or at least 99% sequence identity thereto. In some cases, the transgene is a transcriptional modulator. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene is a gene editing protein, such as a Cas family protein, Cas9, a zinc finger nuclease, a zinc finger nuclease, or a transcription activator-like effector nuclease. In some cases, the transgene is a reporter gene or a fluorescent marker. In some cases, an expression cassette disclosed herein is in a viral vector. In some cases, an expression cassette disclosed herein is packaged in an rAAV, such as rAAV9 or rAAVDJ. In some cases, an expression cassette disclosed herein is delivered into a cell as a gene therapy. In some cases, a gene therapy disclosed herein is delivered into a subject, preferably a human or a mammal. In some cases, an expression cassette disclosed herein is used to treat a neurological condition or disease, such as epilepsy, a neurodegenerative disease, tauopathy, neuronal hypoexcitability, Dravet syndrome or Alzheimer's disease.

In some cases, an expression cassette (e.g., gene therapy, viral vector, vector, or plasmid) comprises any one or more of SEQ ID NOs: 1-32, or a functional fragment or a combination thereof, or sequences having at least 80%, at least 85%, at least 90%, at least 95%, or at least 99% sequence identity thereto, operably linked to a transgene. In some cases, such combined regulatory elements are linked using a linker of 1-50 nucleotides. In some cases, such combined regulatory elements are not linked. In some cases, two or more regulatory elements are located upstream and/or downstream of the promoter. In some cases, two or more regulatory elements are located upstream and/or downstream of the transgene.

In some cases, an expression cassette comprises one or more regulatory elements disclosed herein, when operably linked to any transgene (e.g., a reporter transgene or a therapeutic transgene), drives selective expression or preferential expression in at least one target cell type at a level that is statistically significantly higher than the expression driven by CAG, EF1α, a constitutive promoter, or a non-selective regulatory element when operably linked to the same transgene, or by the same construct without the regulatory elements. In some cases, statistically significantly higher means the regulatory elements drive selective expression in the target cell type at a level that is at least 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, or 100 times the expression level by CAG, EF1α, a constitutive promoter, or a non-selective regulatory element when operably linked to the same transgene in the target cell type, or by the same construct without the regulatory elements. In some cases, such cell-type selective expression is assayed using a co-localization assay as described herein.

In other aspects, an expression cassette comprising one or more regulatory elements disclosed herein operably linked to any transgene disclosed herein results in selective expression or preferential expression of the transgene in a target cell type over at least one, at least two, at least three, at least four, at least five, or more than five non-target cell types or non-target subtypes.

In some instances, the target cell type is a PV cell. In some cases, the non-target cell subtypes are at least one, at least two, at least three, or at least four of the non-PV GABAergic subtypes disclosed herein. In some cases, an expression cassette comprising a regulatory element disclosed herein is selective for PV cells over all non-PV GABAergic cells or all non-PV CNS cells. In some cases, cell-type selectivity is measured according to a co-localization assay disclosed herein. In some cases, cell-type selectivity is measured using a mouse that expresses Cre in the target cell type.

Parvalbumin (PV) Neurons

GABAergic neurons produce gamma aminobutyric acid (GABA), the main inhibitory neurotransmitter in the CNS. GABA is important for reducing neural excitability throughout the nervous system. GABA acts at inhibitory synapses by binding specific transmembrane receptors and causing the opening of ion channels which negatively change the membrane polarization. This generally results in hyperpolarization of the cell and increases the signal required to trigger an action potential. Defects in GABAergic neurons can result in an imbalance between excitatory and inhibitory signaling, and have been implicated in many neurological diseases, including Dravet syndrome, epilepsy, neurodegeneration, tauopathies and Alzheimer's disease. Other neurological conditions or diseases implicated include a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); and/or neurodegeneration (e.g., Alzheimer's disease, Parkinson's disease). In some cases, the neurological condition or disease is any seizure and/or epilepsy related condition or disease wherein PV neurons are implicated.

Parvalbumin is a calcium-binding protein, which is expressed in about 40% of total GABAergic interneurons in the somatosensory cortex. Within the CNS, PV cells are generally considered GABAergic cells. Various studies have also identified GABAergic cells to include distinct subtypes of cells, including cells that express PV, SOM, CR, CCK, NPY, VIP, or a combination thereof.

PV neurons are particularly relevant for various neurological diseases or conditions, such as Dravet syndrome, Alzheimer's disease, epilepsy, neurodegeneration, tauopathies and/or seizures. In some cases, a PV neuron-associated neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated. In various aspects, the target cell is PV cells in the CNS, or GABAergic cells that express PV.

In various aspects, PV-expressing interneurons are also called basket cells, which can be further subdivided by size of the cell body (e.g., large basket cell, small basket cell, and nest basket cell), and dendritic and axonal projection. Physiologically, PV-expressing basket cells are often fast-spiking (FS), characterized by a high-frequency train of action potentials (APs) with little adaptation. It is widely accepted that PV basket neurons innervate the soma and proximal dendrites of excitatory pyramidal neurons. Feedforward inhibition mediated through FS PV-expressing basket neurons can be found in several cortical networks including thalamocortical, translaminar, and interareal circuits. FS PV basket neurons strongly inhibit neighboring excitatory pyramidal neurons. It has been shown that PV basket neurons and pyramidal neurons that share common excitatory inputs tend to be reciprocally connected (feedback inhibition). These connections can serve to regulate the precise time window in which the excitatory neurons can generate spikes in response to excitatory drives. In addition, thalamocortical and intracortical excitatory inputs onto FS PV basket neurons are depressed by high frequency stimulation, which mediates activity-dependent feedforward inhibition. PV-expressing basket cells also innervate other interneurons including other basket cells, and are electrically coupled with each other through gap junctions. It has been proposed that this feature may help to generate and maintain cortical network synchronization and oscillation.

In some cases, one or more regulatory elements disclosed herein result in increased selectivity in gene expression in PV neurons as compared to at least one, at least two, at least three, at least four, or at least five non-PV expressing neurons. In some cases, non-PV cells include all non-PV GABAergic cells. In some cases, non-PV GABAergic neurons include, but are not limited to, calretinin (CR), somatostatin (SOM), cholecystokinin (CCK), CR+SOM, CR+neuropeptide Y (NPY), CR+vasointestinal polypeptide (VIP), SOM+NPY, SOM+VIP, VIP+choline acetyltransferase (ChAT), CCK+NPY, CR+SOM+NPY, and CR+SOM+VIP expressing cells.

In some cases, any one of CAG, EF1α, a constitutive promoter (e.g., SV40, CMV, UBC, PGK, and CBA), or a non-selective regulatory element that drives gene expression in a non-cell type selective manner can be used for comparison with PV selective regulatory elements, or any cell type selective regulatory elements, disclosed herein. In some cases, a regulatory element that results in selective expression in PV cells at a level above the expression of a gene operably linked to CAG or EF1a control is indicative of selectivity to PV cells. In some cases, a regulatory element disclosed herein shows selective gene expression in PV cells that is at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% higher than the PV expression level from a transgene that is operably linked to CAG, EF1α, a constitutive promoter (e.g., SV40, CMV, UBC, PGK, and CBA), or a non-selective regulatory element (e.g., SEQ ID NO: 34, or a functional fragment thereof, or a sequence having at least 80%, at least 85%, at least 90%, at least 95%, or at least 99% sequence identity thereto), and as measured in a co-localization assay. In some cases, a regulatory element disclosed herein shows a selective gene expression in PV cells that is at least 1.5 fold, at least 2 fold, at least 3 fold, at least 4 fold, at least 5 fold, at least 6 fold, at least 7 fold, at least 8 fold, at least 9 fold, or at least 10 fold the expression level under CAG, EF1α, a constitutive promoter (e.g., SV40, CMV, UBC, PGK, and CBA), or a non-selective regulatory element (e.g., SEQ ID NO: 34, or a functional fragment thereof, or a sequence having at least 80%, at least 85%, at least 90%, at least 95%, or at least 99% sequence identity thereto) and as measured in a co-localization assay described herein.

In preferred cases, one or more regulatory elements described herein selectively drive expression of a transgene in a GABAergic cell, such as a GABAergic cell that expresses parvalbumin over at least one other CNS cell type (e.g., at least two, at least three, at least four, at least five non-PV cells, or two or more, three or more, or four or more non-PV cells and/or non-PV GABAergic neurons).

In some cases, a target cell type is a GABAergic neuron that expresses parvalbumin, or PV cells.

One way of selectively expressing a transgene within a subpopulation of cells in the brain is to use a viral vector comprising a transgene operably linked to a cell-type selective regulatory element, or a regulatory element that is selective (or has selective activity) in the subpopulation of cells in the brain, e.g., PV cells. A viral vector can be selected to have high infectivity without selectivity for a particular cell type, while the regulatory element confers selectivity. For example, a cell-type selective regulatory element can drive expression of a transgene in PV neurons and not in other neurons.

In some cases, the present disclosure involves the use of regulatory elements (i.e., PV cell selective regulatory elements) that selectively drive expression in PV neurons.

GABAergic cells are inhibitory neurons which produce gamma-aminobutyric acid. GABAergic cells can be identified by the expression of glutamic acid decarboxylase 2 (GAD2). Other markers of GABAergic cells include GAD1, NKX2.1, DLX1, DLX5, SST, PV and VIP.

In some instances, a non-PV CNS cell is an excitatory neuron, a dopaminergic neuron, an astrocyte, a microglia, a motor neuron or a vascular cell. In some instances, a non-GABAergic neuron is a cell that does not express one or more of GAD2, GAD1, NKX2.1, DLX1, DLX5, SST and VIP. In some instances, a non-PV neuron is a GABAergic neuron that does not express parvalbumin. In some instances, other CNS cells refer to CNS cell types that have never expressed any of PV, GAD2, GAD1, NKX2.1, DLX1, DLX5, SST and VIP.

In some instances, a regulatory element disclosed herein is selective for a PV expressing cell over at least one, two, three, four, five, or more than five non-PV CNS cell-types. In some cases, non-PV cell types include non-PV GABAergic cells. In some cases, the cell type of interest is a PV cell. In some cases, REs selective for PV cells are referred to as PV cell selective regulatory elements.

In some cases, the PV cell selective regulatory elements disclosed herein include the sequences of SEQ ID NOs: 1-32, or any combination thereof.

In some cases, one or more PV cell selective regulatory elements or one or more regulatory elements disclosed herein are used to increase expression of a transgene in PV-expressing cells by at least 2, 5, 10, 15, 20, 30, 40, 50, 60, 70, 80, 90, 100, or more fold as compared to expression without the regulatory element. In some cases, a RE in an expression cassette increases gene expression by at least 1.5%, 2%, 5%, 10%, 15%, 20%, or 50%, or more than 1.5%, 2%, 5%, 10%, 15%, 20%, 25%, 30%, 35%, 40%, 45%, 50%, 55%, 60%, 65%, 70%, 75%, 80%, 85%, 90%, 95%, or 100% as compared to expression without the regulatory elements. In some cases, compositions and methods of use thereof comprise expression cassettes containing one or more regulatory elements that result in a 10-500% increase in transgene expression, e.g., expression of SCN1A, SNC2A, SNC8A, SCN1B, SCN2B, KCNC1 (also known as KV3.1), KCNC3 (also known as KV3.3), STXBP1, a DNA binding protein, or a variant or functional fragment thereof, or a protein thereof, as compared to the level without the regulatory elements or as compared to a non-selective regulatory element (e.g., CAG, EF1α, a constitutive promoter, or SEQ ID NO: 34, or a functional fragment thereof, or a sequence having at least 80%, at least 85%, at least 90%, at least 95%, or at least 99% sequence identity thereto). In some cases, the increase in gene expression and/or protein level of any one of SCN1A, SNC2A, SNC8A, SCN1B, SCN2B, KCNC1, KCNC3, and STXBP1 is 1.5-5%, 5%-10%, 10-15%, 15-20%, 20-30%, 30-40%, 40-50%, 50-60%, 60-70%, 70-80%, 80-90%, 90-100%, 100-150%, 150-200%, 250-300%, 300-350%, 350-400%, 400-450%, 450-500%, or 1.5-20%, 20%-50%, 50%-100%, 100-200%, 200-300%, 300-400%, or 400-500% as compared to the level without the expression cassette or regulatory elements. In some cases, such gene or protein expression is selective in PV cells as compared to an expression cassette comprising a control (e.g., CAG, EF1α, a constitutive promoter (e.g., SV40, CMV, UBC, PGK, and CBA), or a non-selective regulatory element) or a non-cell type selective regulatory element (e.g., SEQ ID NO: 34, or a functional fragment thereof, or a sequence having at least 80%, at least 85%, at least 90%, at least 95%, or at least 99% sequence identity thereto).

In some cases, selectivity of expression in PV cells can be calculated by dividing the number of cells that express both PV and eGFP (the transgene operably linked to one or more regulatory elements) by the total number of cells that express eGFP, and multiplying by 100 to convert into a percentage. PV cell selective regulatory elements as described herein can be highly selective for expression in PV cells. For example, PV cell selective regulatory elements or one or more regulatory elements disclosed herein can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons.

In some cases, a PV cell selective regulatory element or any regulatory element disclosed herein confers selectivity in expressing a transgene in PV neurons at a level that is statistically higher than a control regulatory element, e.g., EF1a or a previously known regulatory element. In some instances, the statistical difference between a PV cell selective regulatory element and a control regulatory element is at least 2 fold, 5 fold, 10 fold, 20 fold, or more than 2 fold difference, or more than 5 fold, 10 fold, or 20 fold difference as determined by any one of the methods described herein, such as a co-localization assay.

The present disclosure includes regulatory elements that are selective for PV cells. These PV cell selective REs or any cell type selective REs are preferably short, preferably less than about 1100 base pairs, 1000 bp, 900 bp, 800 bp, 700 bp, 600 bp, 500 bp, 400 bp, 300 bp, 200 bp, or less than about 110 bp. The PV cell selective REs or any cell type selective REs can be between 1050 bp and 100 bp, between 100 bp and 500 bp, or between 500 bp and 1050 bp. Some examples of PV cell selective regulatory elements are provided by SEQ ID NOs 1-32, or a functional fragment or combination thereof. Other PV cell selective regulatory elements contemplated by the present disclosure include sequences having at least 80%, at least 85%, at least 90%, at least 95%, or at least 99% sequence identity to any of these sequences described herein, or a part or fragment of one of the sequences described herein.

In some cases, a PV cell selective regulatory element or any regulatory element disclosed herein has at least about 70%, 80%, 85%, 90%, 91%, 92%, 93%, 94%, 95%, 96%, 97%, 98%, 99% or more than 99% identity to a sequence described herein, or a fragment of a sequence described herein. In some cases, a PV cell selective regulatory element has at least about 80% identity to at least about 30%, 40%, 50%, 60%, 70%, 80%, 90% or 95% of a sequence described herein, or a functional fragment thereof.

In some cases, a PV cell selective regulatory element comprises at least 80% identity to any one or more of SEQ ID NOs: 1-32, or a functional fragment or a combination thereof, or sequences having at least 80%, at least 85%, at least 90%, at least 95%, or at least 99% sequence identity thereto. In some cases, a PV cell selective regulatory element has 90% identity to 50% or more of a sequence of SEQ ID NOs: 1-22. In some instances, a PV-selective regulatory element is a functional fragment of any of SEQ ID NOs: 1-32 or a combination thereof. In some cases, the functional fragment is able to selectively express a transgene in PV cells with at least 50%, 55%, 60%, 65%, 70%, 75%, 80%, 85%, 90%, 95%, or greater than 95% selectivity of expression in PV cells.

In some cases, two or more PV cell selective regulatory elements of this disclosure or any two or more regulatory elements disclosed herein are combined to form combination regulatory elements. In some instances, two or more, three or more, four or more, five or more, six or more, seven or more, eight or more, nine or more, or ten or more PV cell selective regulatory elements, or a plurality of regulatory elements disclosed herein, are combined. For example, SEQ ID NO: 31 is a combination of SEQ ID NOs 1 and 23-29. As another example, SEQ ID NO: 32 is a combination of SEQ ID NO: 8 and SEQ ID NO: 23-29. In some cases, fragments of two or more PV-selective regulatory elements can be combined to form a combination regulatory element. For example, 50% of SEQ ID NO: 1 can be combined with 30% of SEQ ID NO: 8 and 90% of SEQ ID NO: 30 to form a combination regulatory element.

In some cases, one or more PV cell selective regulatory elements of this disclosure or any one or more regulatory elements disclosed herein selectively express an operably linked transgene in PV neurons as compared to one or more other CNS cell types. This selective expression can be quantified by counting the number of PV neurons which express detectable levels of the linked transgene as a percentage of the total number of cells expression the transgene, including the number of non-PV neurons which express the transgene. In other words, selectivity of a PV regulatory element in a particular cell type or target cell can be determined by measuring and/or comparing the number of PV neurons (or target cells) expressing the transgene that is operably linked to the regulatory element relative to the number of non-target cell types that express the transgene (or the total number of cells expressing the transgene).

In some cases, PV cell selective regulatory elements can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons, PV neurons in the CNS, or GABAergic neurons that also express PV. In some cases, one or more regulatory elements of this disclosure can exhibit about 50%, 55%, 60%, 65%, 70%, 75%, 80%, 85%, 90%, 91%, 92%, 93%, 94%, 95%, 96%, 97%, 98%, 99%, or greater than about 99% selectivity for PV neurons as compared to CAG or EF1a or non-cell-type selective element, or as compared to non-PV CNS cells, or as compared to at least one, at least two, at least three, at least four, or at least five other non-PV GABAergic neuronal sub-types in the CNS.

In some cases, a PV selective regulatory element confers selectivity in expressing a transgene in PV neurons at a level that is statistically higher than a control regulatory element, e.g., CAG, EF1α, a constitutive promoter (e.g., SV40, CMV, UBC, PGK, and CBA), a non-selective regulatory element, or a previously known regulatory element. In some instances, the statistical difference between a PV cell selective RE and a control element is at least 2 fold, 5 fold, 10 fold, 20 fold, or more than 2 fold difference, or more than 5 fold, 10 fold, or 20 fold difference as determined by any one of the methods described herein. In some cases, the selectivity in PV is measured using a co-localization assay as described herein.

In some aspects, the cell-type selective regulatory elements described herein are useful for selectively modulating expression of a transgene in a CNS cell type compared to other CNS cell types. For example, the cell-type selective regulatory elements described herein can be useful for selectively modulating expression of a transgene in PV cells over other CNS cells, including other types of neurons. For gene therapy, selective expression of a transgene in a target cell type and/or minimized expression of the transgene in a non-target cell type can be desired. Expression of the transgene in an unintended cell-type (e.g., non-target cell type) can result in an adverse effect to the subject. Expression of the transgene in an unintended cell-type can counteract the therapeutic effect of the transgene in the intended cell type. For example, a transgene intended for expression in PV cells can have a negative effect for the subject if expressed in glutamatergic neurons. The cell-type selective regulatory elements described herein can be used in expression cassettes to ensure appropriate expression of a transgene and/or to reduce off-target effects of gene therapy.

The cell-type selective regulatory elements herein can be used in gene expression cassettes whereby they are operably linked to one or more transgenes. Such gene expression cassettes are used to deliver transgenes into cells for expression. The expression cassette can contain a cell-type selective regulatory element as described herein, a combination of cell-type selective regulatory elements, or a fragment of a cell-type selective regulatory element as described herein operably linked to a transgene.

Preferably, the expression cassettes herein include one or more cell-type selective regulatory elements operably linked to a transgene, whereby the two do not function together in their endogenous context in vivo. For example, a transgene for sodium ion channel beta subunit, such as SCN1B, can be operably linked to one or more regulatory elements that do not function in the same context in vivo, or do not detectably drive expression of SCN1B endogenously. Similarly, a nucleic acid cassette can include a neurotransmitter regulator, such as STXBP1, operably linked to a regulatory element that does not function in the same context endogenously or in vivo, or is not in the same open reading frame, or is not on the same human chromosome, or does not detectably drive expression of STXBP1 in vivo. In some cases, a cell-type selective regulatory element is linked to a transgene, wherein the cell-type selective regulatory element does not regulate the endogenous gene corresponding to the transgene in vivo.

In some aspects, cell-type selective regulatory elements disclosed herein are derived from sequences isolated from a human chromosomal locus different from a locus of a native gene corresponding to the transgene. Thus, in some instances, an expression cassette comprises cell-type selective regulatory element(s) having a sequence derived from a chromosome different from the chromosome corresponding to the transgene on the same cassette. In other instances, regulatory element(s) of the disclosure and a transgene that are operably linked in an expression cassette are derived from sequences located more than 20 kb apart in the human genome, or at distal genomic locations. When two or more human derived regulatory elements are utilized on an expression cassette, the two or more regulatory elements can have sequences located more than 5 kb apart, more than 10 kb apart, more than 15 kb apart, or more than 20 kb apart in the human genome, or wherein the two or more regulatory elements do not interact with each other naturally in the genome.

In some cases, an expression cassette comprising PV-selective regulatory elements can exclude known sequences derived from hSyn1 or GAD2 promoter sequences. In some instances, the PV-selective regulatory elements do not comprise the full promoter sequence of any one of the GAD2, GAD1, SYN1, NKX2.1, DLX1, DLX5, SST and VIP promoters. In some instances, the PV-selective regulatory elements do not comprise more than 500 contiguous base pairs of sequence derived from the promoter or one or more of GAD2, GAD1, SYN1, NKX2.1, DLX1, DLX5, SST and VIP. In some instances, the PV-selective regulatory elements do not comprise sequences which are within 1 kb, 2 kb, 3 kb, 4 kb, 5 kb, 6 kb, 7 kb, 8 kb, 9 kb, or 10 kb of the transcription start site of any one of GAD2, SYN1, NKX2.1, DLX1, DLX5, SST, and VIP.

In some cases, a transgene is useful to treat a disease associated with a specific cell type of interest. In some cases, a cell type of interest is a neuron, an inhibitory neuron, a GABAergic neuron, or a PV neuron. In some cases, a transgene is any one or more of SCN1A, SNC2A, SNC8A, SCN1B, SCN2B, KV3.1, KV3.3, and STXBP1. In some cases, a transgene is a DNA binding protein that modulates expression of a gene (e.g., a transcriptional activator or a transcriptional repressor that modulates expression of an endogenous gene). In some cases, a transgene is a gene editing protein, such as a zinc finger nuclease, a transcription activator-like effector nuclease, a Cas family protein. In some cases, a transgene is a reporter gene or a detectable marker, such as eGFP, tdTomato, or RFP. In some cases, a transgene is a Cas protein, such as Cas9.

Transgenes useful to treat a condition associated with PV neuron cells can be incorporated in a vector, nucleic acid cassette, or method as described herein. Transgenes used herein generally do not contain introns, or do not contain more than one intron. A transgene can be obtained from a cDNA sequence rather than from genomic sequence. In some cases, transgenes can contain some, or all, of their endogenous introns. In some examples, such a transgene encodes for a DNA binding domain or an ion channel. Examples of DNA binding domains that can be encoded for in the expression cassettes of this disclosure include zinc fingers, Cas9, a Cas family protein, dCas9, a dCas family protein or a transcriptional activator like effector (TALE). In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene comprises a gene editing protein, e.g., a Cas protein, Cas9. In some cases, the transgene is a subunit or a component of an ion channel or a membrane protein, or a gene associated with a neurological condition or disease disclosed herein. Examples of ion channel transgenes which can be used in the expression cassettes of this disclosure include voltage gated and ligand gated ion channels. Voltage gated ion channels include sodium channels, calcium channels, potassium channels, and proton channels. In some instances, the transgene codes for a subunit of a voltage gated sodium channel. Examples of voltage gated sodium channel subunits include SCN1B (NM_001037.4), SCN1A (NM_001165963.1), and SCN2B, (NM_004588.4).

In some instances, the transgene codes for a subunit of a voltage gated potassium channel. Examples of voltage gated sodium channel subunits include KCNC1 (NM_001112741.1), and KCNC3 (NM_004977.2). In some cases, a transgene is any one or more of SCN1A, SNC2A, SNC8A, SCN1B, SCN2B, KV3.1, KV3.3, STXBP1, a variant and a functional fragment thereof. In some cases, a transgene is a sequence having at least 80%, at least 85%, at least 90%, at least 91%, at least 92%, at least 93%, at least 94%, at least 95%, at least 96%, at least 97%, at least 98%, at least 99%, or at least 99.5% sequence identity to any one of SCN1A, SNC2A, SNC8A, SCN1B, SCN2B, KV3.1, KV3.3, STXBP1, a variant or a functional fragment thereof. In some cases, such sequence identity is measured using BLAST.

In some cases, an expression cassette disclosed herein comprises one or more PV-selective regulatory elements or one or more regulatory elements of this disclosure operably linked to a transgene having at least 80%, at least 85%, at least 90%, at least 91%, at least 92%, at least 93%, at least 94%, at least 95%, at least 96%, at least 97%, at least 98%, at least 99%, or at least 99.5% sequence identity to a sequence encoding any one of SEQ ID NOs: 37-43, or a functional fragment or variant thereof, or the GenBank sequences corresponding to SEQ ID NOs: 37-43. In some cases, an expression cassette disclosed herein comprises a transgene having a sequence according to (i) a sequence of SEQ ID NOs: 37-43, or (ii) a functional fragment thereof, or (iii) a sequence having at least 80%, at least 85%, at least 90%, at least 91%, at least 92%, at least 93%, at least 94%, at least 95%, at least 96%, at least 97%, at least 98%, at least 99%, or at least 99.5% sequence identity to (i) or (ii).

In some examples, the transgene is a neurotransmitter regulator, or a variant or functional fragment thereof. A neurotransmitter regulator may be involved in regulating production or release of a neurotransmitter in the CNS. For example, a neurotransmitter regulator may assist with synaptic fusion to release neurotransmitters. An example of a neurotransmitter regulator is STXBP1 (NM_001032221.3) or a functional fragment thereof, or a sequence having at least 80%, at least 85%, at least 90%, at least 95%, or at least 99% sequence identity thereto. The transgene may also be a subunit of a neurotransmitter regulator.

In some case, an expression cassette of this disclosure can contain an AAV2 5' ITR, a PV-selective enhancer, a PV-selective promoter, or a combination of one or more PV-selective promoters and enhancers, a cDNA of SCN1B, a WPRE, a hGH polyA signal, PV-selective regulatory element, and an AAV2 3'ITR. In one example, the expression cassette comprises an AmpR promoter, and AmpR coding sequence, a bacterial origin of replication, an AAV2 ITR, SEQ ID NO: 8, SEQ ID NOs: 23-29, a transgene (coding sequence, a WPRE, a human growth hormone polyA signal, a AAV2 ITR, and an f1 origin.

As another example, an expression cassette of this disclosure can contain an AAV2 5' ITR, an enhancer, a promoter, a transcriptional activator of the endogenous SCN1A gene, a WPRE, a hGH polyA signal, a regulatory element, and an AAV2 3'ITR. In some cases, an expression cassette comprises AAV2 5' ITR, a promoter, an intronic element, transcriptional modifier, synthetic polyA, and an AAV2 3' ITR. In some cases, an expression cassette of this disclosure can contain an AAV2 5' ITR, a PV-selective enhancer, a PV-selective promoter, a sequence encoding a transcriptional activator of SCN1A or SCN1B, a WPRE, a hGH polyA signal, a PV-selective regulatory element or any of the regulatory elements disclosed herein, and an AAV2 3'ITR.

An expression cassette comprising one or more regulatory element of this disclosure can be used to treat a medical condition. In some cases, an expression cassette containing a regulatory element of this disclosure is used to treat a neurological condition or a neurodegenerative condition. The neurological condition can be caused by a known genetic event or may have an unknown cause.

The neurological condition can be a disease associated with PV neurons. The neurological condition can be a disease associated with inhibitory neurons, such as PV neurons. Diseases or conditions associated with PV neurons can be treated by delivering an expression cassette carrying a transgene and one or more PV cell-selective regulatory elements or any of the regulatory elements as described herein to a cell in vivo. In some aspects, expression cassettes comprising a transgene operably linked to one or more PV cell-selective regulatory elements or any of the regulatory elements disclosed herein can be used to treat Dravet syndrome, Alzheimer's disease, epilepsy, a neurodegenerative disorder, tauopathy, neuronal hypoexcitability and/or seizures. In some cases, an expression cassette of this disclosure is used to treat a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis); and/or neurodegeneration (e.g., Alzheimer's disease, Parkinson's disease). In some cases, the neurological condition or disease is any seizure and/or epilepsy related condition or disease wherein PV neurons are implicated.

Majority of Dravet syndrome cases is associated with mutations in the SCN1A and/or SCN2A genes. Mutations or abnormalities in SCN1A has also been associated with seizure disorders, epilepsy, autism, familial hemiplegic migraine type 3 (FHM3), genetic epilepsy with febrile seizures plus (GEFS+), and effectiveness of certain anti-seizure medications. For instance, ICS5N+5G>A mutation in SCN1A is associated with the maximum safe amount (dose) of the anti-seizure drugs phenytoin and carbamazepine.

In some Alzheimer's patients, production of amyloid β (Aβ) involving many peptides and proteases that can affect excitability of neurons, causing seizures and downregulation of the Nav1.1 sodium channel in PV neurons.

Diseases associated with dysfunctional PV neurons such as those due to loss of function mutations in SCN1A or Nav1.1 include: Dravet syndrome, Ohtahara syndrome, epilepsy, early infantile epileptic encephalopathy 6 (EIEE6), familial febrile seizures 3A (FEB3A), intractable childhood epilepsy with generalized tonic-clonic seizures (ICEGTC), migraine, familial hemiplegic 3 (FHM3), Panayiotopoulos syndrome, familial atrial fibrillation 13 (ATFB13), generalized epilepsy with febrile seizures plus type 1 (gefs+ type 1), Brugada syndrome, nonspecific cardiac conduction defect, generalized epilepsy with febrile seizures plus, benign familial infantile seizures, early infantile epileptic encephalopathy11 (EIEE11), benign familial infantile epilepsy, neurodegeneration, tauopathies and Alzheimer's disease. In some cases, the neurological condition is Dravet syndrome. Dravet syndrome is associated with mutations in the SCN1A and/or SCN2A genes. In some cases, one or more regulatory elements of this disclosure are used in a gene therapy or an expression cassette to treat a neurological condition or disease associated with PV neurons, e.g., a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, one or more regulatory elements of this disclosure (e.g., PV neuron selective regulatory elements) are used to treat Dravet syndrome and/or Alzheimer's disease (e.g., in an expression cassette, a vector, or a gene therapy). In some cases, the neurological condition or disease is any seizure and/or epilepsy related condition or disease wherein PV neurons are implicated.

Methods and compositions of this disclosure can be used to treat a subject who has been diagnosed with a disease, for example, a neurological or neurodegenerative disease. The subject can be a patient suffering from a form of epilepsy. In some instances, the subject is a patient with Dravet syndrome. The subject can be a patient suffering from a neurodegenerative disease, for example, a patient with Alzheimer's disease. In some instances, epilepsy, encephalopathy, and/or seizures are associated with a genetic mutation in SCN8A. In some cases, a genetic mutation in SCN8A can give rise to epilepsy syndromes, e.g., Dravet syndrome. In some instances, a genetic mutation in STXBP1 is associated with encephalopathy with epilepsy, characterized by recurrent seizures.

In some instances, a subject treated with one or more compositions described herein is one diagnosed with a mutation or genetic aberration in an ion channel or a neurotransmitter regulator (e.g., a syntaxin binding protein). Examples of such mutations include mutations in SCN1A, SNC2A, SNC8A, SCN1B, SCN2B, KCNC1, KCNC3, and/or STXBP1, or combination thereof. The expression cassette containing a cell-type selective regulatory element as described herein can be delivered to a subject to treat or prevent a disease with symptoms associated with a specific cell type. For example, an expression cassette comprising a transgene operably linked to one or more PV cell selective regulatory element is delivered to a subject who has symptoms, or is at risk of developing symptoms, associated with PV neurons.

In some cases, the treatment can be administered to a subject with, or at risk of developing, Dravet syndrome. Symptoms associated with Dravet syndrome include seizures, memory defects, developmental delay, poor muscle tone and/or cognitive problems. Treatment with an expression cassette of this disclosure can result in an improvement of one or more symptoms, such as a reduction in number, duration, and/or intensity of seizures. Administration of a gene therapy as described herein to a subject at risk of developing Dravet syndrome can prevent the development of or slow the progression of one or more symptoms.

In another example the treatment may be administered to a subject suffering from Alzheimer's disease. Symptoms associated with Alzheimer's disease include short term memory loss, cognitive difficulties, seizures, and difficulties with language, executive functions, perception (agnosia), and execution of movements (apraxia). Treatment with an expression cassette of this disclosure can result in an improvement of one or more Alzheimer's disease symptoms, such as a reduction in progression of memory loss, or the prevention of one or more symptoms. In some cases, the treatment can result in a correction of high gamma power brain activity. The treatment can result in a decrease in seizure frequency and/or seizure severity, or a decrease in high gamma power activity by 10%, 20%, 30%, 40%, 50%, 60%, or 70%. In some cases, the treatment can result in an improvement in cognitive function. Learning and/or memory can be improved by 10%, 20%, 30%, 40%, 50%, 60%, 70%, 80%, 90%, 100% or more than 100%.

Methods and compositions of this disclosure can be used to treat a subject who is at risk of developing a disease. The subject can be known to be predisposed to a disease, for example, a neurological disease or a disease associated with epilepsy, seizures, and/or encephalopathy. The subject can be predisposed to a disease due to a genetic event, or due to known risk factors. For example, a subject can carry a mutation in SCN1A which is associated with Dravet syndrome. In some cases the subject can be predisposed to a disease such as Alzheimer's disease due to the age of the subject.

The treatment can result in a decrease or cessation of symptoms. For example, treatment can improve learning, memory, cognitive function, and/or motor function; reduce frequency and/or duration of seizures; and/or reduce temperature sensitivity (or increase the temperature threshold for triggering a seizure).

In some instances, the target cell type of a gene therapy or expression cassette disclosed herein is a PV cell. In some cases, the non-target cell subtypes are at least one, at least two, at least three, or at least four of the non-PV GABAergic subtypes disclosed herein. In some cases, an expression cassette comprising a regulatory element disclosed herein is selective for PV cells over all non-PV CNS cells. In some cases, cell-type selectivity is measured according to a co-localization assay disclosed herein. In some cases, cell-type selectivity is measured using a mouse that expresses Cre in the target cell type.

In some instances, the treatment does not result in an adverse reaction for the subject. Treatment with a gene therapy containing a PV-selective regulatory element can cause fewer, or less severe, adverse reactions in a subject than treatment with a similar gene therapy containing the same transgene linked to a non-selective regulatory element.

In various aspects, any expression cassette disclosed herein can be adapted for or used in a gene therapy (e.g., rAAV or rAAV9 gene therapy) to treat any one or more of Dravet syndrome, Alzheimer's disease, epilepsy, neurodegeneration, tauopathy, neuronal hypoexcitability and/or seizure. In some cases, a gene therapy comprises any one or more, two or more, three or more, four or more, five or more, six or more, seven or more, eight or more, nine or more, or ten or more of SEQ ID NOs: 1-32, or a functional fragment or a combination thereof, or sequences having at least 80%, at least 85%, at least 90%, at least 95%, or at least 99% sequence identity thereto, operably linked to a transgene. In some cases, a gene therapy comprises an expression cassette of this disclosure. In some cases, a gene therapy comprises one or more regulatory elements disclosed herein operably linked to any transgene (e.g., a reporter transgene or a therapeutic transgene) such that the regulatory elements drive selective expression or preferential expression in at least one target cell type at a level that is statistically significantly higher than the expression driven by CAG or EF1α or a non-selective regulatory element when operably linked to the same transgene, or by the same construct without the regulatory elements. In some cases, statistically significantly higher means the regulatory elements drive selective expression in the target cell type at a level that is at least 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, or 100 times the expression level by the CAG, EF1α, a constitutive promoter, or a non-selective regulatory element when operably linked to the same transgene in the target cell type, or by the same construct without the regulatory elements. In some cases, such cell-type selective expression is assayed using a co-localization assay as described herein. In some cases, the transgene is any one or more of SCN1A, SNC2A, SNC8A, SCN1B, SCN2B, KV3.1, KV3.3, STXBP1, and a functional fragment thereof. In some cases, the transgene is a DNA binding protein that modulates expression of an endogenous gene, such as a transcriptional modulator, a transcriptional activator, or a transcriptional repressor. In some cases, the transgene is a DNA binding protein that comprises a DNA binding domain of a DNA binding protein or a DNA cleaving protein (e.g., a nuclease, a restriction enzyme, a recombinase, etc.) wherein the DNA cleaving domain or nuclease domain has been deactivated, e.g., a nuclease-deactivated Cas (dCas), a deactivated transcription activator-like effector nuclease, or a nuclease-deactivated zinc finger protein. In some cases, the DNA binding domain is linked to a transcriptional modulating domain (e.g., a transcriptional activator or repressor domain). In some cases, the transgene is a gene editing protein, such as a zinc finger nuclease or a transcription activator-like effector nuclease. In some cases, a transgene is a reporter gene or a detectable marker, such as eGFP, tdTomato, or RFP. In some cases, a transgene is a Cas protein, such as Cas9.

In some cases, a gene therapy comprising an expression cassette disclosed herein is used to treat a neurological condition or disease. In some cases, a gene therapy comprising an expression cassette disclosed herein is used to treat a neurological condition or disease, wherein the expression cassette comprises any one or more, two or more, three or more, four or more, five or more, six or more, seven or more, eight or more, nine or more, or ten or more of SEQ ID NOs: 1-32, or a functional fragment or a combination thereof, or sequences having at least 80%, at least 85%, at least 90%, at least 95%, or at least 99% sequence identity thereto, operably linked to a transgene. In some cases, the transgene is any one or more of SCN1A, SNC2A, SNC8A, SCN1B, SCN2B, KV3.1, KV3.3, STXBP1, a DNA binding protein and a functional fragment thereof. In some cases, a gene therapy comprising an expression cassette disclosed herein is used to treat Dravet syndrome. In some aspects, a gene therapy comprising an expression cassette disclosed herein is used to treat Alzheimer's disease. In some cases, a gene therapy comprising an expression cassette disclosed herein is used to treat epilepsy and/or seizure symptoms associated with Dravet syndrome and/or Alzheimer's disease. In some cases, treating any one of Dravet syndrome, Alzheimer's disease, epilepsy, neurodegeneration, tauopathy, neuronal hypoexcitability and/or seizures comprises delivering or administering a gene therapy of this disclosure to a cell of a subject in need thereof. In some cases, the subject in need thereof is at risk for or has any one of Dravet syndrome, Alzheimer's disease, epilepsy, and/or seizures. In some cases, the subject is a child or a minor. In some cases, a gene therapy comprising an expression cassette disclosed herein is used to treat an infant, a child, or a minor diagnosed with or is at risk of developing Dravet syndrome. In some cases, a gene therapy comprising an expression cassette disclosed herein is used to treat a subject comprising a mutation or a genetic defect in any one or more of SCN1A, SNC2A, SNC8A, SCN1B, SCN2B, KV3.1, KV3.3, and STXBP1.

In some aspects, the present disclosure provides a method of treating any one of Dravet syndrome, Alzheimer's disease, epilepsy, neurodegeneration, tauopathy, neuronal hypoexcitability and/or seizures, comprising administering a gene therapy into a cell of a subject, wherein the gene therapy comprises an expression cassette disclosed herein.

In some cases, such expression cassette comprises any one or more of SEQ ID NOs: 1-32, or a functional fragment or a combination thereof, or sequences having at least 80%, at least 85%, at least 90%, at least 95%, or at least 99% sequence identity thereto, operably linked to a transgene, wherein the transgene is any one of SCN1A, SNC2A, SNC8A, SCN1B, SCN2B, KV3.1, KV3.3, STXBP1, and a functional fragment thereof. In some cases, the transgene is a subunit of a sodium ion channel or a potassium ion channel. In some cases, the transgene is a syntaxin binding protein. In some cases, the transgene is a transcriptional modulator, e.g., a transcriptional activator or a transcriptional repressor. In some cases, the transgene is a transcriptional modulator that modulates the expression of an endogenous gene (e.g., SCN1A, SNC2A, SNC8A, SCN1B, SCN2B, KV3.1, KV3.3, or STXBP1). In some cases, a transgene is a gene editing protein, such as a zinc finger nuclease or a transcription activator-like effector nuclease. In some cases, the transgene is a Cas protein, such as Cas9.

In other aspects, the present disclosure provides a method for modifying any gene therapy designed for treating Dravet syndrome, Alzheimer's disease, epilepsy, neurodegeneration, tauopathy, neuronal hypoexcitability and/or seizures by adding one or more regulatory elements disclosed herein to improve the cell-type selectivity of the gene therapy. In some cases, the gene therapy is an rAAV gene therapy.

In some cases, treatment with an expression cassette disclosed herein reduces seizure duration and/or frequency, e.g., seizures associated with Dravet syndrome, by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

In some cases, treatment with an expression cassette disclosed herein reduces high gamma power activity (e.g., high gamma power activity associated with Alzheimer's disease) by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, 60%, 65%, 70%, 75%, 80%, 85%, 90%, or 95% as compared to an untreated control or as compared to the level before treatment.

In one aspect, the present disclosure provides a nucleic acid cassette of this disclosure comprises one or more regulatory elements operably linked to a transgene that result in selective expression in a target cell type over one or more non-target cell types, e.g., selective expression in PV neurons in the CNS over one or more non-PV CNS cell types. In some cases, each of the regulatory elements comprises (i) a sequence of SEQ ID NOs: 1-32, (ii) a functional fragment or a combination thereof, or (iii) a sequence with at least 80% sequence identity to (i) or (ii). In some cases, the percent sequence identity can be measured using BLAST. In some cases, at least one of the regulatory elements is human derived. In some cases, at least one of the regulatory elements is derived from a non-human mammal. In some cases, the regulatory elements are non-naturally occurring. In some cases, the regulatory elements result in a selectivity of expression in PV cells that is greater than expression of the transgene operably linked to CAG or EF1α or a non-selective regulatory element as measured by a co-localization assay. In some cases, a transgene is any one or more of SCN1A, SNC2A, SNC8A, SCN1B, SCN2B, KV3.1, KV3.3, and STXBP1, or a functional fragment hereof, or sequences having at least 80%, at least 85%, at least 90%, at least 95%, or at least 99% sequence identity thereto. In some cases, a transgene is a DNA binding protein that modulates expression of a gene (e.g., an endogenous gene such as SCN1A, SNC2A, SNC8A, SCN1B, SCN2B, KV3.1, KV3.3, and STXBP1), such as transcriptional modulator, transcriptional activator, or transcriptional repressor. In some cases, a transgene is a gene editing protein, such as a zinc finger nuclease or a transcription activator-like effector nuclease. In some cases, a transgene is a reporter gene or a detectable marker, such as eGFP, tdTomato, or RFP. In some cases, a transgene is a Cas protein, such as Cas9. In some cases, the regulatory elements result in selective expression in PV cells at a level that is at least 0.5 fold, at least 0.6 fold, at least 0.7 fold, at least 0.8 fold, at least 0.9 fold, at least 1.1 fold, at least 1.2 fold, at least 1.3 fold, at least 1.4 fold, at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, at least 20 fold, at least 25 fold, at least 30 fold, at least 40 fold, at least 50 fold, at least 60 fold, at least 70 fold, at least 80 fold, at least 90 fold, at least 100 fold as compared to that of a CAG or EF1α or a non-selective regulatory element, as measured by the co-localization assay. In some cases, a fold difference refers to the fold difference between the percentage of eGFP+, PV+ cells that result from one or more regulatory elements and that of a non-selective regulatory element. In some cases, the co-localization assay is an immunohistochemical assay, as described below in Example 5. In some instances, a co-localization assay is performed using a commercially available anti-PV antibody. In some cases, the transgene encodes an ion channel subunit, a neurotransmitter regulator, or a variant or a functional fragment thereof. In some cases, the ion channel subunit is an alpha subunit or a beta subunit of a sodium ion channel or a subunit of a potassium ion channel. In some cases, the transgene is any one of (i) SCN1A, SNC2A, SNC8A, SCN1B, SCN2B, KV3.1, KV3.3, or a DNA binding protein; (ii) a functional fragment thereof; or (iii) a sequence having at least 80% sequence identity to (i) or (ii). In some cases, the neurotransmitter regulator is (i) STXBP1, (ii) a functional fragment thereof, or (iii) a sequence having at least 80% sequence identity to (i) or (ii). In some cases, the regulatory elements and the operably linked transgene are located on different chromosomes. In some cases, the regulatory elements combined are less than 2.5 kb, less than 1.5 kb, less than 1 kb, or less than 500 bp in size. In some cases, the non-PV cells comprise any one or more of non-PV CNS cell types, including but not limited to excitatory neurons, dopaminergic neurons, astrocytes, microglia, or motor neurons. In some cases, the nucleic acid cassette is a linear construct. In some cases, the nucleic acid cassette is a vector. In some cases, the nucleic acid cassette is a plasmid. In some cases, the vector is a viral vector. In some cases, the viral vector is an adeno-associated virus (AAV) vector. In some cases, the AAV vector is AAV1, AAV8, AAV9, scAAV1, scAAV8, or scAAV9. In some cases, the viral vector is a lentiviral vector. In some cases, the regulatory elements contain less than 600 bp of contiguous sequence from within 10 kb of the transcription start site of GAD2, GAD1, SYN1, NKX2.1, DLX1, DLX5/6, SST, PV, and/or VIP.

In various embodiments disclosed herein, a regulatory element is less than 2050 bp, 2000 bp, 1900 bp, 1800 bp, 1700 bp, 1600 bp, 1500 bp, 1400 bp, 1300 bp, 1200 bp, 1100 bp, 1000 bp, 900 bp, 800 bp, 700 bp, 600 bp, 500 bp, 400 bp, 300 bp, 200 bp, 100 bp, 90 bp, 80 bp, 70 bp, 60 bp, 50 bp, 40 bp, 30 bp, 20 bp, 10 bp, or 5 bp. In various embodiments disclosed herein, an expression cassette comprises a transgene that is larger than a typical transgene size in a conventional viral vector, e.g., AAV. In some aspects, an expression cassette of any embodiment disclosed herein comprises a transgene that is at least 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, 7.5 kb, or 8 kb. In some aspects, any embodiment disclosed herein comprises an expression cassette (e.g., AAV) that comprises a transgene that is more than 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 kb in size. In some aspects, any embodiment disclosed herein can further comprise one or more heterologous nucleic acid sequence or element.

In one aspect, a method of treating a neurological disorder or condition in a subject in need thereof comprises delivering a therapeutically effective amount of a nucleic acid cassette described herein. In another aspect, a method of increasing selective expression of a transgene in PV neurons comprises contacting a cell with a nucleic acid cassette described herein. In some cases, a method of any embodiment disclosed herein is used to treat a neurological condition or disease, e.g., a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., Dravet syndrome, chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, a method of any embodiment disclosed herein can be used to treat Dravet syndrome. A method of any embodiment disclosed herein can be used to treat Alzheimer's disease. In some cases, methods and/or compositions of this disclosure can be used to treat any neurological condition or disease associated with seizure and/or epilepsy, and/or wherein PV neurons are implicated.

In one aspect, a neurological condition described herein is treated with a gene therapy, preferably one that results in preferential expression in one tissue type or cell type over another, e.g., a PV neuron as determined via a co-localization assay. In some cases, the gene therapy is an AAV.

In one aspect, a method of targeting expression of any transgene to PV neurons in the CNS comprises operably linking one or more of PV neuron selective regulatory elements to a transgene. In some cases, the regulatory elements comprise one or more sequences of SEQ ID NOs: 1-32, or sequences with at least 80% sequence identity to SEQ ID NOs: 1-32, or a functional fragment thereof. In some cases, the regulatory elements result in selective expression in PV neurons at a level that is at least 2 fold, at least 5 fold, or at least 7 fold, or at least 10 fold as compared to CAG or EF1α or a non-selective regulatory element operably linked to the transgene, as measured by a co-localization assay. In some cases, the transgene is SCN1A, SNC2A, SNC8A, SCN1B, SCN2B, KV3.1, KV3.3, STXBP1, a DNA binding protein, or a functional fragment thereof. In some cases, the regulatory elements and the transgene are in an AAV. In some cases, the AAV is AAV9.

In one aspect, a method of treating a neurological condition or disorder in a subject in need thereof comprises contacting a cell with a nucleic acid cassette comprising one or more regulatory elements operably linked to a transgene that results in selective expression in PV neurons over one or more non-PV CNS cells. In some cases, the regulatory elements comprise one or more of SEQ ID NOs: 1-32, or a functional fragment or a combination thereof, or sequences having at least 80%, at least 85%, at least 90%, at least 95%, or at least 99% sequence identity thereto. In some cases, the transgene is a voltage-gated ion channel subunit, or a variant or a functional fragment thereof. In some cases, the subunit is a beta subunit of a sodium ion channel. In some cases, the subunit is an alpha subunit of a sodium ion channel. In some cases, the subunit is of a potassium ion channel. In some cases, the transgene is any one of (i) SCN1A, SNC2A, SNC8A, SCN1B, SCN2B, KV3.1, KV3.3, a DNA binding protein or STXBP1; (ii) a functional fragment thereof; or (iii) a sequence having at least 80% sequence identity to (i) or (ii). In some cases, the neurological condition or disorder is associated with a haploinsufficiency or a mutation in any of SCN1A, SCN1B, SCN2B, KV3.1, and KV3.3. In some cases, the neurological condition or disorder is Dravet syndrome. In some cases, the neurological condition or disorder is Alzheimer's disease. In some cases, the neurological condition or disease is a psychiatric disorder (e.g., schizophrenia, obsessive compulsive disorder, addiction, depression, anxiety, psychosis); an autism spectrum disorder (e.g., Fragile X syndrome, Rett syndrome); epilepsy (e.g., chronic traumatic encephalopathy, generalized epilepsy with febrile seizures plus (GEFS+), epileptic encephalopathy, temporal lobe epilepsy, focal epilepsy, tuberous sclerosis); or neurodegeneration (e.g., Alzheimer's disease, Parkinson's disease). In some cases, the neurological condition or disease is any seizure and/or epilepsy related condition or disease wherein PV neurons are implicated. In some cases, the nucleic acid cassette results in selective expression in PV neurons at a level that is at least 2 fold, at least 5 fold, or at least 7 fold, or at least 10 fold as compared to CAG or EF1α or a non-selective regulatory element operably linked to the transgene, as measured by a co-localization assay. In some cases, the nucleic acid cassette is in an AAV. In some cases, the AAV is AAV9.

In one aspect, a method of treating Dravet syndrome comprises contacting a cell with an AAV comprising a transgene that is any one of (i) SCN1A, SCN1B, SCN2B, a DNA binding protein (ii) a functional fragment thereof, or (iii) a sequence having at least 80% sequence identity to (i) or (ii). In some cases, the AAV further comprises one or more PV neuron selective regulatory elements or any of the regulatory elements disclosed herein operably linked to the transgene. In some cases, each of the regulatory elements independently comprises a sequence comprising any one of SEQ ID NOs: 1-32, or any functional fragment or combination thereof, or a sequence comprising at least 80% sequence identity to any one of SEQ ID NOs: 1-32.

In another aspect, a method of treating Alzheimer's disease comprises contacting a cell with an AAV comprising a transgene is any one of (i) SCN1A, SCN2B, KV3.1, KV3.3, and STXBP1, (ii) a functional fragment thereof, and (iii) a sequence having at least 80% sequence identity to (i) or (ii). In some cases, the AAV further comprises one or more PV neuron selective regulatory elements operably linked to the transgene. In some cases, each of the regulatory elements independently comprises a sequence comprising any one of SEQ ID NOs: 1-32, or any functional fragment or combination thereof, or a sequence comprising at least 80% sequence identity to any one of SEQ ID NOs: 1-32.

EXAMPLES

These examples are provided for illustrative purposes only and not to limit the scope of the claims provided herein.

Example 1

Identifying Putative PV-Selective Regulatory Elements

To identify and screen putative regulatory element that are selective for PV cells, one can harvest PV cells from a R26-CAG-LSL-Sun1-sfGFP-Myc knockin mouse using affinity purification, e.g., using anti-GFP or anti-Myc antibodies and protein G-coated magnetic beads. PV cells can be enriched by using anti-PV antibody coated beads or affinity purification matrix. Nuclei are then isolated from the PV cells. Nuclear RNA can be purified from the nuclei and converted to cDNA, and amplified with the Nugen Ovation RNA-seq System V2 (Nugen 7102), followed by sequencing using the Illumina HiSeq 2500. Genomic DNA can be purified from nuclei, fragmented, and used to make methylC-seq libraries, which can be sequenced using the Illumina HiSeq 2000. To generate an ATAC-seq library, nuclei bound to beads are transposed using Tn5 transposase (Illumina FC-121-1030). After 9-12 cycles of PCR amplification, libraries are sequenced using an Illumina HiSeq 2500. To generate a ChIP-seq library, nuclei of PV cells are digested to mononucleosomes using micrococcal nuclease, followed by salt extraction of chromatin, and native ChIP and library construction, which can be sequenced on an Illumina HiSeq 2500. After sequencing these libraries, the sequences are mapped to identify correlations and patterns in hypo-methylation in CG-rich regions, histone modifications, transcriptional factor binding sites, and patterns associated with highly expressed transcriptional factors in PV cells. Overlapping features and correlations from multiple assays and/or libraries described above provide convergent evidence for identifying candidate sequences that are putative PV-selective regulatory elements. Putative PV-selective regulatory elements can be further tested using a co-localization assay as described in Example 5 below. Putative PV-selective regulatory elements can also be tested in B6 PV-Cre mouse (Jackson Laboratory), which is a B6 PV-Cre knock-in mouse that expresses Cre recombinase in parvalbumin-expressing, as described in Example 2 below. After validating PV-selectivity of the regulatory elements, the regulatory elements can be operably linked to a transgene to target expression selectively to PV cells over at least one, two, three, four, five, or more than five non-PV cells.

Example 2

Selectivity for PV Neurons in PV-Cre Mouse

Selectivity for PV neurons can be determined using fluorescent imaging. AAV9 vectors containing eGFP operably linked to (i) a control promoter (EF1α); or (ii) a PV-selective RE identified in Example 1 above; or (iii) a PV-selective RE selected SEQ ID NOs: 1-32; and AAV9 vectors containing a Cre dependent tdTomato are co-injected into a B6 PV-Cre mouse (Jackson Labs). PV-Cre is a knock-in mouse that expresses Cre recombinase in parvalbumin-expressing neurons (such as interneurons in the brain and proprioceptive afferent sensory neurons in the dorsal root ganglia), without disrupting endogenous Pvalb expression.

Mice are infused bilaterally with 1.5 µL of AAV9 vector ($5^{12}$ to $1^{13}$ gc/ml) into the dorsal and ventral hippocampus at a rate of 0.3 µL/min with a 4 min rest period following injection. Mice are anesthetized for the injection. The animals are placed in a stereotaxic frame (Kopf instruments, USA), using the following coordinates for the dorsal hippocampus (AP −2.0 mm, lateral ±1.5, DV −1.4 mm from dura) and the ventral hippocampus (AP −3.1 mm, lateral ±2.8, DV −3.8 mm from dura). A Hamilton syringe (model #80308; 10 µL syringe with corresponding 30 ga blunt tip needle) can be used with the stereotactic micromanipulator, to designate and drill the bur holes. The drill is only used to penetrate the bone. Following drilling, the infusion cannula is lowered into the brain to the depth of the desired location for injection, e.g., injection volume: 1.5 µL; injection rate: 0.3 µL/min. Prior to infusion, the needle is allowed to equilibrate for 1 minute. Once delivery is completed, the needle is left for 4 min and then withdrawn over approximately 1 min. Once all infusions are complete, the skin incision is closed with sutures and administered post-surgery analgesics. The treated mice undergo daily health checks for the remainder of the study and are weighed once weekly to monitor body weight.

For tissue collection, mice are euthanized via isoflurane overdose and perfused with 4% Paraformaldehyde (PFA). A piece of brain tissue containing the hippocampus is extracted and placed in 4% PFA at 4° C. for at least 12 hours. The brain tissue is then dehydrated in 30% sucrose (in phosphate buffered saline) at 4° C. until the tissue sinks to the bottom of the tube. Brain tissue is embedded in Tissue-Tek OCT for sectioning in a cryostat. Sectioned brain tissue is stained for eGFP and tdTomato using standard immunohistochemistry procedures with anti-RFP polyclonal rabbit antibody (Rockland Antibodies and Assay) and anti-eGFP polyclonal chicken antibody (Ayes Labs). Fluorescence microscope imaging is used to visualize the cells. eGFP, or green fluorescence, corresponds to all gene expression. Red fluorescence from tdTomato corresponds to PV+ cells. An overlap of the two fluorescence signals, which can be visualized as yellow or white cells, represents PV+ cells that express the eGFP transgene. AAV9 vectors comprising a PV-selective regulatory element is expected to yield higher number of cells that are eGFP+ and PV+ as compared to the control promoter (EF1α). For example, fluorescence imaging of cells from mice injected with AAV9s comprising any one of PV-selective REs (e.g., SEQ ID NOs: 1-32 or putative REs identified in Example 1) are expected to show higher number of eGFP+ cells that are also PV+. Selectivity for PV cells can be quantified as percentage of all eGFP+ cells that are also PV+.

Example 3

Reduction of Seizures in Dravet Mouse Model

B6(Cg)-Scn1a$^{tm1.1Dsf}$/J mice were obtained from the Dravet syndrome European Federation via the Jackson Laboratories. These mice contain a Dravet syndrome associated mutation in exon 24 of SCN1A (A to V at position 1783). The mice also contain a floxed exon 24 with wildtype sequence. When not manipulated, this strain of mice expresses two copies of the WT allele of SCN1A. However, upon delivery of an AAV expressing Cre recombinase, any cell targeted by the AAV will switch to expressing one copy of the mutant allele. Upon expression of the mutant SCN1A subunit, mice develop spontaneous seizures within 10 days.

B6(Cg)-Scn1a$^{tm1.1Dsf}$/J and control C57Bl6 mice were injected, as in Example 2, with AAVs expressing CRE recombinase under the control of the EF1α promoter and an AAV comprising PV cell selective regulatory element SEQ ID NO: 32 driving expression of either eGFP (SEQ ID NO: 36) or SCN1B (SEQ ID NO: 37). Once all four infusions were complete, telemetry implantation was performed immediately, (F20-EET, Data Sciences International). Electrocorticogram data was monitored continuously for 14 days from 10 days after the surgery. Electrocorticogram data was analyzed and all seizure events were recorded, annotated with date, time start, time stop, duration of the seizures, and severity score. FIG. 1 illustrates the frequency of seizures in 12 hour windows over 14 days following treatment. The mice treated with SCN1B showed a trend towards lower seizure frequency compared to the control animals.

This observation was consistent with the notion that the beta unit of the sodium ion channel, e.g, SCN1B, can contribute to the trafficking and assembly of the sodium ion channel and that increasing the expression of the beta unit selectively in PV neurons can result in increased trafficking and assembly of the Nav1.1 channel, thus leading to a trend towards lower seizure frequency and duration in the mice treated with SCN1B gene therapy.

Example 4

Treating Alzheimer's Disease in a Mouse Model

Female APP/PS1 and WT mice bred at PsychoGenics were used in the study. APP/PS1 mice contain human transgenes for both Amyloid Beta Precursor Protein (APP) bearing the Swedish mutation (670 G-T and 671 A-C) and Presenilin 1 (PSEN1) containing an L166P mutation, both under the control of the Thy1 promoter. These mice develop symptoms of Alzheimer's disease, including amyloid plaques and memory defects. Further description of these mice can be found in Radde et al, 2006 (Radde, Rebecca, et al. "Aβ42-driven cerebral amyloidosis in transgenic mice reveals early and robust pathology." EMBO reports 7.9 (2006): 940-946).

Figure 2:
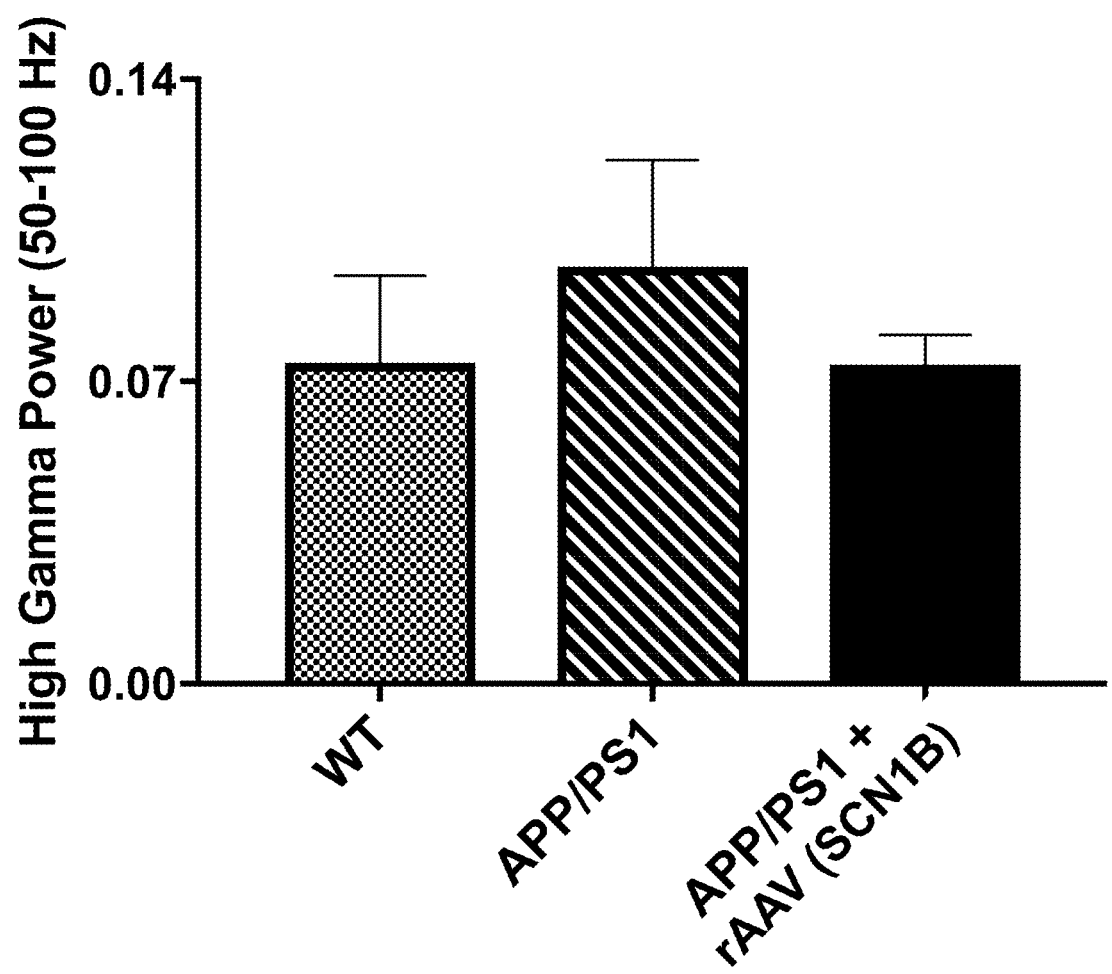
FIG. 2 illustrates high gamma power (50-100 Hz) of different mice: wild-type control (WT), untreated transgenic APP/PS1 mice (APP/PS1), or transgenic APP/PS1 mice treated with rAAV comprising SCN1B operably linked to a regulatory element comprising a sequence of SEQ ID NO: 32 (APP/PS1+SCN1B).

APP/PS1 mice were used as a model to determine the effect of treatment with SCN1B under the control of a RE on symptoms of Alzheimer's disease. APP/PS1 mice and non-transgenic controls were injected with either a control vector expressing eGFP or a treatment vector expressing SCN1B, both under the control of SEQ ID NO: 32; and implanted with an EET transmitter as in Example 3. Brain activity was assessed over 24 hours at 4 weeks after surgery. Electrocorticogram data was automatically analyzed and power levels in the different frequency bands were compared. FIG. 2 illustrates the high gamma power (50-100 Hz) in non-transgenic controls (WT), APP/PS1, and APP/PS1 mice treated with SCN1B. Increased high gamma power activity is associated with seizures in Alzheimer's patients and epilepsy patients. The APP/PS1 mice showed a higher level of high gamma power activity than the control mice. However, the increase was absent in the treated mice indicating effective treatment with the vector.

Example 5

Selectivity for PV Neurons in C57BL/6J (WT) Mouse

The selectivity of various REs disclosed herein were tested for selective gene expression in PV neurons using immunohisotochemical methods. C57BL/6J (WT) mouse line was used for the PV immunohisotochemical assays. Expression cassettes comprising reporter transgene eGFP operably linked to a regulatory element (SEQ ID NO: 1 or SEQ ID NO: 8) or a CAG promoter in an AAV9 construct.

Pup Systemic Infusions:

Postnatal day 1 C57BL/6J mice were infused via facial vein injection with AA9 vector (1 $E^{12}$ to 3 $E^{12}$) using a 300 U insulin syringe with a 31 G needle. For tissue collection, mice were euthanized 21 days post-infusion via overdose of sodium pentobarbital (i.p.) and perfused with heparinized (2.5 IU/ml) saline followed by perfusion with 4% formaldehyde. Brains were removed and subsequently immersion-fixed in 4% formaldehyde for 24-48 hours at 4 degrees Celsius. The brain was then placed into PBS containing 30% sucrose and allowed to sink at 4 degrees Celsius (~2-3 days). Upon sinking the individual brain hemispheres were frozen in Tissue-Tek OCT with the midline facing down. Frozen brains were processed for sagittal sections on a cryostat and placed free-floating into PBS. Sections were stained for eGFP and parvalbumin (PV) using standard immunohistochemistry procedures with chicken anti-GFP (Ayes Lab, GFP-1020) and mouse anti-PV (Sigma, P3088).

Adult Systemic Infusions:

4-week-old, C57BL/6 mice were infused via tail vein injection with 60 µL of AAV9 vector ($4.9^{13}$ to $1^{14}$ gc/ml) expressing eGFP. For tissue collection mice were euthanized 21 days post-infusion via isoflurane overdose and whole brains were extracted, washed with PBS and placed into separate 5 ml tubes containing ice cold 4% formaldehyde. Tissue was fixed at 4 degrees Celsius overnight. The following day, the brain was placed into PBS containing 30% sucrose and allowed to sink at 4 degrees Celsius. Upon sinking the individual brain hemispheres were frozen in Tissue-Tek OCT with the midline facing down. Frozen brains were processed for sagittal sections on a cryostat and placed free-floating into PBS. Sections were stained for EGFP and parvalbumin (PV) using standard immunohistochemistry procedures with chicken anti-GFP (Ayes Lab, GFP-1020) and mouse anti-PV (Sigma, P3088).

Immunohistochemistry Protocol:

Immunohistochemistry was used to analyze the co-localization of eGFP signal and PV signal using the anti-PV antibody, wherein overlay of the signals exhibited as white or light gray spots in the top panel images (merge), wherein representative overlay was indicated by arrowheads. Overlay of the eGFP and PV fluorescence is indicative of expression in PV cells. Such experiments can be used to determine the selective expression of expression in PV cells. To perform the immunohistochemical experiments, tissues obtained from each mouse were blocked with a Blocking Buffer Solution (comprising 3% BSA, 3% NGS, 0.3% Triton X-100, 0.2% Tween-20 in 1×PBS) for 1 hour at room temperature. The tissues were then incubated with primary antibodies in blocking buffer overnight at 4 C, washed three times with 1 mL 1×PBS, each with 5 minutes interval. Then the tissues were incubated with secondary antibodies in blocking buffer for 1 hour at room temperature, followed by washing three times, each time with 1 mL 1×PBS and with 5 minutes interval. The tissues were incubated DAPI (1:1000) in PBS buffer for 5 minute and wash twice with 1 mL 1×PBS. Tissues were mounted onto slides, imaged, and analyzed using a fluorescence microscope. Images were taken using a Vectra 3 imaging system (Perkin Elmer) and quantified for co-labeling of eGFP and PV staining using inform-Tissue finder, advanced image analysis software or hand scored. At least 80 GFP positive cells were counted in each panel before determining the percentage of co-localization.

Figure 3B:
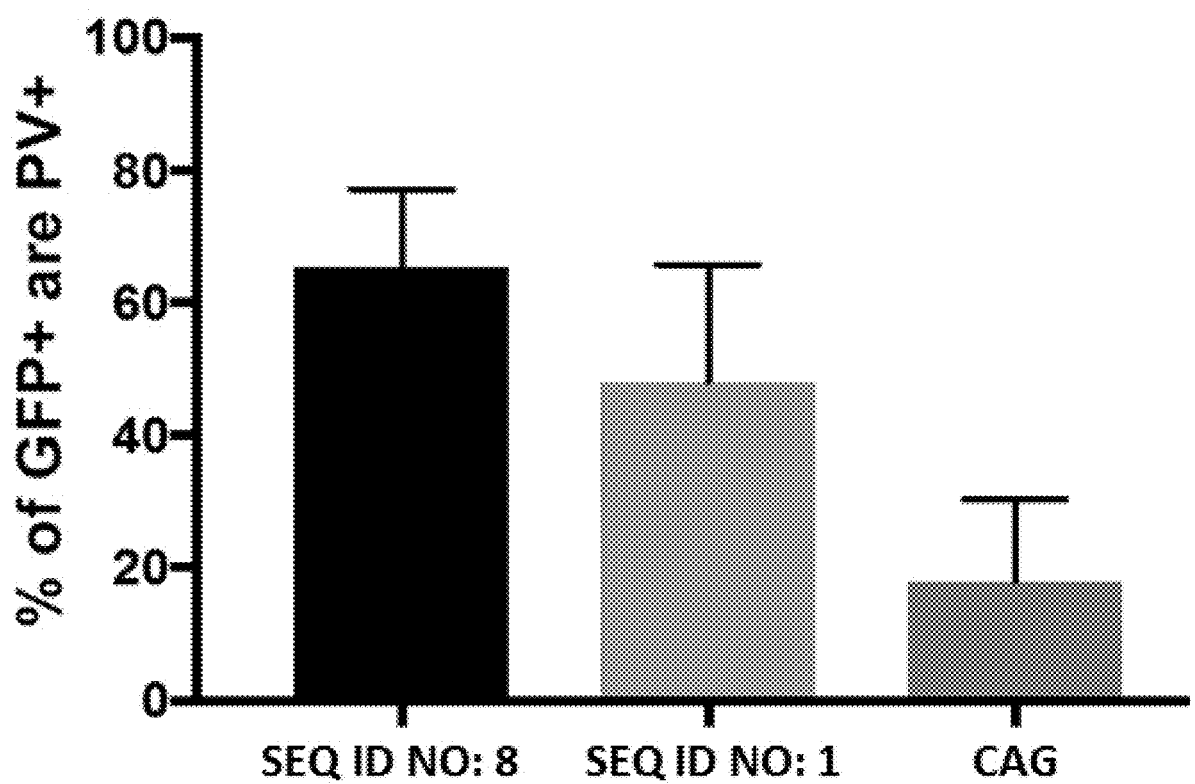
FIG. 3B illustrates the quantification of immunofluorescence co-localization studies illustrated in FIG. 3A, wherein selective expression in PV cells is expressed as the percentage of eGFP+ cells that were also PV+ in comparison to the CAG control, as measured by the immunofluorescence co-localization assay.
Figure 4A:
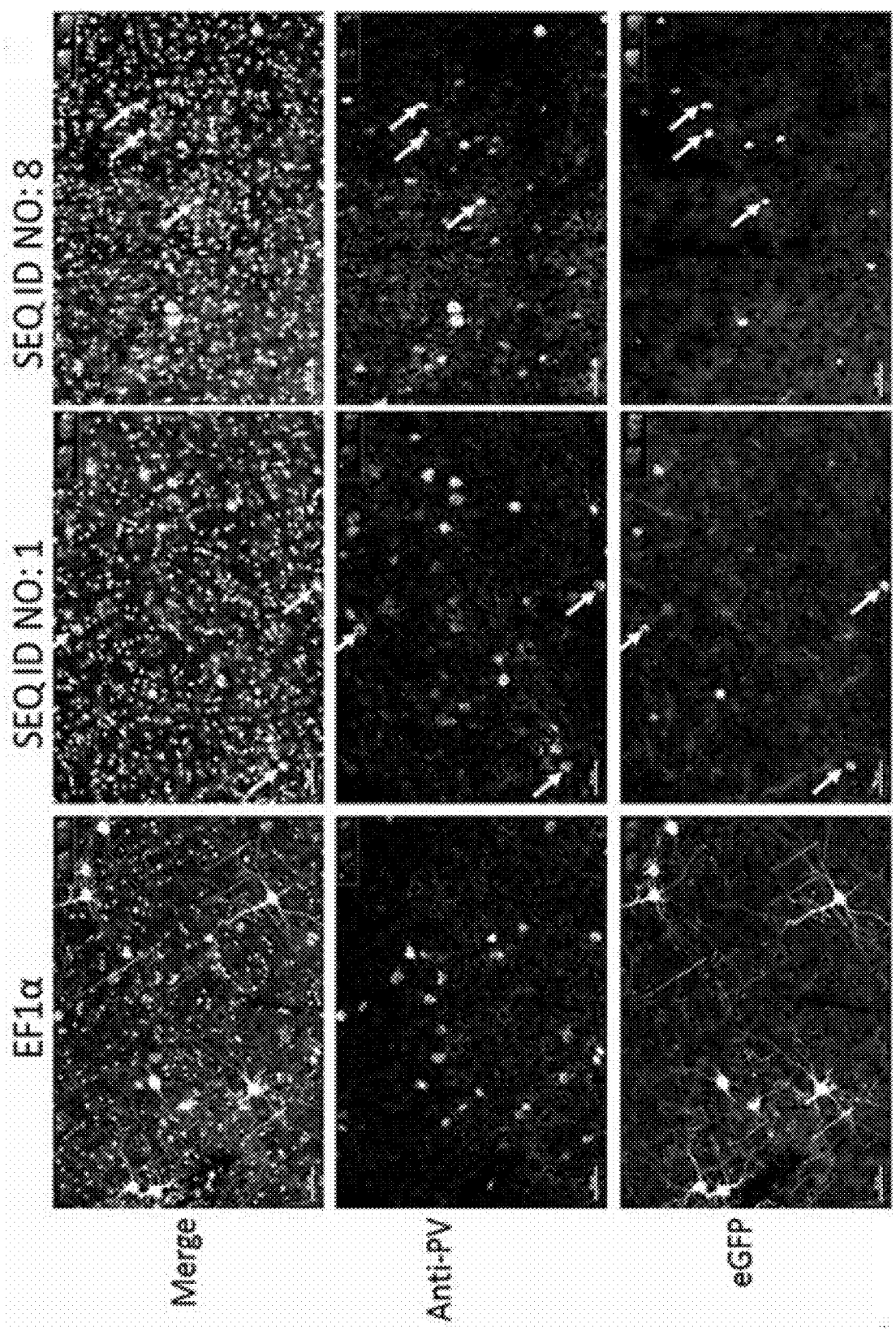
FIG. 4A illustrates immunofluorescence co-localization assay of CNS cells from adult mice following systemic injections of AAV9 comprising eGFP transgene operably linked to a regulatory element comprising a sequence of SEQ ID NO: 1 or SEQ ID NO: 8. AAV9 comprising eGFP transgene operably linked to EF1a was used as a control. Lower row images illustrate eGFP+ cells. Middle row images illustrate PV+ cells, which were stained with an anti-PV antibody. Top row images (merge) illustrate an overlay of PV+ eGFP+ fluorescence (with representative eGFP+ and PV+ cells, or the white or light grey cells, indicated by arrowheads) and DAPI+.
Figure 4B:
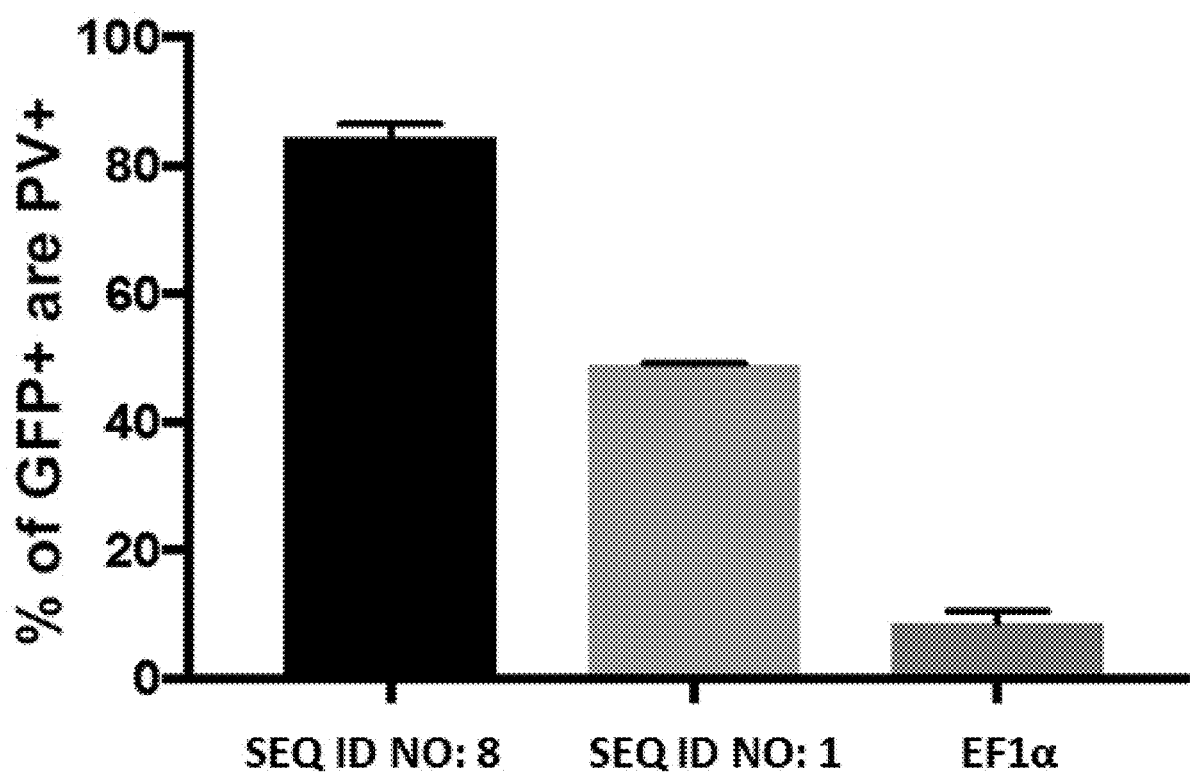
FIG. 4B illustrates the quantification of immunofluorescence co-localization studies illustrated in FIG. 4A, wherein selective expression in PV cells is expressed as the percentage of eGFP+ cells that were also PV+ in comparison to the EF1a control, as measured by the immunofluorescence co-localization assay.
Figure 5A:
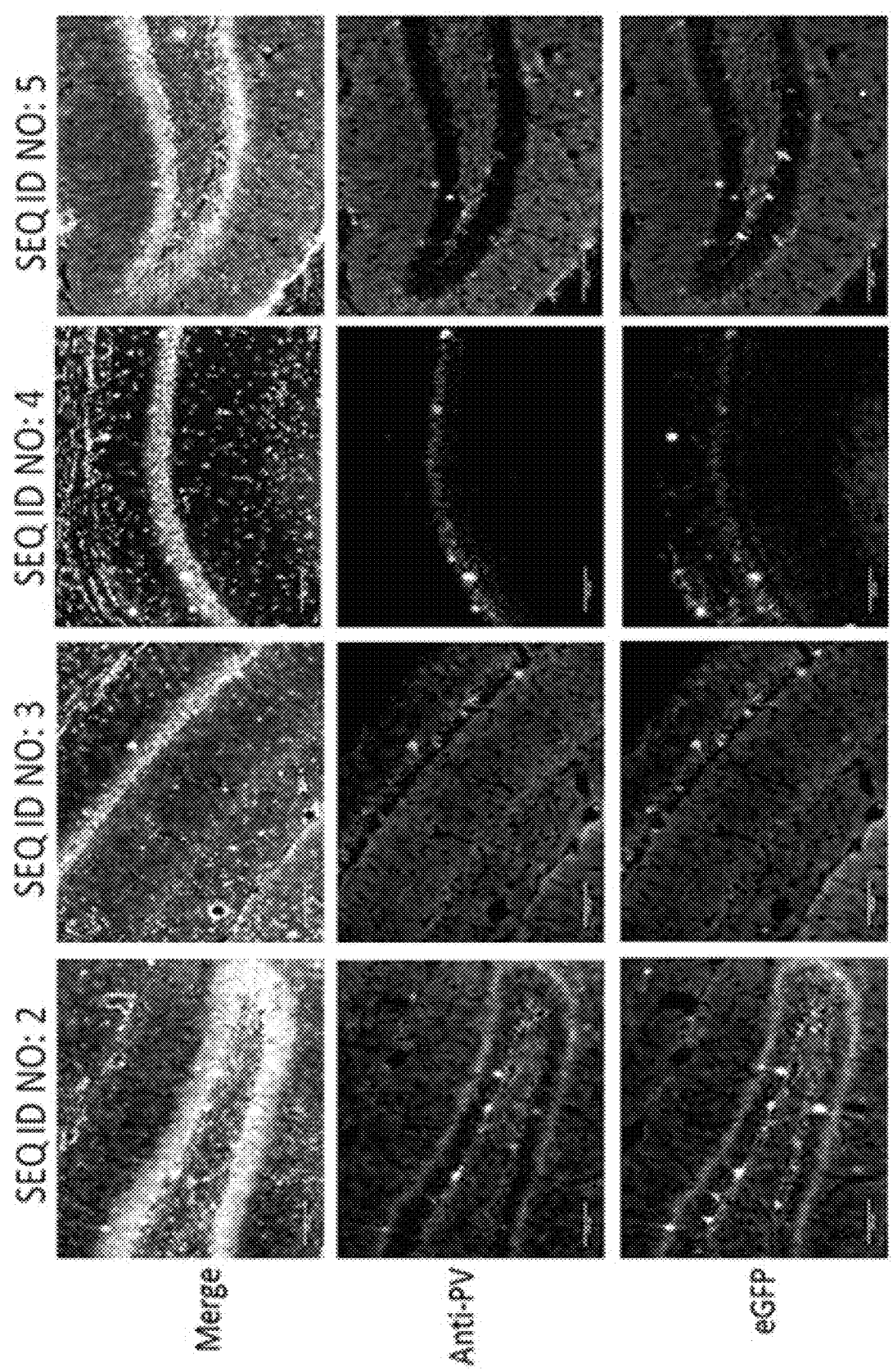
FIGS. 5A-5F illustrate immunofluorescence co-localization assay of CNS cells from adult mice following direct CNS injections of AAVDJ comprising eGFP transgene operably linked to a regulatory element comprising a sequence of SEQ ID NOs: 2-22. Lower row images illustrate eGFP+ cells. Middle row images illustrate PV cells that were stained with an anti-PV antibody. Top row images (merge) illustrate an overlay of PV+, eGFP+ fluorescence (with representative eGFP+ and PV+ cells, or the white or light grey cells, indicated by arrowheads) and DAPI+.
Figure 5B:
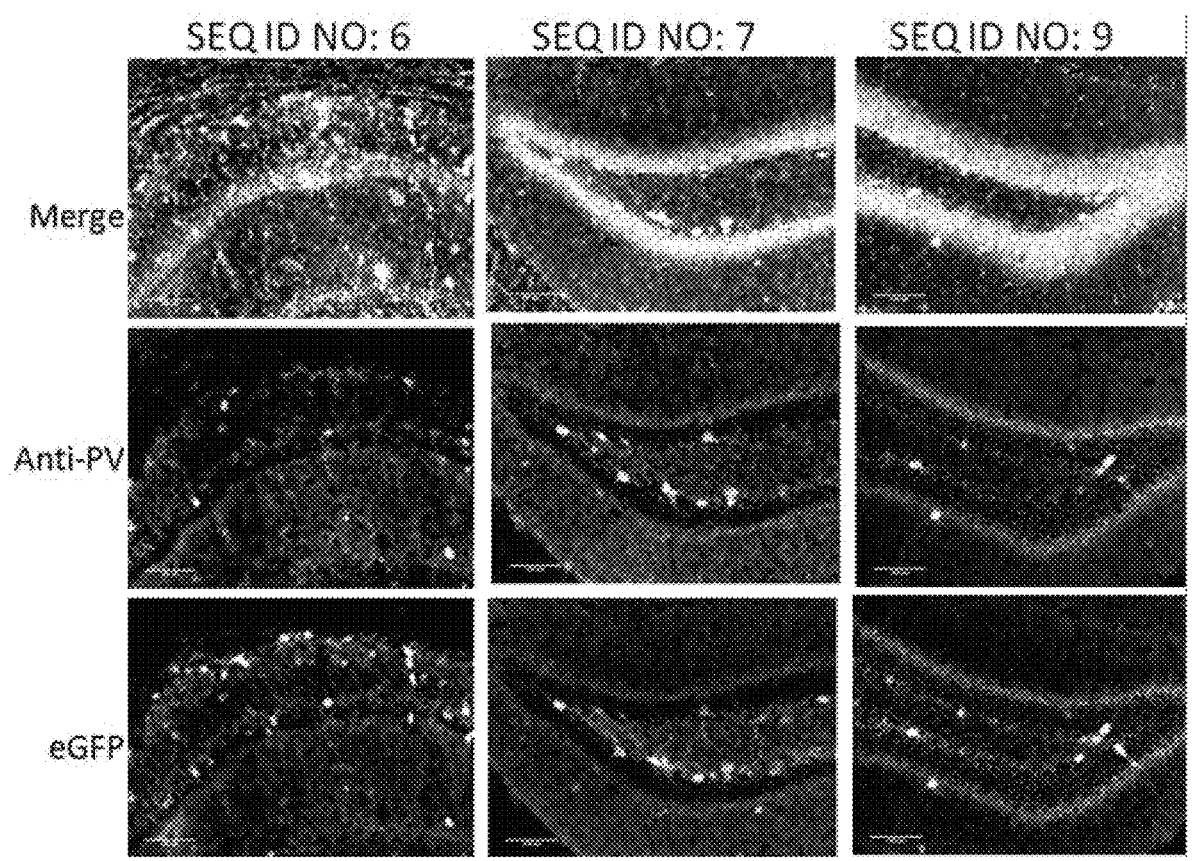
Figure 5C:
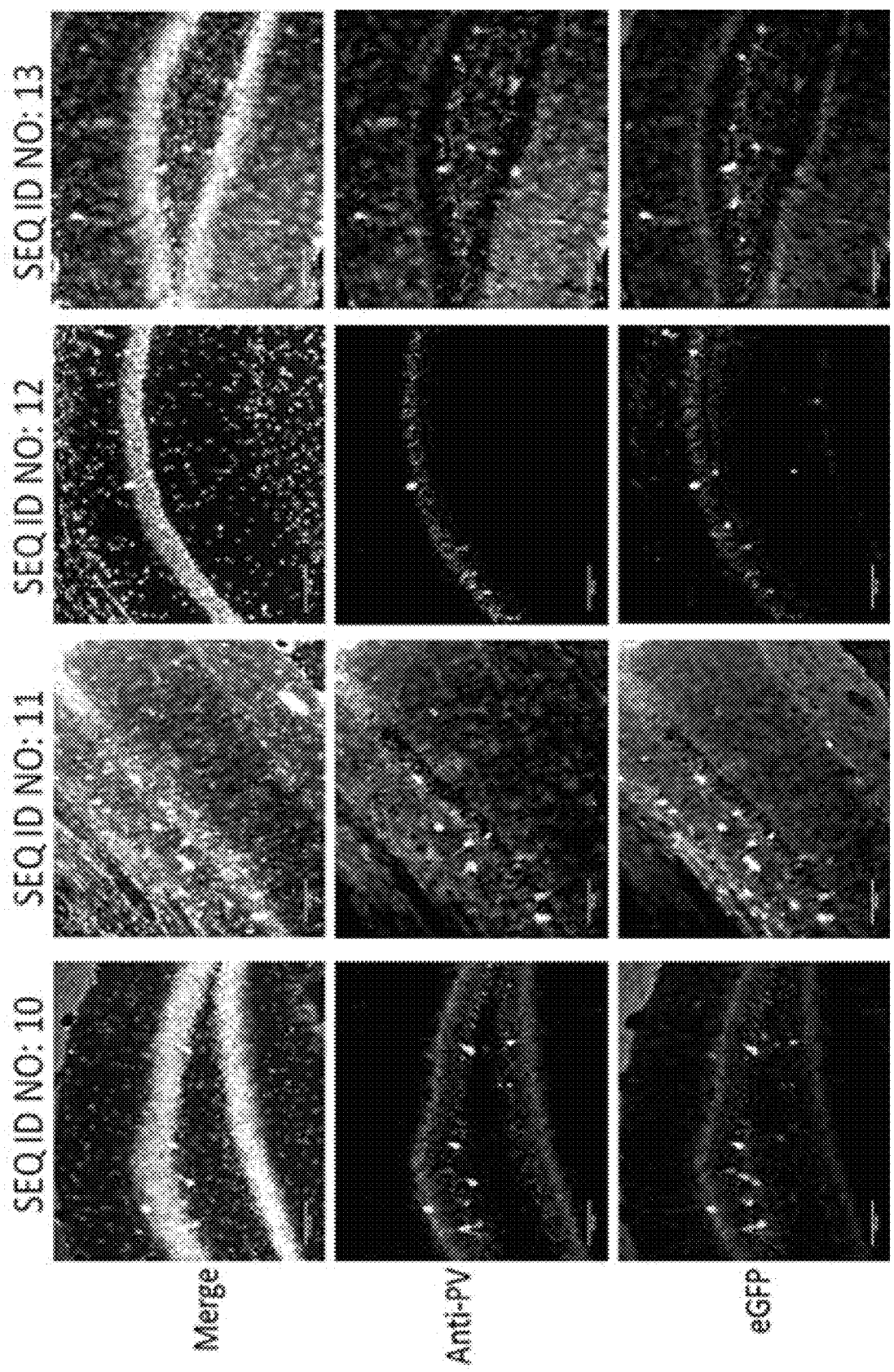
Figure 5D:
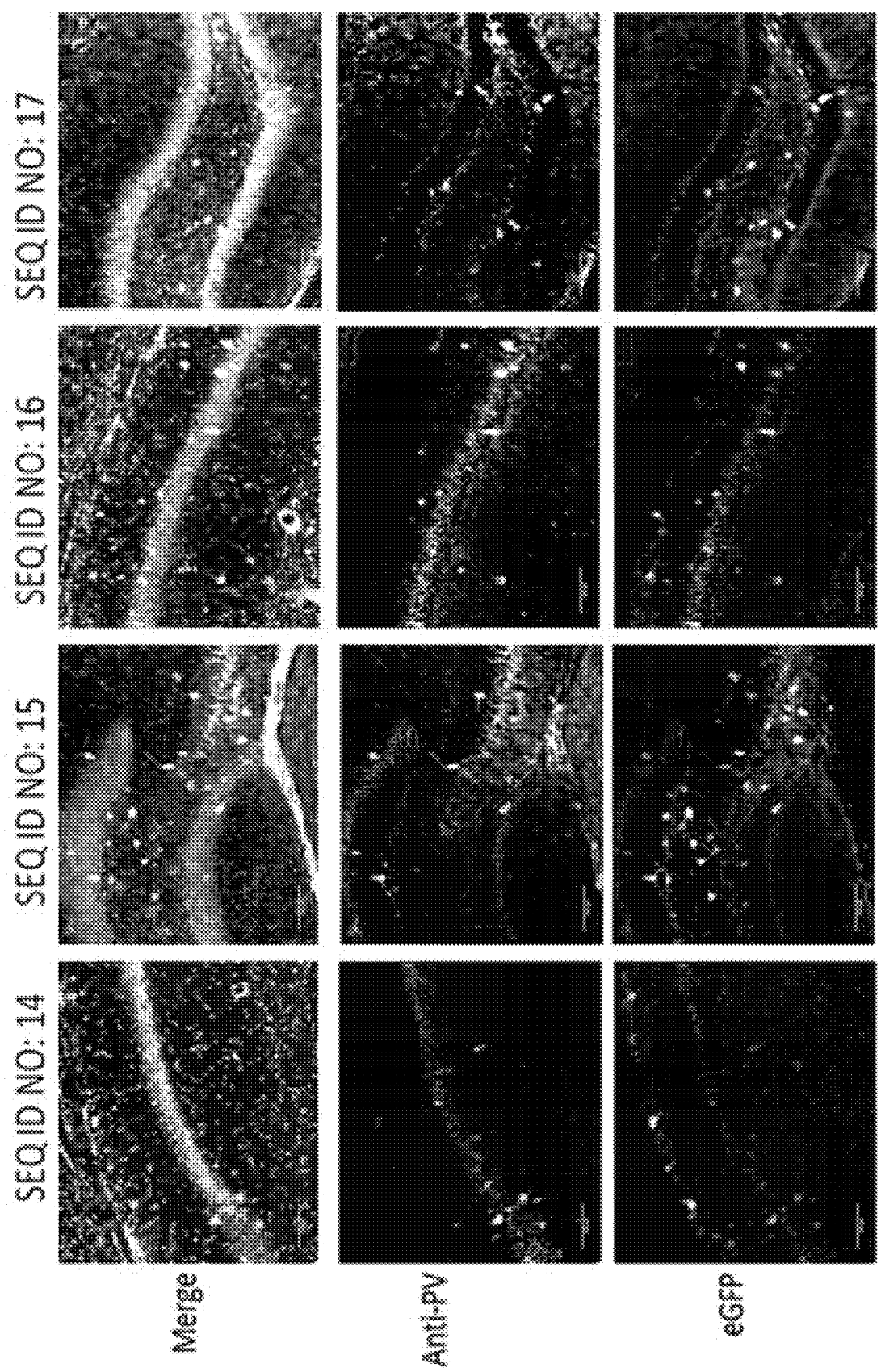
Figure 5E:
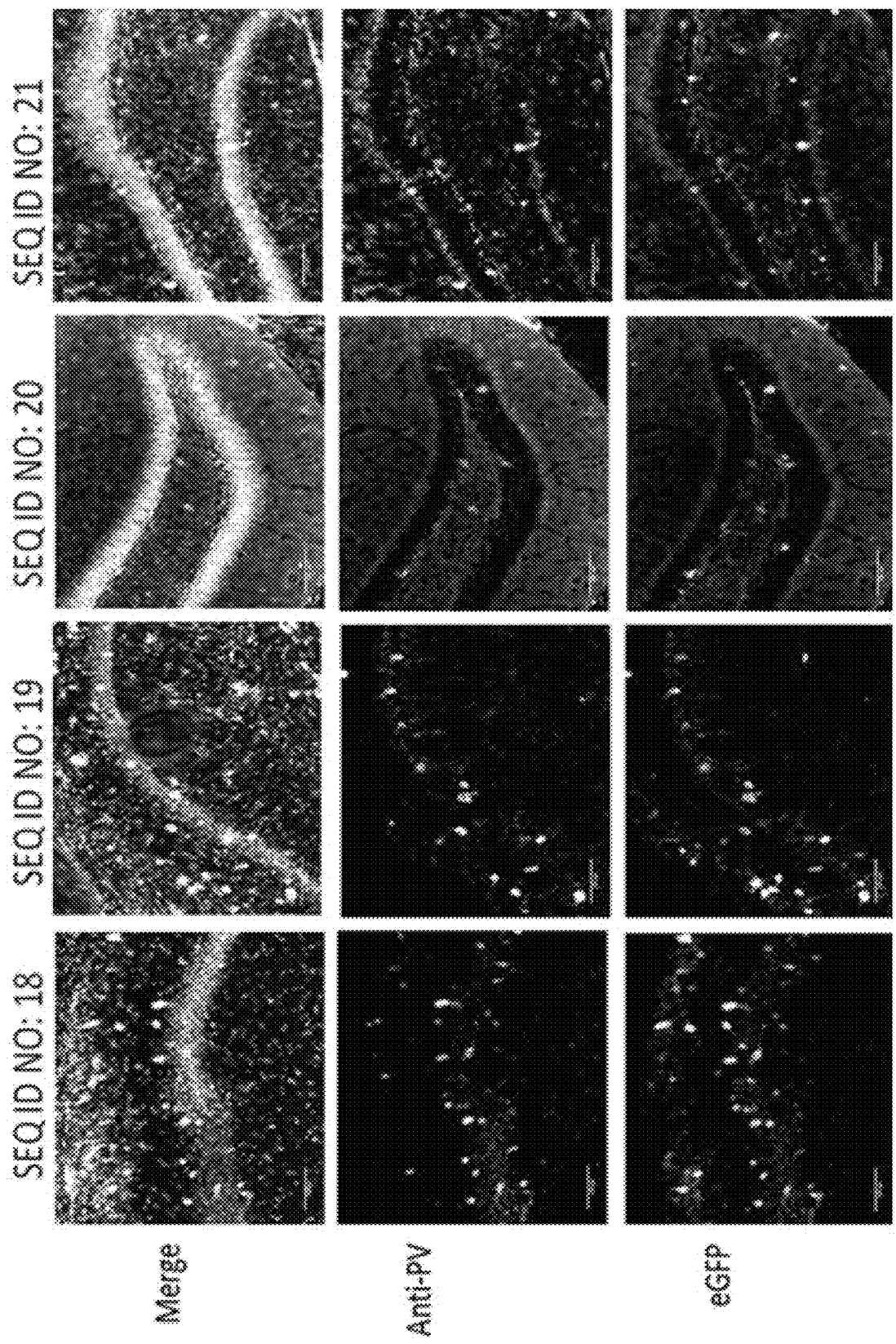
Figure 5F:
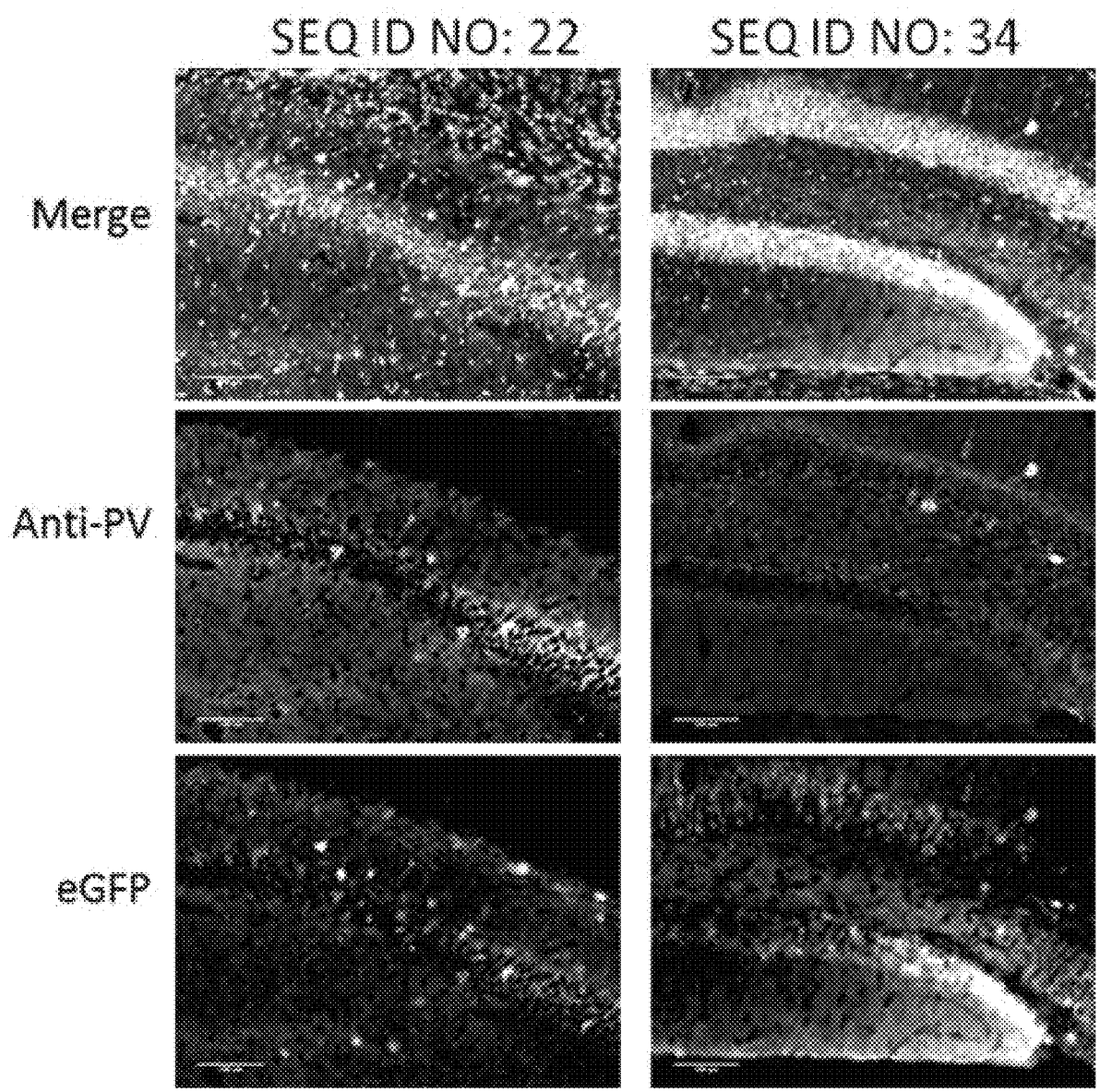

FIGS. 3A-3C illustrates the results of the immunohistochemistry experiments performed in pups after systemic AAV9 injections. FIGS. 4A-4C illustrates results of similar immunohistochemistry experiments performed in adult mice following AAV9 injections.

FIG. 3A illustrates the overlay of the immunohistochemistry experiments performed in pups after systemic AAV9 injections. FIG. 3B illustrates the quantification of the co-localization of the immunohistochemistry experiments, wherein selectivity for PV cells was measured as percentage of GFP+ cells that were also PV+, as compared to eGFP expression under the control of the CAG promoter.

FIG. 4A illustrates the overlay of the immunohistochemistry experiments performed in adult mice after systemic AAV9 injections. FIG. 4B illustrates the quantification of the co-localization of the immunohistochemistry experiments, wherein selectivity for PV cells was measured as percentage of GFP+ cells that were also PV+, as compared to eGFP expression under the control of the EF1α.

It is estimated that GABAergic neurons constitute about 20% of CNS, while PV cells constitute about 40% of GABAergic neurons, which means that PV cells make up approximately 8% of all neurons in the CNS. See Pelkey, K A et al., 2017; and Lee, S. et al., 2010. Thus, one would predict that about 8% of the cells labeled by a non-selective regulatory element (e.g., CAG, EF1α, or a constitutive promoter) would be PV positive, or within this range. Therefore, expression in PV cells above 8% is indicative of increased selectivity in PV cells. Notably, AAV9 injections comprising regulatory element SEQ ID NO: 8 resulted in about 60% of cells as PV positive, which was 7.5 times higher than what was expected by the distribution of PV cells.

Figure 6:
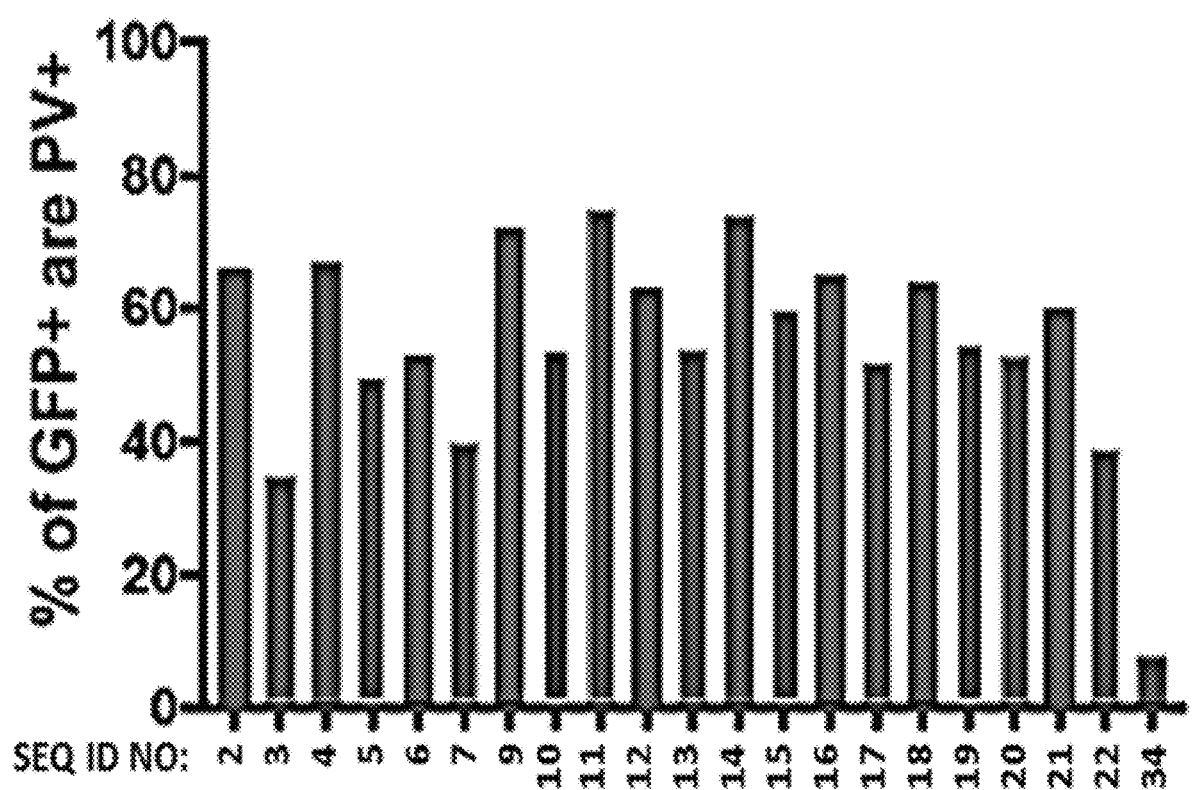
FIG. 6 illustrates the quantification of immunofluorescence co-localization studies illustrated in FIGS. 5A-5F, wherein selective expression in PV cells is expressed as the percentage of eGFP+ cells that were also PV+ in comparison to SEQ ID NO: 34, as measured by the immunofluorescence co-localization assay.

Similar immunohistochemistry experiments as described above were performed to determine the selective expression of additional regulatory elements, SEQ ID NOs: 2-7 and 9-22 as compared to a non-selective regulatory element having a sequence of SEQ ID NO: 34, except AAVDJ viral vector was used to deliver eGFP operably linked to a regulatory element into C57BL/6J (WT) mice. Such AAVDJ virus was injected directly into the CNS in the hippocampus of adult mice. At least 80 GFP positive cells were counted in each experiment before calculating the percentage of co-localization, or selectivity, as percentage of GFP positive cells that were also PV positive. FIGS. 5A-5F illustrate the fluorescence imaging used for determining co-localization, or selectivity, measured as percentage of eGFP positive cells that were also PV positive and in comparison to the signal of non-selective regulatory element SEQ ID NO: 34. Cells that were positive for a marker appear as white/gray cells in the images. Merge images illustrate the overlap between the corresponding eGFP and anti-PV images. Cells that were positive for both eGFP and PV appear as white/light gray cells in the merge image. FIG. 6 illustrates the quantification of the co-localization analysis, measured as percentage of eGFP+ cells that were also PV+.

Example 6

Treatment of Dravet Syndrome in Different Mouse Lines

Treatment of Dravet syndrome and/or symptoms thereof using the expression cassettes described herein can be tested in various mouse lines, such as B6(Cg)-Scn1a$^{tm1.1Dsf}$/J as described above, Scn1a$^{tm1Kea}$, and Scn1a-R1470X mouse lines. These mouse lines are established mouse models for Dravet syndrome. Scn1a$^{tm1Kea}$ and Scn1a-R1470X mouse lines do not require CRE recombinase.

The Scn1a$^{tm1Kea}$ mouse (available from the Jackson Laboratory; described in Hawkins et al., Scientific Reports, vol. 7: 15327 (2017)) comprises a deletion of the first coding exon of SCN1A. Mice homozygous for the SCN1A knock-out allele are characterized by tremors, ataxia, seizures, and die by postnatal day 16. Heterozygous mice on the C57BL/6 background develop spontaneous seizures and die within weeks. Such mouse strain can be used to study safety and efficacy of treatment of epilepsy and Dravet syndrome. See Miller et al., Genes Brain Behav. 2014 February; 13(2):163-72 for additional information.

The Scn1a-R1470X mouse is a knock-in mouse carrying a premature stop codon, R1407X, in exon 21 of the SCN1A gene. The same mutation has been identified as a pathogenic mutation in three unrelated SMEI patients. Scn1a$^{RX/RX}$ pups are characterized by recurrent spontaneous seizures at 12 postnatal days, including tonic-clonic and clonic seizures at 12-16 postnatal days, and rhythmic jerking movements and involuntary muscle contraction. See Ogiwara et al., Journal of Neuroscience, May 30, 2007, 27 (22) 5903-5914 for additional information.

To test the compositions described herein, such as AAV gene therapy and treatment using such gene therapy, Dravet mice of each of the mouse strains described above and control mice (e.g., a wild-type mouse or an untreated Dravet mouse for the strain) are injected (e.g., administered by intraperitoneal injection) with AAVs expressing either eGFP or another reporter gene, or an expression cassette comprising one or more PV-selective REs SEQ ID NOs: 1-32 as described herein operably linked to a transgene disclosed herein, such as SCN1A, SCN1B, or SCN2B, or any of SEQ ID NOs: 37-39, or a variant or functional fragment thereof. Following AAV injections, mouse survival is monitored over time. All mice are monitored daily for general health (e.g. weight, hydration, grooming, and mobility) and deaths were recorded. Telemetry implantation can be performed immediately after AAV injections (F20-EET, Data Sciences International). Electrocorticogram data can be recorded and monitored continuously for at least 14 days from 10 days after the surgery. All seizure events can be recorded for at least 14 days following AAV treatment, annotated with date, time start, time stop, duration, and severity score. A reduction in the frequency and/or duration of seizures following treatment with an AAV as described above as compared to the eGFP control or an untreated control is indicative of the efficacy of the gene therapy in reducing the symptoms and/or severity of Dravet syndrome.

After treatment of the mice with AAV, the expression levels of the transgene (e.g., SCN1A; SCN1B; SCN2B; a DNA binding protein, such as a transcriptional activator, that modulates an endogenous SCN1A, SCN1B, or SCN2B; any of SEQ ID NOs: 37-39; or any variant or functional fragment thereof) can be monitored over time using various PCR and/or sequencing methods to show AAV treatment can result in an increase in gene expression in PV cells. Northern blot analysis and in situ hybridization can also be used to analyze transgene expression in vivo. The level of the protein expressed from the protein can also be monitored after treatment to show an increase in transgene expression correlates with an increase in the corresponding protein in vivo. Protein levels can be assayed using various methods, including, but not limited to, Western blot analysis, immunohistochemistry, immunofluorescence histochemistry, and/or ELISA assays. Formation of functional voltage-gated sodium ion channels can also be assayed using current-clamp analysis.

Hyperthermia-induced seizures can be evaluated to compare the wild-type mice and/or untreated Dravet mice with Dravet mice treated with AAV gene therapy comprising an expression cassette described herein (e.g., an expression cassette comprising one or more REs of this disclosure operably linked to a transgene of this disclosure, such as SCN1A, SNC2A, SNC8A, SCN1B, SCN2B, a functional fragment thereof, or a DNA binding protein that modulates an endogenous SCN1A, SNC2A, SNC8A, SCN1B, or SCN2B). In such experiments, the core body temperature is monitored with a RET-3 rectal temperature probe (Physitemp Instruments, Inc, New Jersey, USA) and controlled by a heat lamp connected to a rodent temperature regulator (TCAT-2DF, Physitemp) reconfigured with a Part-low 1160+ controller (West Control Solutions, Brighton, UK). Body temperature is raised 0.5° C. every two minutes until the onset of the first clonic convulsion. As compared to the untreated Dravet mice, Dravet mice treated with an AAV gene therapy are expected to have a higher threshold temperature before the onset of first clonic convulsion and/or have a higher proportion of mice that remain seizure free at the maximum temperature tested.

Different doses of AAV comprising an expression cassette can also be administered to mice to determine the safety and efficacy profile of each gene therapy treatment. These preclinical studies can also inform the optimal dose(s) of the gene therapy to use for treating Dravet syndrome.

Example 7

Treatment of Alzheimer's Disease in Mouse

Female APP/PS1 and wild-type (WT) mice, which are bred at PsychoGenics and are established mouse model of Alzheimer's disease, can be used to study the safety and efficacy of the compositions described herein in treating Alzheimer's disease, comprising one or more PV-selective REs. APP/PS1 mice is describe above in Example 4.

APP/PS1 mice and non-transgenic controls are injected with either a control AAV vector expressing eGFP or a treatment AAV vector comprising one or more PV-selective REs disclosed herein, e.g., SEQ ID NOs: 1-32, operably linked to a transgene that is deficient or impaired in Alzheimer's disease, such as SCN1A, SNC2A, SNC8A, SCN1B, SCN2B, STXBP1, a DNA binding protein that modulates an endogenous gene (e.g., SCN1A, SNC2A, SNC8A, SCN1B, SCN2B, KV3.1, KV3.3, or STXBP1), or any one of SEQ ID NOs: 37-43, or a functional fragment thereof.

Following AAV injections, mouse survival is monitored over time. All mice are monitored daily for general health (e.g. weight, hydration, grooming, and mobility) and deaths were recorded. After injections of the AAVs, mice are also implanted with an EET transmitter as described in Example 3 above. Brain activity can be recorded and monitored over 24 hours for at least 4 weeks after surgery. Electrocorticogram data can be automatically analyzed, and power levels in the different frequency bands (50-100 Hz) can be compared across different groups: WT mice, untreated APP/PS1 mice, and AAV-treated APP/PS1 mice, each treated with an AAV gene therapy as described above. Increased high gamma power activity is associated with seizures in Alzheimer's patients and epilepsy patients. Thus, the untreated APP/PS1 mice are expected to show a higher level of high gamma power activity than the control mice, while this increase is expected to be absent or reduced in the treated mice, indicating an effective treatment with an AAV gene therapy.

After treatment of the mice with AAVs, the expression levels of the transgene can be monitored over time using various PCR and/or sequencing methods to show AAV treatment can result in an increase in endogenous expression of the transgene. Northern blot analysis and in situ hybridization can also be used to analyze gene expression in vivo. The level of the protein expressed from the transgene can also be monitored after treatment to show an increase in gene expression correlates with an increase in protein levels. Protein level can be assayed using various methods, including, but not limited to, Western blot analysis, immunohistochemistry, and/or ELBA assays. Formation of functional voltage-gated sodium or potassium ion channels can also be assayed using current-clamp analysis.

Different doses of AAV comprising an expression cassette can also be administered to mice to determine the safety and efficacy profile of each gene therapy treatment. These preclinical studies can also inform the optimal dose(s) of the gene therapy to use for treating Alzheimer's disease.

What is claimed is:

1. A nucleic acid cassette comprising a regulatory element comprising SEQ ID NO: 30 operably linked to a transgene.

2. The nucleic acid cassette of claim 1, wherein the transgene comprises a nucleic acid sequence encoding a DNA binding protein.

3. The nucleic acid cassette of claim 2, wherein the DNA binding protein is a transcriptional modulator of an endogenous gene.

4. The nucleic acid cassette of claim 2, wherein the DNA binding protein comprises a zinc finger.

5. The nucleic acid cassette of claim 2, wherein the DNA binding protein is a nuclease-deactivated zinc finger protein.

6. The nucleic acid cassette of claim 2, wherein the DNA binding protein is linked to a transcriptional activator domain.

7. The nucleic acid cassette of claim 2, wherein the DNA binding protein is linked to a transcriptional repressor domain.

8. The nucleic acid cassette of claim 2, wherein the DNA binding protein is a transcriptional activator that modulates an endogenous SCN1A gene.

9. The nucleic acid cassette of claim 1, wherein the nucleic acid cassette is an adeno-associated virus (AAV) vector.

10. The nucleic acid cassette of claim 9, wherein the AAV vector is AAV9 or scAAV9.

11. The nucleic acid cassette of claim 8, wherein the nucleic acid cassette is an adeno-associated virus (AAV) vector.

12. The nucleic acid cassette of claim 11, wherein the AAV vector is AAV9.

13. The nucleic acid cassette of claim 11, wherein the AAV vector is scAAV9.

* * * * *

SEQUENCE LISTING

```
<160> NUMBER OF SEQ ID NOS: 43

<210> SEQ ID NO 1
<211> LENGTH: 681
<212> TYPE: DNA
<213> ORGANISM: Homo sapiens

<400> SEQUENCE: 1
ggaggaagcc atcaactaaa ctacaatgac tgtaagatac aaaattggga atggtaacat      60
attttgaagt tctgttgaca taaagaatca tgatattaat gcccatggaa atgaaagggc     120
gatcaacact atggtttgaa aaggggggaaa ttgtagagca cagatgtgtt cgtgtggcag     180
tgtgctgtct ctagcaatac tcagagaaga gagagaacaa tgaaattctg attggcccca     240
gtgtgagccc agatgaggtt cagctgccaa cttctctttt cacatcttat gaaagtcatt     300
taagcacaac taacttttt ttttttttttt tttttttgag acagagtctt gctctgttgc     360
ccaggacaga gtgcagtagt gactcaatct cggctcactg cagcctccac ctcctaggct     420
caaacggtcc tcctgcatca gcctcccaag tagctggaat tacaggagtg gcccaccatg     480
cccagctaat ttttgtattt ttaatagata cgggggtttc accatatcac caggctggt     540 ctcgaactcc tggcctcaag tgatccacct gcctcggcct cccaaagtgc tgggattata     600
ggcgtcagcc actatgccca acccgaccaa ccttttttaa aataaatatt taaaaaattg     660
gtatttcaca tatatactag t                                              681

<210> SEQ ID NO 2
<211> LENGTH: 502
<212> TYPE: DNA
<213> ORGANISM: Mus musculus

<400> SEQUENCE: 2
agtttggaca agaactatag ttctagcttt ctctgggtct ccaccttgca gagaatgcag      60
ctttcattat ctcatgagcc aaactctcat catctctttc catatatctg tcggtgctct     120
tccatgagta ctctaacaca cacagaagga gcacttacac aggctgttgt ttttctctta     180
ttatcatagc tgttgttcag acatgtgcat tctgttcttg ttgcttcaat gctaaaggag     240
tctcaggata tgagaactgt accagccgag gcatcaggaa acatgggtgg aaattcccac     300
agtactattt gttcactgtg tgaccttggg ccagtcacat cccttttcctg aggcttcgat     360 tccccaagct ataaaagaag catctcttaa ccttttttta ggtcatgagt caggcccagc     420
acactctcag ggagactcat gagagtacag atcatttccc atagaaaaac catagtttta     480
tatccagagg cttttctgta ag                                             502

<210> SEQ ID NO 3
<211> LENGTH: 823
```

<212> TYPE: DNA
<213> ORGANISM: Mus musculus

<400> SEQUENCE: 3

```
ggttccagtt cagaggcaga gcatttgggg ttcccagtca ggagctttcc tctctccgct      60
ccttagtttc ctctctttaa aaaaaaatgg gtgatagtat agaaaggaag ctctgggctc     120
ggggaccagg gccctgggat ccccgctccc agccactcgc tcctgaccct tccagggaca    180
agctcccccc caccccgtcc tttccaggct gccactagaa gagatgggga cgcgtggtca    240
gccgcttctg tcgcccccca gggaacggtc tcacgctgga gggggcagtg ccctcggaac    300
aggacagtca gcccaagcca gccaagcgcg cgcggacgtc cttcaccgca gagcaattgc    360
aggtaccccg ggcaagcccc gaagcgtgtg ggcggggctt cggagtgggc gtggttgttc    420
gggacttgtg actccgcccc ttgtgcgggg accgcgtga ggccgctcca aggatgaagc    480
tgcctggggc gtggcctcgg accctgagcc tctgattggg cggaggtctc agggcccttc    540
tgcgccccac aggttatgca ggcgcagttc gcgcaggaca caacccgga cgcgcagacg    600
ctgcagaagc tggcggacat gacgggcctc agtcgcaggg tcatccaggt ggggctccgg    660
ggtctcggcc ttcaggtcta gggtgaacct tagggaagcg ctgaagctcg tagtggtacg    720
gatggtcgcg cgtgcacgtg gccgcccctc tccagtgtgg cctaaggacc ccagtcggca    780
cgggttgacc ctttttccttg attactgaga gtgcagaggc tgt                    823
```

<210> SEQ ID NO 4
<211> LENGTH: 633
<212> TYPE: DNA
<213> ORGANISM: Mus musculus

<400> SEQUENCE: 4

```
tggtgggaag acatgtccag ggaagaaatg gcctccagag gcctgaggtg gggaaatgct     60
ggaggtggag agaggaacaa ctgactgaaa atgagcttcc actgtggctt agtagcctat    120
accaagtcta gagtataggg taggagaaga ttaggaaagc gatgggtctg agaatgatgt    180
ggcctgttga cttttgtaaa cccaaagcac cttggactaa accctatgaa cagtgtggtg    240
ccaccaaaga ctataatgag ctcagggaac agaattctgt gtgcatggtg atttttttt    300
ttttttttctg ctaactgcag tctgggtgat gcattgacaa accaatcctg gaaagtaaga    360
ggcaagggca gctgggacgg tgagaggagc ctgatggaa ccaggccaag cagggcagca    420
gaggcgatga agaggatgtg gtgcatccag agactcactt cattagctgg aggcactgct    480
ggatagggtc tgaaggttct ggtatctgag ttggcgggct gggtgagtgg tggctctgct    540
tcctgaacag tgtgtgcaag aggaaacagg gttaagggct aggacagtca caggtgagtc    600
agcctcacaa gagcaacctt ccctagtgc aga                                    633
```

<210> SEQ ID NO 5
<211> LENGTH: 670
<212> TYPE: DNA
<213> ORGANISM: Mus musculus

<400> SEQUENCE: 5

```
ggaggtctcc ttttgccccg gttccaacaa gagaatgcaa ggctgtatct caatttcctt      60
gagcctctct gtattataga agaaaagtag ggaagccata cgccccttct gagcttcagt    120
gtctctctgt ctctgcaaat gaggctgggg aggctggggg cgggcgtgaa agaggcccgc    180
gccaagccga ccccaccctc tgcccctcc ccaggtcaac aacctcatct ggcacgtgcg    240
```

| | |
|---|---|
| gtgcctcgag tgctccgtgt gtcgcacatc gctgaggcag cagaatagct gctacatcaa | 300 |
| gaacaaggag atctactgca agatggacta cttcaggtag gcagcggcca tcccgccagc | 360 |
| aagcgctgga gcatgaacgc cttgcacacg cgtgcctagg ccacttgtgt ggcctgtgct | 420 |
| ctccaattcc tgagccctgc tgttcagagt gcacaacgcg gctcagcgca ctggcccggc | 480 |
| cctcctactc agcacgtctt acacagaagg gagcgccagt ctcagcctga gttctggcgg | 540 |
| gggatctgcc tcgggttcct ccgatctgac aggcgctggc cacgggtctg gttccatctc | 600 |
| tggtcttttc tggccccgag caccagtgtg ttctgttgag ctctgatgtc cgaggctctg | 660 |
| gcccggatca | 670 |

<210> SEQ ID NO 6
<211> LENGTH: 1043
<212> TYPE: DNA
<213> ORGANISM: Mus musculus

<400> SEQUENCE: 6

| | |
|---|---|
| ctctggctac ctcttatctt gggcattcac gacaatttct aattgcaggt agtttgtgtg | 60 |
| tgtgcgcgtg ttttttttcc ccctcagagg cttggattgc aaaggaacta agcgattact | 120 |
| tcaagagcca cgggttaagt gcaggggagag ggggagagag agggaaaaaa acccaatcca | 180 |
| aattcaaatt gcttcattag agagacaccg cttttgtggg aagggctttt aaatgcccac | 240 |
| tacaaagtta ggactcattg ttcagcgccg gtttatataa caggcgaggg gaggcgctgg | 300 |
| gctctgacag ctccgagcca gttcagcagc cgccgtcgcc tgcattccct cccccctcccc | 360 |
| caggtgatgg cccagccagg gtccggctgc aaagcgacca cccgctgtct cgaagggacc | 420 |
| gctccgcctg ccatggtgag tccttttcggt cctgctttcg gccccgagtc cccccaacag | 480 |
| cacaggccag ggcttctggc tcagccttcc ggctaccaac ctctacccct cgctggaaaa | 540 |
| actgccgata ggagccgcct ctcgttgagc cttggttttt ctggcctgga atgtgagctt | 600 |
| tggctgcttc ctgcacccag gatgcgctgt gttaaaagtt gggggccgtc ccttcttctc | 660 |
| caataggtcc tttcattctt gtactccagc ctagggcgcg acatccctgg cacatttcgg | 720 |
| tgtcagtcgg tgcgcgagga aaccagattc aactctgagt actcggctaa gcgcttcgct | 780 |
| gttcctctct cccatttcag gctcagtcag acgcagaggc cttggcaggc gctctggaca | 840 |
| aggacgaagg tagagcctcc ccatgtacgc ccagcacacc gtctgtctgc tcgccgccct | 900 |
| ctgctgcctc ttccgtgccg tctgccggca agaatatctg ctccagttgc ggtctggaga | 960 |
| tcctggaccg gtatctgctc aaggtgagtc agggtaggtg tgcctgcttg cccacgggtg | 1020 |
| tggtttgcag ccccaagagc tgt | 1043 |

<210> SEQ ID NO 7
<211> LENGTH: 507
<212> TYPE: DNA
<213> ORGANISM: Mus musculus

<400> SEQUENCE: 7

| | |
|---|---|
| caagactttt aaaagtttag ataaataaac aaacatttga cggctttcca tcacatctag | 60 |
| actataatcc aaagatctat atggtcccaa acgacttaca cttaactacc gtctcccata | 120 |
| tggcttcttc ccccatcagt cattgtcctc agccatagtg gcctccctgt tcctttgggt | 180 |
| acaagggaac aactccctga gaggttccat tagctgctgt tgcctgagat gctcttgagc | 240 |
| ccacaccatc tgctcatttc tctcctcacg tgtcagtgat taagaggctg tccttggcct | 300 |
| cccgtcaaaa ttacatccct gccgctttcc acttcttgcc ttcttatttt ctaaatagaa | 360 |

```
ctaactcacc actacccaac attctatata attggatatc tgtcctctgt ttaaatataa    420
tgttgacttc aagaaagaac gttgtcactg ccctgtcacc agacttttaa acagtgccta    480
tcgtgtggca catgctcagt gaaattg                                       507
```

<210> SEQ ID NO 8
<211> LENGTH: 502
<212> TYPE: DNA
<213> ORGANISM: Mus musculus

<400> SEQUENCE: 8

```
tcaacagggg gacacttggg aaagaaggat ggggacagag ccgagaggac tgttacacat     60
tagagaaaca tcagtgactg tgccagcttt ggggtagact gcacaaaagc cctgaggcag    120
cacaggcagg atccagtctg ctggtcccag gaagctaacc gtctcagaca gagcacaaag    180
caccgagaca tgtgccacaa ggcttgtgta gagaggtcag aggacagcgt acaggtccca    240
gagatcaaac tcaacctcac caggcttggc agcaagcctt taccaaccca cccccacccc    300
acccaccctg cacgcgcccc tctcccctcc ccatggtctc ccatggctat ctcacttggc    360
cctaaaatgt ttaaggatga cactggctgc tgagtggaaa tgagacagca gaagtcaaca    420
gtagatttta ggaaagccag agaaaaaggc ttgtgctgtt tttagaaagc caagggacaa    480
gctaagatag ggcccaagta at                                            502
```

<210> SEQ ID NO 9
<211> LENGTH: 788
<212> TYPE: DNA
<213> ORGANISM: Mus musculus

<400> SEQUENCE: 9

```
aaatagaact gtgagatagg gggagagggg gcaggaagga caagagaccc ctgtctcatt     60
gtgatcccca cctgtctgct ctgtgggagg gtacccatga gggccagccc acagcccta    120 ggtggacatt gtctggtcct gtctcactgt ccctcccagc agcccagag gccaggagac    180 agggtctca gtcctcactg agagatgtgt aaactgaggc ccagtgaatg ttgagggcca    240
gggcatgccc ttggtgggat gtgacctggg tctccttcgc acgggcttcc tccccgaagc    300
cgagctgagc atttggagtt tgaaatgttt ccgtacttag caatctgctc ctctattccc    360
gggcggactt ccgatagctc cggccttatg ctgcactaga taagatggag cagggagagg    420
acacggcact acttatgtaa ccggcctctt gaaaaatgga gcagcggtca gggcggaaca    480
agacgtcctc tctctacgca tccctctcct ttccctgcta aggctgcagc tggagtcaga    540
ggcagggctg ttccaatctg tctttgatca gtaacgcagc cagcctccag cctccgtcag    600
cctcctcatg gctgagaccc ggcctcagtt tcccccactt acatcccgag gatcagagcc    660
tgtgaggatg aaatgggata aggtagctgg aaccgtctgg cagagagcga gtcctcagga    720
ctgttgatgc ctgtggctgc ctggcttgac cccaagtgac cccgcctcct catcctgcag    780
caggagaa                                                            788
```

<210> SEQ ID NO 10
<211> LENGTH: 502
<212> TYPE: DNA
<213> ORGANISM: Mus musculus

<400> SEQUENCE: 10

```
tctatagaat gtgtccccag ccttgttttc cacacttgat acgcaaggaa tgcataccac     60
```

```
agagagggat gagggtagca tccagcctgc ttcctgtgtg tcgggcgct acagccacat      120 ctccccagtc catctcagac cgtcacagag cttcgccgaa tgtatagctt tgttctctgt      180
gcagacaggg agacagagcc ttgggaagca taggtgcttg cttctttgcc cactgagtct      240
tagctggact tgcacaccac atgcctcaca gccgggcgca cttgcatttg tcacccaggc      300
ccagtgatga tggctctgct tgctttgtgc tttgtgccaa ctacagctcc agcacctgtg      360
ccctgggttt tcactccttt agttgaacac gtagttactg ggttgtagg gatggagcct      420 ttctgcttcc ttctggcaaa gtccttagcg gcctgctgcg ggggtggggg gtgttcaggg      480
gagtggtgat gaagtatgac ag                                                502
```

```
<210> SEQ ID NO 11
<211> LENGTH: 533
<212> TYPE: DNA
<213> ORGANISM: Mus musculus

<400> SEQUENCE: 11
tctccagttg gagaaacaga tgctgtaact ggggccacag tataaagaga gcccagacat       60
tgaactgtca acacagaagc ctggcacact ggaactggca gtccagctgg gaacaagggg      120
tagaggctga ggccactaag tcaactgagg caggagacat aggagctaaa gcagctgaag      180
ggtgcaggac agctggggggg tctgaagtgg gcctcatgcc cagagctatg aagtcagggg      240
ctgtagccta ggagccttgg aagccagctg gcaagctgtg gcccaaagac gctgactcac      300
caggaggggg cagctggagc caggcactcc taaggtttcc aggaagggca gccttccagg      360
gctcagctag gggagacagt gttgacagca agttgtcagg caacttgagc tactgggcag      420
ctgggaagct gtcccttggt ccccagtatc atcatcaccc cagacgctgc ccacctgcct      480
caggtcccac acagtgatcc tcccatcttt aacacaacac atgaccagag aga              533
```

```
<210> SEQ ID NO 12
<211> LENGTH: 524
<212> TYPE: DNA
<213> ORGANISM: Mus musculus

<400> SEQUENCE: 12
gtcaccctcc ccccaaacaa ccccttcttc tctggttcga gaaattacag gcatgaaaga       60
tataaatcgg gatgcttgac ttgggaatat aaatcactaa agcttggggg caggggtggg      120
cgacctttgt gaccgtcctt gtgcgtgcca gtaaatcctg tggtccaggg gagaagaaaa      180
ggctgtgtgg cttctgctca caaagctgca gaaaccattc tttaagccca aaagcacttc      240
cagagagagc agagcatccc caggctgctg gctcagcaag ttcactgtgc tcaatctcag      300
gaagtgagga taagagcagt gcctggagag tgcctggtgc tgagctgagg gtttctgaac      360
acattaaagc ggggagcatg gaccgggcct caggaggggt gttgaacatc cctaggcaga      420
ggagtctagc ttcctgggaa aagatatcag gttaagcaca cacatgtcct ctggaataag      480
ataatctttc tgatcacaca ctatacacac acaaaagcct gctc                        524
```

```
<210> SEQ ID NO 13
<211> LENGTH: 509
<212> TYPE: DNA
<213> ORGANISM: Mus musculus

<400> SEQUENCE: 13
gccctctagg ccacctgacc aggtcccctc agtccccccc ttcccacact cccacactca       60
gcccccctcc cccccccccg acccctgcag gattatcctg tctgtgttcc tgactcagcc      120
```

```
tgggagccac ctgggcagca ggggccaagg gtgtcctaga agggacctgg agtccacgct    180
gggccaagcc tgcccttct  ccctctgtct tccgtccctg cttgcggttc tgctgaatgt    240
ggttatttct ctggctcctt ttacagagaa tgctgctgct aattttatgt ggagctctga    300
ggcagtgtaa ttggaagcca gacaccctgt cagcagtggg ctcccgtcct gagctgccat    360
gcttcctgct ctcctcccgt cccggctcct catttcatgc agccacctgt cccagggaga    420
gaggagtcac ccaggcccct cagtccgccc cttaaataag aaagcctccg ttgctcggca    480
cacataccaa gcagccgctg gtgcaatct                                       509
```

<210> SEQ ID NO 14
<211> LENGTH: 398
<212> TYPE: DNA
<213> ORGANISM: Mus musculus

<400> SEQUENCE: 14

```
gtgttcttcc cttccccttt ggaccccga gacaagccaa taaaatactc ggcagggtgg     60
cttctctcct ttttttgcca gtaataaaca gactcagagc aagttaaggg tctggtccaa    120
ggtcatggct gggatcagtg acagagccca aagagaacc tgagacttct tgctgagcca    180
agctggagag acagaaagg aatgcgtcta ctccatgcat gaccctctgc cagctttgct    240
ccttcctaag ggaccatgaa cgatatgtgc acaccgctca tacgtatgtg cacacctgca    300
agaggaggca tcccatgtac acctatgaga cgcacagaga aacatatatg tagccatagg    360
ctagaaattc tttctctttc taggtctgcc cctctgca                            398
```

<210> SEQ ID NO 15
<211> LENGTH: 810
<212> TYPE: DNA
<213> ORGANISM: Mus musculus

<400> SEQUENCE: 15

```
ggaccactca gtgtacacgg aatgtagaat tgagtctgcc attggtcttc cctcaaagtc     60
ttggaggctt gggactgata ttgggagcat ctgggcagag aaggccacaa agacagggtg    120 gttttttctac actgggacat actcgtgagc atgcacagag gcgtgtcccc aacttccctg    180 tcaccctgt cctctgccgg ctagagggga tgcgggggtg gacatatgct gctattgggc     240
agatatcaca tgttaagagg tggggggggg ctcaagaggc ggagggctag gagcatccca    300
tggggagagg ttctggtttt cttgctgcct ctagctgcta taaatacgtt agcacttgag    360
caactggaaa gctctgagta atttaggatg cacaaagctg taatttaact ccagcatctc    420
agtgtgcgag agcattaaag atgtaattaa gatgtttaca caaagagatt ggagtctgtg    480
acacttgggg tgcaaaaccc caggaaggga cacaatgggt gaggtgagga tctgtgggag    540
gcctggggac agtcacttgg atcccagcta tgagatggca ggccacccag ctgtttctcc    600
ttggaaatgt tttggcctgg gggttggggg tgggcatca cactttgata tggagatggg     660
gcaacaaagc ctgcaatatc tggggtgga gaggtcaagt ggatggagtc ttttgagatc     720
atgtcaggaa gagggctcga tcccccaaaa tcatggtgac atatggtgtc tcggggttca    780
caggagctat gtctaaaata caaaagtaaa                                      810
```

<210> SEQ ID NO 16
<211> LENGTH: 202
<212> TYPE: DNA
<213> ORGANISM: Mus musculus

<400> SEQUENCE: 16

```
tctgcagaag cctgccattc caccatttaa acctgtgact ccaggcctta agcctgttga      60
aggtcgagtc ccagaagggt catatgtgca actgcctagg gagagttccc actcgcaggg     120
ccaagaggag tcccccggtc tgaggtgtgg gggcggggac gtgcactggg cgctgggacc     180
acggctgggg ctcaggactc gc                                              202
```

<210> SEQ ID NO 17
<211> LENGTH: 937
<212> TYPE: DNA
<213> ORGANISM: Mus musculus

<400> SEQUENCE: 17

```
tgcctcagtt tcttcgccta gaaagccggg tctaagggta catgccctga ttctttctg       60
gggtgtctcg aattttaaac aacacatact gttctgggct gatgacaaga ggaagtactg     120
gtcggtggct gatggacatc caccatggtg gcaactggag ggaggggaa cggacgttga      180
aaccctgccc tcctggaatc tgtcgcatgc acgcacgttg acaatgcttg gcactgggga    240
caggctggga tggatggagc ggagcgtgag gaggagtggg catgcaggcc cgagtgtctg     300
ttttgctgat tgctcctttt gctttcaagg agattaaact attttttagtc catgcctact    360
gctggtgaga cgctggagga agcctttcca tcgttgagat tttctggaag ctgccaagtg    420
tggtcttcag ctcaattctg ggagcctccc agagtgggag ggaggaacat ttccatctgg    480
gggcttcggg gacaggctaa gatcttccct ggggtccttg ctgcgctggc ctcctcaaac    540
cacgctgcct cggcctgcat aaagcagtaa tctgatgtgc ccgatgtttg taacgctgtg    600
tttaaaaaaa gtaatttatt ttctaattat tccttgtctt gcataaccat gcattgccaa    660
agtgtcgcta tttaaaatat ttatctctcc acgccgcagg agcagctctg gagcgtggag    720
ggggaagaaa taaaagtccg cgtgccagtc gcaggcatat tactttgact cgtcctggtg    780
gctttgacgt ctccctgtaa atacatttat ttttcattag gacgtttctg agcttgtggc    840
ccccggagag cggagtgatt acgctgttca tctgcaagcg atgcaataga ggggtactcg    900
cagaatgact tccgcccaga gcatcctgcg cctgtct                             937
```

<210> SEQ ID NO 18
<211> LENGTH: 922
<212> TYPE: DNA
<213> ORGANISM: Mus musculus

<400> SEQUENCE: 18

```
taaaatacct tattttttc cagtctctaa actgctaatc tcccaggcta agggattctg       60
ggacaaaggc aaggcctgga agtggaaatc tgtaaaatta gcttcagcgg tattagtgtt    120
tgcagttgaa gattgaaaaa ctgctttccc agggcctgat tggaggctcc actctcctcc    180
aggaagaggc aaggactctg ggctggcact gaggacaaat cctgggaggc tgctatgggg    240
cctgggagcc aggctgcctt gtgctagagg cctagagagt gtctgtgtcc caagtcccaa    300
gctaccccca gcagctaaca gcttttccag ttctcaggca cagcaggtgc caagatcacg    360
ctctggagtc cagctgggcc ccttcctctt cttttttttt tttttttttt aagacctcct    420
ggacactgtt cctctccccc ccccgtgac ccccccctc agttctcaaa cacgtgaggg      480
ttggggagg gttccacagc cagagagagg ggccagctct ggtgcctgtg ggtacgcccg     540
cccgtatggc ccatcaggcc tcttgtgtgc ttgattgcct ctgattggct gcagctgaat    600
tcagcaaaag ctattatttg cccttgatga gccaatcaga tggcctcatt ggccattcag    660
```

```
agcaggcacc ggaacctgag ggtggggtgg ggggtggggg atggagatgg gactcagtga      720
gggggtggga agctctaaaa cagatgcagg acctgagcct gtctgtgtcc accacgacct      780
tcacacaggt cacacccct tccctgact tgtcacccca accagggct tgttgcccaa         840 ccccacctca caattccctc actctgtaac acctttccat atacctctgc atgtctaaac      900
ccaagacttg ctctatgaaa tc                                               922
```

<210> SEQ ID NO 19
<211> LENGTH: 639
<212> TYPE: DNA
<213> ORGANISM: Mus musculus

<400> SEQUENCE: 19

```
agaccctgct tagcacagct cttagcgggt cctttagggg gtctcccagc gggcccagtg       60
ggaatgagat aaggaaggac acagctgtcc attctcccgt gcctgctaag gaggaaatgg      120
ggccgcctta cataattggg gcaatttgtt ccactcttgt cctcctggta tcatggctat      180 cacccctcc ttgctcaggg agtccttgat tgagcgagaa gctcaggcct ccctctctcc       240
ctcctgctgg gggttgctga acagagggtg taggagccat aggctctgtc actgctgaga      300
tctgccagat gtctaggcca ggagaaaatg gaaagggcta agtcacagca tatgtggcca      360
ctcaggccta tagccccaaa tctgcctggt aacccattat gtccccagag aatttgcatg      420
ggcggacacc ctcatgccgg gtctcagtaa gggaagggt gggaggcaaa aatatccctc       480
cccaccctga atctccaccc cctcccccca gaaactgaca cttggccttg tctaaggatg      540
ggttttccca aaatccttct gaaaaaaaca gaatttcaag agtcactccc tccgggtctc      600
agcctagaac atatgcagta tccctgacg tccataggg                              639
```

<210> SEQ ID NO 20
<211> LENGTH: 716
<212> TYPE: DNA
<213> ORGANISM: Mus musculus

<400> SEQUENCE: 20

```
aaactggcac agtaatggcg ggctgacaga caagggagtc tgtagcaccc gctgcctccg       60
cccacccctt ctccgagcaa ttaaaaggtg tttatgtggg gctggcagtg gcttctgcct      120
cccttccatt acgaacatta agagatcttg acccttccac tttccccgct cttgaaagga      180
gctgcagaca cgtggagcca attaggcgca cgcgtgggcg ccaagggcct gagcagcttt      240
ttctccctga ttgcggcgtt tacagctgat tattctcccc tcacccaaac agtgctgctt      300
cctggcaagg tgccacccag aggagccggc tgggggcccc tggggacagg ggaggactgg      360
attagtaaat gggcatctat cgaatggctt tcatatgtgt ggctggaagg gagaagggta      420
gggccaggaa tggtggcagc aagggcccag gtagcaatga gggttcttct aacccaccat      480
ttagggatag cgatcagaaa agggccctcg aggaggtgac ctaaatgtgt gtagaagctg      540
acggccacta cacacacaca cacacacaca cacacacata cacaagcatc cttgtccttg      600
gagtcggtca gcatgagcaa gagaaagatg ttcccagtgg ccatgagagt ggagccctcc      660
tccctactta catccaggtt ggatggccag gagatcctga gatccttcaa gactcc          716
```

<210> SEQ ID NO 21
<211> LENGTH: 147
<212> TYPE: DNA
<213> ORGANISM: Mus musculus

```
<400> SEQUENCE: 21
aagccacatc ctgggtggaa atatatggct tcaattccca ctcttccgga tgacctctgt    60
ggggagccct ggcttcacct tggtccagct tcatcccta gcctcgctgc caggaaggca    120
gtgaggtcag aggctggtgc tggcgtg                                        147

<210> SEQ ID NO 22
<211> LENGTH: 297
<212> TYPE: DNA
<213> ORGANISM: Mus musculus

<400> SEQUENCE: 22
cctacctggt gcccgccaac atctgggggc catcctggcc agcgccagcg tggtggtgaa    60
ggcactgtgc gccgtggtac tgtttctcta cctgctttcc ttcgctgtgg acacgggctg   120
cctggccgtc accccaggct acctttttccc acccaacttc tggatctgga ccctggccac   180
ccacgggctc atggaacagc acgtgtggga cgtggccatt agcctggcca cagtggttgt    240
ggccgggcga ttactggagc ccctctgggg agccttggag ctgctcatct tcttctc      297

<210> SEQ ID NO 23
<211> LENGTH: 101
<212> TYPE: DNA
<213> ORGANISM: Homo sapiens

<400> SEQUENCE: 23
aaacggacgg gcctccgctg aaccagtgag gccccagacg tgcgcataaa taacccctgc    60
gtgctgcacc acctggggag aggggagga ccacggtaaa t                        101

<210> SEQ ID NO 24
<211> LENGTH: 101
<212> TYPE: DNA
<213> ORGANISM: Homo sapiens

<400> SEQUENCE: 24
ggagcgagcg catagcaaaa gggacgcggg gtccttttct ctgccggtgg cactgggtag    60
ctgtggccag gtgtggtact ttgatggggc cagggctgg a                       101

<210> SEQ ID NO 25
<211> LENGTH: 101
<212> TYPE: DNA
<213> ORGANISM: Homo sapiens

<400> SEQUENCE: 25
gctcaaggaa gcgtcgcagg gtcacagatc tgggggaacc ccggggaaaa gcactgaggc    60
aaaaccgccg ctcgtctcct acaatatatg ggagggggag g                      101

<210> SEQ ID NO 26
<211> LENGTH: 547
<212> TYPE: DNA
<213> ORGANISM: Homo sapiens

<400> SEQUENCE: 26
ttgagtacgt tctggattac tcataagacc tttttttttt ccttccgggc gcaaaaccgt    60
gagctggatt tataatcgcc ctataaagct ccagaggcgg tcaggcacct gcagaggagc   120
cccgccgctc cgccgactag ctgccccgc gagcaacggc ctcgtgatttt ccccgccgat   180 ccggtccccg cctccccact ctgccccgc ctacccggaa gccgtgcagc cgcctctccg   240
aatctctctc ttctcctggc gctcgcgtgc gagagggaac tagcgagaac gaggaagcag   300
```

```
ctggaggtga cgccgggcag attacgcctg tcagggccga gccgagcgga tcgctgggcg    360
ctgtgcagag gaaaggcggg agtgcccggc tcgctgtcgc agagccgagg tgggtaagct    420
agcgaccacc tggacttccc agcgcccaac cgtggctttt cagccaggtc ctctcctccc    480
gcggcttctc aaccaacccc atcccagcgc cggccaccca acctcccgaa atgagtgctt    540
cctgccc                                                              547
```

<210> SEQ ID NO 27
<211> LENGTH: 101
<212> TYPE: DNA
<213> ORGANISM: Homo sapiens

<400> SEQUENCE: 27

```
cagcagccga aggcgctact aggaacggta acctgttact tttccagggg ccgtagtcga     60
cccgctgccc gagttgctgt gcgactgcgc gcgcgggct a                         101
```

<210> SEQ ID NO 28
<211> LENGTH: 201
<212> TYPE: DNA
<213> ORGANISM: Homo sapiens

<400> SEQUENCE: 28

```
gagtgcaagg tgactgtggt tcttctctgg ccaagtccga gggagaacgt aaagatatgg     60 gccttttttcc ccctctcacc ttgtctcacc aaagtcccta gtccccggag cagttagcct   120
ctttctttcc agggaattag ccagacacaa caacgggaac cagacaccga accagacatg   180
cccgccccgt gcgccctccc c                                              201
```

<210> SEQ ID NO 29
<211> LENGTH: 199
<212> TYPE: DNA
<213> ORGANISM: Homo sapiens

<400> SEQUENCE: 29

```
gctcgctgcc tttcctccct cttgtctctc cagagccgga tcttcaaggg gagcctccgt     60
gcccccggct gctcagtccc tccggtgtgc aggaccccgg aagtcctccc cgcacagctc   120
tcgcttctct ttgcagcctg ttttctgcgcc ggaccagtcg aggactctgg acagtagagg   180
ccccgggacg accgagctg                                                 199
```

<210> SEQ ID NO 30
<211> LENGTH: 1351
<212> TYPE: DNA
<213> ORGANISM: Homo sapiens

<400> SEQUENCE: 30

```
aaacggacgg gcctccgctg aaccagtgag gccccagacg tgcgcataaa taaccctgc      60 gtgctgcacc acctggggag agggggagga ccacggtaaa tggagcgagc gcatagcaaa   120
agggacgcgg ggtccttttc tctgccggtg gcactgggta gctgtggcca ggtgtggtac   180
tttgatgggg cccagggctg gagctcaagg aagcgtcgca gggtcacaga tctgggggaa   240
ccccggggaa aagcactgag gcaaaaccgc cgctcgtctc ctacaatata tgggaggggg   300
aggttgagta cgttctggat tactcataag acctttttttt tttccttccg ggcgcaaaac   360
cgtgagctgg atttataatc gccctataaa gctccagagg cggtcaggca cctgcagagg   420
agccccgccg ctccgccgac tagctgcccc cgcgagcaac ggcctcgtga tttcccgcc    480
```

```
gatccggtcc ccgctcccc actctgcccc cgcctacccc ggagccgtgc agccgcctct      540
ccgaatctct ctcttctcct ggcgctcgcg tgcgagaggg aactagcgag aacgaggaag      600
cagctggagg tgacgccggg cagattacgc ctgtcagggc cgagccgagc ggatcgctgg      660
gcgctgtgca gaggaaaggc gggagtgccc ggctcgctgt cgcagagccg aggtgggtaa      720
gctagcgacc acctggactt cccagcgccc aaccgtggct tttcagccag gtcctctcct      780
cccgcggctt ctcaaccaac cccatcccag cgccggccac ccaacctccc gaaatgagtg      840
cttcctgccc cagcagccga aggcgctact aggaacggta acctgttact tttccagggg      900
ccgtagtcga cccgctgccc gagttgctgt gcgactgcgc gcgcggggct agagtgcaag      960
gtgactgtgg ttcttctctg gccaagtccg agggagaacg taaagatatg ggccttttc     1020
ccctctcac cttgtctcac caaagtccct agtccccgga gcagttagcc tctttctttc     1080
cagggaatta gccagacaca caacgggaa ccagacaccc aaccagacat gcccgccccg     1140
tgcgccctcc ccgctcgctg cctttcctcc ctcttgtctc tccagagccg gatcttcaag     1200
gggagcctcc gtgcccccgg ctgctcagtc cctccggtgt gcaggacccc ggaagtcctc     1260
cccgcacagc tctcgcttct ctttgcagcc tgtttctgcg ccggaccagt cgaggactct     1320
ggacagtaga ggccccggga cgaccgagct g                                     1351

<210> SEQ ID NO 31
<211> LENGTH: 2051
<212> TYPE: DNA
<213> ORGANISM: Homo sapiens

<400> SEQUENCE: 31
ggaggaagcc atcaactaaa ctacaatgac tgtaagatac aaaattggga atggtaacat       60
attttgaagt tctgttgaca taagaatca tgatattaat gcccatggaa atgaaagggc      120
gatcaacact atggtttgaa aaggggggaaa ttgtagagca cagatgtgtt cgtgtggcag      180
tgtgctgtct ctagcaatac tcagagaaga gagagaacaa tgaaattctg attggcccca      240
gtgtgagccc agatgaggtt cagctgccaa cttctctttt cacatcttat gaaagtcatt      300
taagcacaac taacttttttt ttttttttt tttttttgag acagagtctt gctctgttgc      360
ccaggacaga gtgcagtagt gactcaatct cggctcactg cagcctccac ctcctaggct      420
caaacggtcc tcctgcatca gcctcccaag tagctggaat tacaggagtg gccccaccatg     480
cccagctaat ttttgtattt ttaatagata cggggggtttc accatatcac ccaggctggt      540
ctcgaactcc tggcctcaag tgatccacct gcctcggcct cccaaagtgc tgggattata      600
ggcgtcagcc actatgccca acccgaccaa cctttttaa aataaatatt taaaaaattg       660
gtatttcaca tatatactag tatttacatt tatccacaca aaacgacgg gcctccgctg      720
aaccagtgag gccccagacg tgcgcataaa taacccctgc gtgctgcacc acctggggag      780
aggggggagga ccacggtaaa tggagcgagc gcatagcaaa agggacgcgg ggtccttttc      840
tctgccggtg gcactgggta gctgtggcca ggtgtggtac tttgatgggg ccagggctg       900
gagctcaagg aagcgtcgca gggtcacaga tctgggggaa ccccggggaa aagcactgag      960
gcaaaaccgc cgctcgtctc ctacaatata tgggaggggg aggttgagta cgttctggat     1020
tactcataag acctttttttt ttccttccg ggcgcaaaac cgtgagctgg atttataatc     1080
gccctataaa gctccagagg cggtcaggca cctgcagagg agcccgccg ctccgccgac     1140
tagctgcccc cgcgagcaac ggcctcgtga tttccccgcc gatccggtcc ccgcctcccc     1200
actctgcccc cgcctacccc ggagccgtgc agccgcctct ccgaatctct ctcttctcct     1260
```

-continued

```
ggcgctcgcg tgcgagaggg aactagcgag aacgaggaag cagctggagg tgacgccggg      1320
cagattacgc ctgtcagggc cgagccgagc ggatcgctgg gcgctgtgca gaggaaaggc      1380
gggagtgccc ggctcgctgt cgcagagccg aggtgggtaa gctagcgacc acctggactt      1440
cccagcgccc aaccgtggct tttcagccag gtcctctcct cccgcggctt ctcaaccaac      1500
cccatcccag cgccggccac ccaacctccc gaaatgagtg cttcctgccc cagcagccga      1560
aggcgctact aggaacggta acctgttact tttccagggg ccgtagtcga cccgctgccc      1620
gagttgctgt gcgactgcgc gcgcggggct agagtgcaag gtgactgtgg ttcttctctg      1680
gccaagtccg agggagaacg taaagatatg ggccttttc cccctctcac cttgtctcac       1740
caaagtccct agtccccgga gcagttagcc tctttctttc cagggaatta gccagacaca      1800
acaacgggaa ccagacaccg aaccagacat gcccgccccg tgcgccctcc ccgctcgctg      1860
cctttcctcc ctcttgtctc tccagagccg gatcttcaag gggagcctcc gtgccccgg       1920 ctgctcagtc cctccggtgt gcaggacccc ggaagtcctc cccgcacagc tctcgcttct      1980 cttttgcagcc tgtttctgcg ccggaccagt cgaggactct ggacagtaga ggccccggga    2040
cgaccgagct g                                                            2051
```

<210> SEQ ID NO 32
<211> LENGTH: 1878
<212> TYPE: DNA
<213> ORGANISM: Unknown
<220> FEATURE:
<223> OTHER INFORMATION: Description of Unknown:
RE sequence

<400> SEQUENCE: 32

```
tcaacagggg gacacttggg aaagaaggat ggggacagag ccgagaggac tgttacacat        60
tagagaaaca tcagtgactg tgccagcttt ggggtagact gcacaaaagc cctgaggcag       120
cacaggcagg atccagtctg ctggtcccag gaagctaacc gtctcagaca gagcacaaag       180
caccgagaca tgtgccacaa ggcttgtgta gagaggtcag aggacagcgt acaggtccca       240
gagatcaaac tcaacctcac caggcttggc agcaagcctt taccaaccca cccccacccc       300
acccaccctg cacgcgcccc tctcccctcc ccatggtctc ccatggctat ctcacttggc       360
cctaaaatgt ttaaggatga cactggctgc tgagtggaaa tgagacagca gaagtcaaca       420
gtagatttta ggaaagccag agaaaaaggc ttgtgctgtt tttagaaagc caagggacaa       480
gctaagatag ggcccaagta atgctagtat ttacatttat ccacacaaaa cggacgggcc       540
tccgctgaac cagtgaggcc ccagacgtgc gcataaataa cccctgcgtg ctgcaccacc       600
tggggagagg gggaggacca cggtaaatgg agcgagcgca tagcaaaagg gacgcggggt       660
ccttttctct gccggtggca ctgggtagct gtggccaggt gtggtacttt gatggggccc       720
agggctggag ctcaaggaag cgtcgcaggg tcacagatct ggggggaaccc cggggaaaag      780 cactgaggca aaaccgccgc tcgtctccta caatatatgg gaggggagg ttgagtacgt        840 tctggattac tcataagacc tttttttttt ccttccgggc gcaaaaccgt gagctggatt       900
tataatcgcc ctataaagct ccagaggcgg tcaggcacct gcagaggagc cccgccgctc       960
cgccgactag ctgccccgc gagcaacggc ctcgtgattt ccccgccgat ccggtccccg      1020
cctccccact ctgcccccgc ctaccccgga gccgtgcagc cgcctctccg aatctctctc      1080
ttctcctggc gctcgcgtgc gagagggaac tagcgagaac gaggaagcag ctggaggtga     1140
cgccgggcag attacgcctg tcagggccga gccgagcgga tcgctgggcg ctgtgcagag     1200
```

| | |
|---|---|
| gaaaggcggg agtgcccggc tcgctgtcgc agagccgagg tgggtaagct agcgaccacc | 1260 |
| tggacttccc agcgcccaac cgtggctttt cagccaggtc ctctcctccc gcggcttctc | 1320 |
| aaccaacccc atcccagcgc cggccaccca acctcccgaa atgagtgctt cctgccccag | 1380 |
| cagccgaagg cgctactagg aacggtaacc tgttactttt ccaggggccg tagtcgaccc | 1440 |
| gctgcccgag ttgctgtgcg actgcgcgcg cggggctaga gtgcaaggtg actgtggttc | 1500 |
| ttctctggcc aagtccgagg gagaacgtaa agatatgggc cttttccccc ctctcacctt | 1560 |
| gtctcaccaa agtccctagt ccccggagca gttagcctct ttctttccag ggaattagcc | 1620 |
| agacacaaca acgggaacca gacaccgaac cagacatgcc cgccccgtgc gccctccccg | 1680 |
| ctcgctgcct ttcctccctc ttgtctctcc agagccggat cttcaagggg agcctccgtg | 1740 |
| cccccggctg ctcagtccct ccggtgtgca ggaccccgga agtcctcccc gcacagctct | 1800 |
| cgcttctctt tgcagcctgt ttctgcgccg gaccagtcga ggactctgga cagtagaggc | 1860 |
| cccgggacga ccgagctg | 1878 |

<210> SEQ ID NO 33
<211> LENGTH: 19
<212> TYPE: DNA
<213> ORGANISM: Homo sapiens

<400> SEQUENCE: 33

| | |
|---|---|
| atttacattt atccacaca | 19 |

<210> SEQ ID NO 34
<211> LENGTH: 800
<212> TYPE: DNA
<213> ORGANISM: Mus musculus

<400> SEQUENCE: 34

| | |
|---|---|
| tgccgctgga ctctcttcca aggaactagg agaaccaaga tccgttttc tgccaagggc | 60 |
| tgccccccc acgccccaa cccctcacc ccgatcccca cagaaagaaa tcttgaggta | 120 |
| gctggagctt cttctgtggg tgtgacagga ctgccattct cctctgtagt ctgcagaagc | 180 |
| ctgccattcc accatttaaa cctgtgactc caggccttaa gcctgttgaa ggtcgagtcc | 240 |
| cagaagggtc atatgtgcaa ctgcctaggg agagttccca ctcgcagggc caagaggagt | 300 |
| cccccggtct gaggtgtggg ggcggggacg tgcactgggc gctgggacca cggctggggc | 360 |
| tcaggactcg cgagcttgga ttcggatcgg tttgcgcgag ccagtagggc aggctccggg | 420 |
| gtgaacgggg acgaggggcg cgcgggcaca ggcgggcgcg tgaccgcggc ggggcgcgc | 480 |
| ggaggcgggc cggccaagga gagggaggga gggaatgagg gagggagcga caggggaggg | 540 |
| cggcgccggc aggttggcgg cggccgctat ttgagcgcag gtcccgggcc aggcgctcaa | 600 |
| agcgcttgga gccagcgcgg cggggagatc gctgcgcgca gcccgcagag gcgctgcggc | 660 |
| cagtgcagcc ccggaggccc cgcgcggaga aggaggtgga gaagaggccg gctttccgcc | 720 |
| cgccgcccgc gcccccccac ctccatcccg ccgccgccgt cccccctccc tccccgcggc | 780 |
| gccgcatctt gaatggaaac | 800 |

<210> SEQ ID NO 35
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
gagtaattca tacaaaagga ctcgcccctg ccttggggaa tcccagggac cgtcgttaaa        60
ctcccactaa cgtagaaccc agagatcgct gcgttcccgc ccctcaccc gcccgctctc        120
gtcatcactg aggtggagaa gagcatgcgt gaggctccgg tgcccgtcag tgggcagagc       180
gcacatcgcc cacagtcccc gagaagttgg ggggaggggt cggcaattga accggtgcct      240
agagaaggtg gcgcgggta aactgggaaa gtgatgtcgt gtactggctc cgccttttc        300
ccgagggtgg gggagaaccg tatataagtg cagtagtcgc cgtgaacgtt cttttcgca       360
acgggttttgc cgccagaaca caggtaagtg ccgtgtgtgg ttcccgcggg cctggcctct    420
ttacgggtta tggcccttgc gtgccttgaa ttacttccac gccctggct gcagtacgtg       480
attcttgatc ccgagcttcg ggttggaagt gggtgggaga gttcgaggcc ttgcgcttaa      540
ggagcccctt cgcctcgtgc ttgagttgag gcctggcttg ggcgctgggg ccgccgcgtg      600
cgaatctggt ggcaccttcg cgcctgtctc gctgctttcg ataagtctct agccatttaa     660
aattttgat gacctgctgc gacgcttttt ttctggcaag atagtcttgt aaatgcgggc       720
caagatctgc acactggtat ttcggttttt ggggccgcgg gcggcgacgg ggcccgtgcg      780
tcccagcgca catgttcggc gaggcgggc ctgcgagcgc ggccaccgag aatcggacgg       840
gggtagtctc aagctggccg gcctgctctg gtgcctggcc tcgcgccgcc gtgtatcgcc     900
ccgccctggg cggcaaggct ggcccggtcg gcaccagttg cgtgagcgga agatggccg       960
cttcccggcc ctgctgcagg gagctcaaaa tggaggacgc ggcgctcggg agagcgggcg     1020
ggtgagtcac ccacacaaag gaaaagggcc tttccgtcct cagccgtcgc ttcatgtgac     1080
tccacggagt accgggcgcc gtccaggcac ctcgattagt tctcgagctt ttggagtacg    1140
tcgtctttag gttgggggga ggggttttat gcgatggagt ttccccacac tgagtgggtg    1200
gagactgaag ttaggccagc ttggcacttg atgtaattct ccttggaatt tgcccttttt    1260
gagtttggat cttggttcat tctcaagcct cagacagtgg ttcaaagttt ttttcttcca    1320
tttcaggtgt cgtga                                                      1335
```

<210> SEQ ID NO 36
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
```

```
                100                 105                 110
Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu
            210                 215                 220

<210> SEQ ID NO 37
<211> LENGTH: 218
<212> TYPE: PRT
<213> ORGANISM: Unknown
<220> FEATURE:
<223> OTHER INFORMATION: Description of Unknown:
      SCN1B sequence

<400> SEQUENCE: 37

Met Gly Thr Leu Leu Ala Leu Val Val Gly Ala Ala Leu Val Ser Ser
1               5                   10                  15

Ala Trp Gly Gly Cys Val Glu Val Asp Ser Asp Thr Glu Ala Val Tyr
            20                  25                  30

Gly Met Thr Phe Lys Ile Leu Cys Ile Ser Cys Lys Arg Arg Ser Glu
        35                  40                  45

Thr Thr Ala Glu Thr Phe Thr Glu Trp Thr Phe Arg Gln Lys Gly Thr
    50                  55                  60

Glu Glu Phe Val Lys Ile Leu Arg Tyr Glu Asn Glu Val Leu Gln Leu
65                  70                  75                  80

Glu Glu Asp Glu Arg Phe Glu Gly Arg Val Val Trp Asn Gly Ser Arg
                85                  90                  95

Gly Thr Lys Asp Leu Gln Asp Leu Ser Ile Phe Ile Thr Asn Val Thr
            100                 105                 110

Tyr Asn His Ser Gly Asp Tyr Glu Cys His Val Tyr Arg Leu Leu Phe
        115                 120                 125

Phe Asp Asn Tyr Glu His Asn Thr Ser Val Val Lys Lys Ile His Leu
    130                 135                 140

Glu Val Val Asp Lys Ala Asn Arg Asp Met Ala Ser Ile Val Ser Glu
145                 150                 155                 160

Ile Met Met Tyr Val Leu Ile Val Val Leu Thr Ile Trp Leu Val Ala
                165                 170                 175

Glu Met Val Tyr Cys Tyr Lys Lys Ile Ala Ala Ala Thr Glu Ala Ala
            180                 185                 190

Ala Gln Glu Asn Ala Ser Glu Tyr Leu Ala Ile Thr Ser Glu Ser Lys
        195                 200                 205

Glu Asn Cys Thr Gly Val Gln Val Ala Glu
    210                 215

<210> SEQ ID NO 38
<211> LENGTH: 215
```

```
<212> TYPE: PRT
<213> ORGANISM: Unknown
<220> FEATURE:
<223> OTHER INFORMATION: Description of Unknown:
      SCN2B sequence

<400> SEQUENCE: 38

Met His Arg Asp Ala Trp Leu Pro Arg Pro Ala Phe Ser Leu Thr Gly
1               5                   10                  15

Leu Ser Leu Phe Phe Ser Leu Val Pro Pro Gly Arg Ser Met Glu Val
                20                  25                  30

Thr Val Pro Ala Thr Leu Asn Val Leu Asn Gly Ser Asp Ala Arg Leu
            35                  40                  45

Pro Cys Thr Phe Asn Ser Cys Tyr Thr Val Asn His Lys Gln Phe Ser
    50                  55                  60

Leu Asn Trp Thr Tyr Gln Glu Cys Asn Asn Cys Ser Glu Glu Met Phe
65                  70                  75                  80

Leu Gln Phe Arg Met Lys Ile Ile Asn Leu Lys Leu Glu Arg Phe Gln
                85                  90                  95

Asp Arg Val Glu Phe Ser Gly Asn Pro Ser Lys Tyr Asp Val Ser Val
                100                 105                 110

Met Leu Arg Asn Val Gln Pro Glu Asp Glu Gly Ile Tyr Asn Cys Tyr
                115                 120                 125

Ile Met Asn Pro Pro Asp Arg His Arg Gly His Gly Lys Ile His Leu
130                 135                 140

Gln Val Leu Met Glu Glu Pro Pro Glu Arg Asp Ser Thr Val Ala Val
145                 150                 155                 160

Ile Val Gly Ala Ser Val Gly Gly Phe Leu Ala Val Val Ile Leu Val
                165                 170                 175

Leu Met Val Val Lys Cys Val Arg Arg Lys Lys Glu Gln Lys Leu Ser
                180                 185                 190

Thr Asp Asp Leu Lys Thr Glu Glu Glu Gly Lys Thr Asp Gly Glu Gly
                195                 200                 205

Asn Pro Asp Asp Gly Ala Lys
                210                 215

<210> SEQ ID NO 39
<211> LENGTH: 2009
<212> TYPE: PRT
<213> ORGANISM: Unknown
<220> FEATURE:
<223> OTHER INFORMATION: Description of Unknown:
      SCN1A sequence

<400> SEQUENCE: 39

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
                20                  25                  30

Lys Ala Lys Asn Pro Lys Pro Asp Lys Lys Asp Asp Asp Glu Asn Gly
            35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95
```

```
Lys Ala Ile Phe Arg Phe Ser Ala Thr Ser Ala Leu Tyr Ile Leu Thr
                100                 105                 110

Pro Phe Asn Pro Leu Arg Lys Ile Ala Ile Lys Ile Leu Val His Ser
            115                 120                 125

Leu Phe Ser Met Leu Ile Met Cys Thr Ile Leu Thr Asn Cys Val Phe
        130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Ala Ala Thr Ala
450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
```

-continued

```
              515                 520                 525
Ile Arg Arg Lys Gly Phe Arg Phe Ser Ile Glu Gly Asn Arg Leu Thr
530                 535                 540
Tyr Glu Lys Arg Tyr Ser Ser Pro His Gln Ser Leu Leu Ser Ile Arg
545                 550                 555                 560
Gly Ser Leu Phe Ser Pro Arg Arg Asn Ser Arg Thr Ser Leu Phe Ser
                    565                 570                 575
Phe Arg Gly Arg Ala Lys Asp Val Gly Ser Glu Asn Asp Phe Ala Asp
                580                 585                 590
Asp Glu His Ser Thr Phe Glu Asp Asn Glu Ser Arg Arg Asp Ser Leu
            595                 600                 605
Phe Val Pro Arg Arg His Gly Glu Arg Arg Asn Ser Asn Leu Ser Gln
        610                 615                 620
Thr Ser Arg Ser Ser Arg Met Leu Ala Val Phe Pro Ala Asn Gly Lys
625                 630                 635                 640
Met His Ser Thr Val Asp Cys Asn Gly Val Val Ser Leu Val Gly Gly
                    645                 650                 655
Pro Ser Val Pro Thr Ser Pro Val Gly Gln Leu Leu Pro Glu Val Ile
                660                 665                 670
Ile Asp Lys Pro Ala Thr Asp Asn Gly Thr Thr Thr Glu Thr Glu
            675                 680                 685
Met Arg Lys Arg Arg Ser Ser Phe His Val Ser Met Asp Phe Leu
690                 695                 700
Glu Asp Pro Ser Gln Arg Gln Arg Ala Met Ser Ile Ala Ser Ile Leu
705                 710                 715                 720
Thr Asn Thr Val Glu Glu Leu Glu Glu Ser Arg Gln Lys Cys Pro Pro
                    725                 730                 735
Cys Trp Tyr Lys Phe Ser Asn Ile Phe Leu Ile Trp Asp Cys Ser Pro
                740                 745                 750
Tyr Trp Leu Lys Val Lys His Val Val Asn Leu Val Val Met Asp Pro
            755                 760                 765
Phe Val Asp Leu Ala Ile Thr Ile Cys Ile Val Leu Asn Thr Leu Phe
        770                 775                 780
Met Ala Met Glu His Tyr Pro Met Thr Asp His Phe Asn Asn Val Leu
785                 790                 795                 800
Thr Val Gly Asn Leu Val Phe Thr Gly Ile Phe Thr Ala Glu Met Phe
                    805                 810                 815
Leu Lys Ile Ile Ala Met Asp Pro Tyr Tyr Tyr Phe Gln Glu Gly Trp
                820                 825                 830
Asn Ile Phe Asp Gly Phe Ile Val Thr Leu Ser Leu Val Glu Leu Gly
            835                 840                 845
Leu Ala Asn Val Glu Gly Leu Ser Val Leu Arg Ser Phe Arg Leu Leu
        850                 855                 860
Arg Val Phe Lys Leu Ala Lys Ser Trp Pro Thr Leu Asn Met Leu Ile
865                 870                 875                 880
Lys Ile Ile Gly Asn Ser Val Gly Ala Leu Gly Asn Leu Thr Leu Val
                    885                 890                 895
Leu Ala Ile Ile Val Phe Ile Phe Ala Val Val Gly Met Gln Leu Phe
                900                 905                 910
Gly Lys Ser Tyr Lys Asp Cys Val Cys Lys Ile Ala Ser Asp Cys Gln
            915                 920                 925
Leu Pro Arg Trp His Met Asn Asp Phe Phe His Ser Phe Leu Ile Val
        930                 935                 940
```

-continued

```
Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu Ala Ala Thr Asp Asp Asp Asn Glu
        995                 1000                1005

Met Asn Asn Leu Gln Ile Ala Val Asp Arg Met His Lys Gly Val
    1010                1015                1020

Ala Tyr Val Lys Arg Lys Ile Tyr Glu Phe Ile Gln Gln Ser Phe
    1025                1030                1035

Ile Arg Lys Gln Lys Ile Leu Asp Glu Ile Lys Pro Leu Asp Asp
    1040                1045                1050

Leu Asn Asn Lys Lys Asp Ser Cys Met Ser Asn His Thr Ala Glu
    1055                1060                1065

Ile Gly Lys Asp Leu Asp Tyr Leu Lys Asp Val Asn Gly Thr Thr
    1070                1075                1080

Ser Gly Ile Gly Thr Gly Ser Ser Val Glu Lys Tyr Ile Ile Asp
    1085                1090                1095

Glu Ser Asp Tyr Met Ser Phe Ile Asn Asn Pro Ser Leu Thr Val
    1100                1105                1110

Thr Val Pro Ile Ala Val Gly Glu Ser Asp Phe Glu Asn Leu Asn
    1115                1120                1125

Thr Glu Asp Phe Ser Ser Glu Ser Asp Leu Glu Glu Ser Lys Glu
    1130                1135                1140

Lys Leu Asn Glu Ser Ser Ser Ser Ser Glu Gly Ser Thr Val Asp
    1145                1150                1155

Ile Gly Ala Pro Val Glu Glu Gln Pro Val Val Glu Pro Glu Glu
    1160                1165                1170

Thr Leu Glu Pro Glu Ala Cys Phe Thr Glu Gly Cys Val Gln Arg
    1175                1180                1185

Phe Lys Cys Cys Gln Ile Asn Val Glu Glu Gly Arg Gly Lys Gln
    1190                1195                1200

Trp Trp Asn Leu Arg Arg Thr Cys Phe Arg Ile Val Glu His Asn
    1205                1210                1215

Trp Phe Glu Thr Phe Ile Val Phe Met Ile Leu Leu Ser Ser Gly
    1220                1225                1230

Ala Leu Ala Phe Glu Asp Ile Tyr Ile Asp Gln Arg Lys Thr Ile
    1235                1240                1245

Lys Thr Met Leu Glu Tyr Ala Asp Lys Val Phe Thr Tyr Ile Phe
    1250                1255                1260

Ile Leu Glu Met Leu Leu Lys Trp Val Ala Tyr Gly Tyr Gln Thr
    1265                1270                1275

Tyr Phe Thr Asn Ala Trp Cys Trp Leu Asp Phe Leu Ile Val Asp
    1280                1285                1290

Val Ser Leu Val Ser Leu Thr Ala Asn Ala Leu Gly Tyr Ser Glu
    1295                1300                1305

Leu Gly Ala Ile Lys Ser Leu Arg Thr Leu Arg Ala Leu Arg Pro
    1310                1315                1320

Leu Arg Ala Leu Ser Arg Phe Glu Gly Met Arg Val Val Val Asn
    1325                1330                1335
```

```
Ala Leu Leu Gly Ala Ile Pro Ser Ile Met Asn Val Leu Leu Val
    1340            1345            1350

Cys Leu Ile Phe Trp Leu Ile Phe Ser Ile Met Gly Val Asn Leu
    1355            1360            1365

Phe Ala Gly Lys Phe Tyr His Cys Ile Asn Thr Thr Thr Gly Asp
    1370            1375            1380

Arg Phe Asp Ile Glu Asp Val Asn Asn His Thr Asp Cys Leu Lys
    1385            1390            1395

Leu Ile Glu Arg Asn Glu Thr Ala Arg Trp Lys Asn Val Lys Val
    1400            1405            1410

Asn Phe Asp Asn Val Gly Phe Gly Tyr Leu Ser Leu Leu Gln Val
    1415            1420            1425

Ala Thr Phe Lys Gly Trp Met Asp Ile Met Tyr Ala Ala Val Asp
    1430            1435            1440

Ser Arg Asn Val Glu Leu Gln Pro Lys Tyr Glu Glu Ser Leu Tyr
    1445            1450            1455

Met Tyr Leu Tyr Phe Val Ile Phe Ile Ile Phe Gly Ser Phe Phe
    1460            1465            1470

Thr Leu Asn Leu Phe Ile Gly Val Ile Ile Asp Asn Phe Asn Gln
    1475            1480            1485

Gln Lys Lys Lys Phe Gly Gly Gln Asp Ile Phe Met Thr Glu Glu
    1490            1495            1500

Gln Lys Lys Tyr Tyr Asn Ala Met Lys Lys Leu Gly Ser Lys Lys
    1505            1510            1515

Pro Gln Lys Pro Ile Pro Arg Pro Gly Asn Lys Phe Gln Gly Met
    1520            1525            1530

Val Phe Asp Phe Val Thr Arg Gln Val Phe Asp Ile Ser Ile Met
    1535            1540            1545

Ile Leu Ile Cys Leu Asn Met Val Thr Met Met Val Glu Thr Asp
    1550            1555            1560

Asp Gln Ser Glu Tyr Val Thr Thr Ile Leu Ser Arg Ile Asn Leu
    1565            1570            1575

Val Phe Ile Val Leu Phe Thr Gly Glu Cys Val Leu Lys Leu Ile
    1580            1585            1590

Ser Leu Arg His Tyr Tyr Phe Thr Ile Gly Trp Asn Ile Phe Asp
    1595            1600            1605

Phe Val Val Val Ile Leu Ser Ile Val Gly Met Phe Leu Ala Glu
    1610            1615            1620

Leu Ile Glu Lys Tyr Phe Val Ser Pro Thr Leu Phe Arg Val Ile
    1625            1630            1635

Arg Leu Ala Arg Ile Gly Arg Ile Leu Arg Leu Ile Lys Gly Ala
    1640            1645            1650

Lys Gly Ile Arg Thr Leu Leu Phe Ala Leu Met Met Ser Leu Pro
    1655            1660            1665

Ala Leu Phe Asn Ile Gly Leu Leu Leu Phe Leu Val Met Phe Ile
    1670            1675            1680

Tyr Ala Ile Phe Gly Met Ser Asn Phe Ala Tyr Val Lys Arg Glu
    1685            1690            1695

Val Gly Ile Asp Asp Met Phe Asn Phe Glu Thr Phe Gly Asn Ser
    1700            1705            1710

Met Ile Cys Leu Phe Gln Ile Thr Thr Ser Ala Gly Trp Asp Gly
    1715            1720            1725

Leu Leu Ala Pro Ile Leu Asn Ser Lys Pro Pro Asp Cys Asp Pro
```

```
                        1730                1735                1740

Asn Lys Val Asn Pro Gly Ser Ser Val Lys Gly Asp Cys Gly Asn
        1745                1750                1755

Pro Ser Val Gly Ile Phe Phe Val Ser Tyr Ile Ile Ile Ser
    1760                1765                1770

Phe Leu Val Val Val Asn Met Tyr Ile Ala Val Ile Leu Glu Asn
        1775                1780                1785

Phe Ser Val Ala Thr Glu Glu Ser Ala Glu Pro Leu Ser Glu Asp
        1790                1795                1800

Asp Phe Glu Met Phe Tyr Glu Val Trp Glu Lys Phe Asp Pro Asp
        1805                1810                1815

Ala Thr Gln Phe Met Glu Phe Glu Lys Leu Ser Gln Phe Ala Ala
        1820                1825                1830

Ala Leu Glu Pro Pro Leu Asn Leu Pro Gln Pro Asn Lys Leu Gln
        1835                1840                1845

Leu Ile Ala Met Asp Leu Pro Met Val Ser Gly Asp Arg Ile His
        1850                1855                1860

Cys Leu Asp Ile Leu Phe Ala Phe Thr Lys Arg Val Leu Gly Glu
        1865                1870                1875

Ser Gly Glu Met Asp Ala Leu Arg Ile Gln Met Glu Glu Arg Phe
        1880                1885                1890

Met Ala Ser Asn Pro Ser Lys Val Ser Tyr Gln Pro Ile Thr Thr
        1895                1900                1905

Thr Leu Lys Arg Lys Gln Glu Glu Val Ser Ala Val Ile Ile Gln
        1910                1915                1920

Arg Ala Tyr Arg Arg His Leu Leu Lys Arg Thr Val Lys Gln Ala
        1925                1930                1935

Ser Phe Thr Tyr Asn Lys Asn Lys Ile Lys Gly Gly Ala Asn Leu
        1940                1945                1950

Leu Ile Lys Glu Asp Met Ile Ile Asp Arg Ile Asn Glu Asn Ser
        1955                1960                1965

Ile Thr Glu Lys Thr Asp Leu Thr Met Ser Thr Ala Ala Cys Pro
        1970                1975                1980

Pro Ser Tyr Asp Arg Val Thr Lys Pro Ile Val Glu Lys His Glu
        1985                1990                1995

Gln Glu Gly Lys Asp Glu Lys Ala Lys Gly Lys
        2000                2005

<210> SEQ ID NO 40
<211> LENGTH: 603
<212> TYPE: PRT
<213> ORGANISM: Unknown
<220> FEATURE:
<223> OTHER INFORMATION: Description of Unknown:
      STXBP1 sequence

<400> SEQUENCE: 40

Met Ala Pro Ile Gly Leu Lys Ala Val Val Gly Glu Lys Ile Met His
1               5                   10                  15

Asp Val Ile Lys Lys Val Lys Lys Gly Glu Trp Lys Val Leu Val
                20                  25                  30

Val Asp Gln Leu Ser Met Arg Met Leu Ser Ser Cys Cys Lys Met Thr
                35                  40                  45

Asp Ile Met Thr Glu Gly Ile Thr Ile Val Glu Asp Ile Asn Lys Arg
        50                  55                  60
```

-continued

```
Arg Glu Pro Leu Pro Ser Leu Glu Ala Val Tyr Leu Ile Thr Pro Ser
 65                  70                  75                  80

Glu Lys Ser Val His Ser Leu Ile Ser Asp Phe Lys Asp Pro Pro Thr
                 85                  90                  95

Ala Lys Tyr Arg Ala Ala His Val Phe Phe Thr Asp Ser Cys Pro Asp
            100                 105                 110

Ala Leu Phe Asn Glu Leu Val Lys Ser Arg Ala Ala Lys Val Ile Lys
        115                 120                 125

Thr Leu Thr Glu Ile Asn Ile Ala Phe Leu Pro Tyr Glu Ser Gln Val
    130                 135                 140

Tyr Ser Leu Asp Ser Ala Asp Ser Phe Gln Ser Phe Tyr Ser Pro His
145                 150                 155                 160

Lys Ala Gln Met Lys Asn Pro Ile Leu Glu Arg Leu Ala Glu Gln Ile
                165                 170                 175

Ala Thr Leu Cys Ala Thr Leu Lys Glu Tyr Pro Ala Val Arg Tyr Arg
            180                 185                 190

Gly Glu Tyr Lys Asp Asn Ala Leu Leu Ala Gln Leu Ile Gln Asp Lys
        195                 200                 205

Leu Asp Ala Tyr Lys Ala Asp Pro Thr Met Gly Glu Gly Pro Asp
    210                 215                 220

Lys Ala Arg Ser Gln Leu Leu Ile Leu Asp Arg Gly Phe Asp Pro Ser
225                 230                 235                 240

Ser Pro Val Leu His Glu Leu Thr Phe Gln Ala Met Ser Tyr Asp Leu
                245                 250                 255

Leu Pro Ile Glu Asn Asp Val Tyr Lys Tyr Glu Thr Ser Gly Ile Gly
            260                 265                 270

Glu Ala Arg Val Lys Glu Val Leu Leu Asp Glu Asp Asp Leu Trp
        275                 280                 285

Ile Ala Leu Arg His Lys His Ile Ala Glu Val Ser Gln Glu Val Thr
    290                 295                 300

Arg Ser Leu Lys Asp Phe Ser Ser Ser Lys Arg Met Asn Thr Gly Glu
305                 310                 315                 320

Lys Thr Thr Met Arg Asp Leu Ser Gln Met Leu Lys Lys Met Pro Gln
                325                 330                 335

Tyr Gln Lys Glu Leu Ser Lys Tyr Ser Thr His Leu His Leu Ala Glu
            340                 345                 350

Asp Cys Met Lys His Tyr Gln Gly Thr Val Asp Lys Leu Cys Arg Val
        355                 360                 365

Glu Gln Asp Leu Ala Met Gly Thr Asp Ala Glu Gly Glu Lys Ile Lys
    370                 375                 380

Asp Pro Met Arg Ala Ile Val Pro Ile Leu Leu Asp Ala Asn Val Ser
385                 390                 395                 400

Thr Tyr Asp Lys Ile Arg Ile Leu Leu Tyr Ile Phe Leu Lys Asn
                405                 410                 415

Gly Ile Thr Glu Glu Asn Leu Asn Lys Leu Ile Gln His Ala Gln Ile
            420                 425                 430

Pro Pro Glu Asp Ser Glu Ile Ile Thr Asn Met Ala His Leu Gly Val
        435                 440                 445

Pro Ile Val Thr Asp Ser Thr Leu Arg Arg Arg Ser Lys Pro Glu Arg
    450                 455                 460

Lys Glu Arg Ile Ser Glu Gln Thr Tyr Gln Leu Ser Arg Trp Thr Pro
465                 470                 475                 480

Ile Ile Lys Asp Ile Met Glu Asp Thr Ile Glu Asp Lys Leu Asp Thr
```

```
                     485                 490                 495
Lys His Tyr Pro Tyr Ile Ser Thr Arg Ser Ser Ala Ser Phe Ser Thr
                500                 505                 510

Thr Ala Val Ser Ala Arg Tyr Gly His Trp His Lys Asn Lys Ala Pro
                515                 520                 525

Gly Glu Tyr Arg Ser Gly Pro Arg Leu Ile Ile Phe Ile Leu Gly Gly
            530                 535                 540

Val Ser Leu Asn Glu Met Arg Cys Ala Tyr Glu Val Thr Gln Ala Asn
545                 550                 555                 560

Gly Lys Trp Glu Val Leu Ile Gly Ser Thr His Ile Leu Thr Pro Thr
                565                 570                 575

Lys Phe Leu Met Asp Leu Arg His Pro Asp Phe Arg Glu Ser Ser Arg
                580                 585                 590

Val Ser Phe Glu Asp Gln Ala Pro Thr Met Glu
                595                 600

<210> SEQ ID NO 41
<211> LENGTH: 511
<212> TYPE: PRT
<213> ORGANISM: Unknown
<220> FEATURE:
<223> OTHER INFORMATION: Description of Unknown:
      Kv3.1 sequence

<400> SEQUENCE: 41

Met Gly Gln Gly Asp Glu Ser Glu Arg Ile Val Ile Asn Val Gly Gly
1               5                   10                  15

Thr Arg His Gln Thr Tyr Arg Ser Thr Leu Arg Thr Leu Pro Gly Thr
                20                  25                  30

Arg Leu Ala Trp Leu Ala Glu Pro Asp Ala His Ser His Phe Asp Tyr
            35                  40                  45

Asp Pro Arg Ala Asp Glu Phe Phe Phe Asp Arg His Pro Gly Val Phe
    50                  55                  60

Ala His Ile Leu Asn Tyr Tyr Arg Thr Gly Lys Leu His Cys Pro Ala
65                  70                  75                  80

Asp Val Cys Gly Pro Leu Tyr Glu Glu Glu Leu Ala Phe Trp Gly Ile
                85                  90                  95

Asp Glu Thr Asp Val Glu Pro Cys Cys Trp Met Thr Tyr Arg Gln His
            100                 105                 110

Arg Asp Ala Glu Glu Ala Leu Asp Ser Phe Gly Gly Ala Pro Leu Asp
    115                 120                 125

Asn Ser Ala Asp Asp Ala Asp Ala Asp Gly Pro Gly Asp Ser Gly Asp
130                 135                 140

Gly Glu Asp Glu Leu Glu Met Thr Lys Arg Leu Ala Leu Ser Asp Ser
145                 150                 155                 160

Pro Asp Gly Arg Pro Gly Gly Phe Trp Arg Arg Trp Gln Pro Arg Ile
                165                 170                 175

Trp Ala Leu Phe Glu Asp Pro Tyr Ser Ser Arg Tyr Ala Arg Tyr Val
            180                 185                 190

Ala Phe Ala Ser Leu Phe Phe Ile Leu Val Ser Ile Thr Thr Phe Cys
    195                 200                 205

Leu Glu Thr His Glu Arg Phe Asn Pro Ile Val Asn Lys Thr Glu Ile
    210                 215                 220

Glu Asn Val Arg Asn Gly Thr Gln Val Arg Tyr Tyr Arg Glu Ala Glu
225                 230                 235                 240
```

-continued

Thr Glu Ala Phe Leu Thr Tyr Ile Glu Gly Val Cys Val Val Trp Phe
                245                 250                 255

Thr Phe Glu Phe Leu Met Arg Val Ile Phe Cys Pro Asn Lys Val Glu
            260                 265                 270

Phe Ile Lys Asn Ser Leu Asn Ile Ile Asp Phe Val Ala Ile Leu Pro
        275                 280                 285

Phe Tyr Leu Glu Val Gly Leu Ser Gly Leu Ser Ser Lys Ala Ala Lys
    290                 295                 300

Asp Val Leu Gly Phe Leu Arg Val Val Arg Phe Val Arg Ile Leu Arg
305                 310                 315                 320

Ile Phe Lys Leu Thr Arg His Phe Val Gly Leu Arg Val Leu Gly His
                325                 330                 335

Thr Leu Arg Ala Ser Thr Asn Glu Phe Leu Leu Leu Ile Ile Phe Leu
            340                 345                 350

Ala Leu Gly Val Leu Ile Phe Ala Thr Met Ile Tyr Tyr Ala Glu Arg
        355                 360                 365

Ile Gly Ala Gln Pro Asn Asp Pro Ser Ala Ser Glu His Thr His Phe
    370                 375                 380

Lys Asn Ile Pro Ile Gly Phe Trp Trp Ala Val Val Thr Met Thr Thr
385                 390                 395                 400

Leu Gly Tyr Gly Asp Met Tyr Pro Gln Thr Trp Ser Gly Met Leu Val
                405                 410                 415

Gly Ala Leu Cys Ala Leu Ala Gly Val Leu Thr Ile Ala Met Pro Val
            420                 425                 430

Pro Val Ile Val Asn Asn Phe Gly Met Tyr Tyr Ser Leu Ala Met Ala
        435                 440                 445

Lys Gln Lys Leu Pro Lys Lys Lys Lys His Ile Pro Arg Pro Pro
    450                 455                 460

Gln Leu Gly Ser Pro Asn Tyr Cys Lys Ser Val Val Asn Ser Pro His
465                 470                 475                 480

His Ser Thr Gln Ser Asp Thr Cys Pro Leu Ala Gln Glu Glu Ile Leu
                485                 490                 495

Glu Ile Asn Arg Ala Gly Arg Lys Pro Leu Arg Gly Met Ser Ile
            500                 505                 510

<210> SEQ ID NO 42
<211> LENGTH: 639
<212> TYPE: PRT
<213> ORGANISM: Unknown
<220> FEATURE:
<223> OTHER INFORMATION: Description of Unknown:
    Kv3.2 sequence

<400> SEQUENCE: 42

Met Gly Lys Ile Glu Ser Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
    50                  55                  60

Pro Arg Pro Pro Pro Leu Ser Pro Val Pro Ser Gly Cys Phe Glu Gly
65                  70                  75                  80

Gly Ala Gly Asn Cys Ser Ser His Gly Gly Asn Gly Gly Asn Gly Gly
                85                  90                  95

-continued

Ser Asp His Pro Gly Gly Arg Glu Phe Phe Asp Arg His Pro
                100                 105                 110

Gly Val Phe Ala Tyr Val Leu Asn Tyr Tyr Arg Thr Gly Lys Leu His
            115                 120                 125

Cys Pro Ala Asp Val Cys Gly Pro Leu Phe Glu Glu Leu Ala Phe
        130                 135                 140

Trp Gly Ile Asp Glu Thr Asp Val Glu Pro Cys Cys Trp Met Thr Tyr
145                 150                 155                 160

Arg Gln His Arg Asp Ala Glu Glu Ala Leu Asp Ile Phe Glu Thr Pro
                165                 170                 175

Asp Leu Ile Gly Gly Asp Pro Gly Asp Glu Asp Leu Ala Ala Lys
            180                 185                 190

Arg Leu Gly Ile Glu Asp Ala Ala Gly Leu Gly Gly Pro Asp Gly Lys
            195                 200                 205

Ser Gly Arg Trp Arg Lys Leu Gln Pro Arg Met Trp Ala Leu Phe Glu
    210                 215                 220

Asp Pro Tyr Ser Ser Arg Ala Ala Arg Phe Ile Ala Phe Ala Ser Leu
225                 230                 235                 240

Phe Phe Ile Leu Val Ser Ile Thr Thr Phe Cys Leu Glu Thr His Glu
                245                 250                 255

Ala Phe Asn Ile Val Lys Asn Lys Thr Glu Pro Val Ile Asn Gly Thr
        260                 265                 270

Ser Pro Val Leu Gln Tyr Glu Ile Glu Thr Asp Pro Ala Leu Thr Tyr
        275                 280                 285

Val Glu Gly Val Cys Val Val Trp Phe Thr Phe Glu Phe Leu Val Arg
    290                 295                 300

Ile Val Phe Ser Pro Asn Lys Leu Glu Phe Ile Lys Asn Leu Leu Asn
305                 310                 315                 320

Ile Ile Asp Phe Val Ala Ile Leu Pro Phe Tyr Leu Glu Val Gly Leu
            325                 330                 335

Ser Gly Leu Ser Ser Lys Ala Ala Lys Asp Val Leu Gly Phe Leu Arg
        340                 345                 350

Val Val Arg Phe Val Arg Ile Leu Arg Ile Phe Lys Leu Thr Arg His
    355                 360                 365

Phe Val Gly Leu Arg Val Leu Gly His Thr Leu Arg Ala Ser Thr Asn
    370                 375                 380

Glu Phe Leu Leu Leu Ile Ile Phe Leu Ala Leu Gly Val Leu Ile Phe
385                 390                 395                 400

Ala Thr Met Ile Tyr Tyr Ala Glu Arg Val Gly Ala Gln Pro Asn Asp
                405                 410                 415

Pro Ser Ala Ser Glu His Thr Gln Phe Lys Asn Ile Pro Ile Gly Phe
            420                 425                 430

Trp Trp Ala Val Val Thr Met Thr Thr Leu Gly Tyr Gly Asp Met Tyr
    435                 440                 445

Pro Gln Thr Trp Ser Gly Met Leu Val Gly Ala Leu Cys Ala Leu Ala
    450                 455                 460

Gly Val Leu Thr Ile Ala Met Pro Val Pro Val Ile Val Asn Asn Phe
465                 470                 475                 480

Gly Met Tyr Tyr Ser Leu Ala Met Ala Lys Gln Lys Leu Pro Arg Lys
                485                 490                 495

Arg Lys Lys His Ile Pro Pro Ala Pro Leu Ala Ser Ser Pro Thr Phe
            500                 505                 510

-continued

```
Cys Lys Thr Glu Leu Asn Met Ala Cys Asn Ser Thr Gln Ser Asp Thr
        515                 520                 525
Cys Leu Gly Lys Glu Asn Arg Leu Leu Glu His Asn Arg Ser Val Leu
530                 535                 540
Ser Gly Asp Asp Ser Thr Gly Ser Glu Pro Pro Leu Ser Pro Pro Glu
545                 550                 555                 560
Arg Leu Pro Ile Arg Arg Ser Ser Thr Arg Asp Lys Asn Arg Arg Gly
                565                 570                 575
Glu Thr Cys Phe Leu Leu Thr Thr Gly Asp Tyr Thr Cys Ala Ser Asp
            580                 585                 590
Gly Gly Ile Arg Lys Ala Ser Thr Leu Glu Pro Met Glu Ser Thr Ala
        595                 600                 605
Gln Thr Lys Gly Asp Thr Arg Pro Glu Ala His Trp Asn Cys Ala His
    610                 615                 620
Leu Leu Asn Phe Gly Cys Pro Thr Gly Ser Ser Phe Pro Thr Leu
625                 630                 635

<210> SEQ ID NO 43
<211> LENGTH: 757
<212> TYPE: PRT
<213> ORGANISM: Unknown
<220> FEATURE:
<223> OTHER INFORMATION: Description of Unknown:
      Kv3.3 sequence

<400> SEQUENCE: 43

Met Leu Ser Ser Val Cys Val Ser Ser Phe Arg Gly Arg Gln Gly Ala
1               5                   10                  15
Ser Lys Gln Gln Pro Ala Pro Pro Gln Pro Pro Glu Ser Pro Pro
            20                  25                  30
Pro Pro Pro Leu Pro Pro Gln Gln Gln Pro Ala Gln Pro Gly Pro
        35                  40                  45
Ala Ala Ser Pro Ala Gly Pro Pro Ala Pro Arg Gly Pro Gly Asp Arg
    50                  55                  60
Arg Ala Glu Pro Cys Pro Gly Leu Pro Ala Ala Ala Met Gly Arg His
65                  70                  75                  80
Gly Gly Gly Gly Gly Asp Ser Gly Lys Ile Val Ile Asn Val Gly Gly
                85                  90                  95
Val Arg His Glu Thr Tyr Arg Ser Thr Leu Arg Thr Leu Pro Gly Thr
            100                 105                 110
Arg Leu Ala Gly Leu Thr Glu Pro Glu Ala Ala Ala Arg Phe Asp Tyr
        115                 120                 125
Asp Pro Gly Ala Asp Glu Phe Phe Phe Asp Arg His Pro Gly Val Phe
    130                 135                 140
Ala Tyr Val Leu Asn Tyr Tyr Arg Thr Gly Lys Leu His Cys Pro Ala
145                 150                 155                 160
Asp Val Cys Gly Pro Leu Phe Glu Glu Glu Leu Gly Phe Trp Gly Ile
                165                 170                 175
Asp Glu Thr Asp Val Glu Ala Cys Cys Trp Met Thr Tyr Arg Gln His
            180                 185                 190
Arg Asp Ala Glu Glu Ala Leu Asp Ser Phe Glu Ala Pro Asp Pro Ala
        195                 200                 205
Gly Ala Ala Asn Ala Ala Asn Ala Ala Gly Ala His Asp Gly Gly Leu
    210                 215                 220
Asp Asp Glu Ala Gly Ala Gly Gly Gly Leu Asp Gly Ala Gly Gly
225                 230                 235                 240
```

-continued

```
Glu Leu Lys Arg Leu Cys Phe Gln Asp Ala Gly Gly Ala Gly Gly
                245                 250                 255

Pro Pro Gly Gly Ala Gly Ala Gly Gly Thr Trp Trp Arg Arg Trp
            260                 265                 270

Gln Pro Arg Val Trp Ala Leu Phe Glu Asp Pro Tyr Ser Ser Arg Ala
        275                 280                 285

Ala Arg Tyr Val Ala Phe Ala Ser Leu Phe Phe Ile Leu Ile Ser Ile
    290                 295                 300

Thr Thr Phe Cys Leu Glu Thr His Glu Gly Phe Ile His Ile Ser Asn
305                 310                 315                 320

Lys Thr Val Thr Gln Ala Ser Pro Ile Pro Gly Ala Pro Pro Glu Asn
                325                 330                 335

Ile Thr Asn Val Glu Val Glu Thr Glu Pro Phe Leu Thr Tyr Val Glu
            340                 345                 350

Gly Val Cys Val Val Trp Phe Thr Phe Glu Phe Leu Met Arg Ile Thr
        355                 360                 365

Phe Cys Pro Asp Lys Val Glu Phe Leu Lys Ser Ser Leu Asn Ile Ile
    370                 375                 380

Asp Cys Val Ala Ile Leu Pro Phe Tyr Leu Glu Val Gly Leu Ser Gly
385                 390                 395                 400

Leu Ser Ser Lys Ala Ala Lys Asp Val Leu Gly Phe Leu Arg Val Val
                405                 410                 415

Arg Phe Val Arg Ile Leu Arg Ile Phe Lys Leu Thr Arg His Phe Val
            420                 425                 430

Gly Leu Arg Val Leu Gly His Thr Leu Arg Ala Ser Thr Asn Glu Phe
        435                 440                 445

Leu Leu Leu Ile Ile Phe Leu Ala Leu Gly Val Leu Ile Phe Ala Thr
    450                 455                 460

Met Ile Tyr Tyr Ala Glu Arg Ile Gly Ala Asp Pro Asp Asp Ile Leu
465                 470                 475                 480

Gly Ser Asn His Thr Tyr Phe Lys Asn Ile Pro Ile Gly Phe Trp Trp
                485                 490                 495

Ala Val Val Thr Met Thr Thr Leu Gly Tyr Gly Asp Met Tyr Pro Lys
            500                 505                 510

Thr Trp Ser Gly Met Leu Val Gly Ala Leu Cys Ala Leu Ala Gly Val
        515                 520                 525

Leu Thr Ile Ala Met Pro Val Pro Val Ile Val Asn Asn Phe Gly Met
    530                 535                 540

Tyr Tyr Ser Leu Ala Met Ala Lys Gln Lys Leu Pro Lys Lys Lys Asn
545                 550                 555                 560

Lys His Ile Pro Arg Pro Pro Gln Pro Gly Ser Pro Asn Tyr Cys Lys
                565                 570                 575

Pro Asp Pro Pro Pro Pro Pro Pro His Pro His His Gly Ser Gly
            580                 585                 590

Gly Ile Ser Pro Pro Pro Ile Thr Pro Ser Met Gly Val Thr
        595                 600                 605

Val Ala Gly Ala Tyr Pro Ala Gly Pro His Thr His Pro Gly Leu Leu
    610                 615                 620

Arg Gly Gly Ala Gly Leu Gly Ile Met Gly Leu Pro Leu Pro
625                 630                 635                 640

Ala Pro Gly Glu Pro Cys Pro Leu Ala Gln Glu Glu Val Ile Glu Ile
                645                 650                 655
```

-continued

```
Asn Arg Ala Asp Pro Arg Pro Asn Gly Asp Pro Ala Ala Ala Ala Leu
            660             665                 670

Ala His Glu Asp Cys Pro Ala Ile Asp Gln Pro Ala Met Ser Pro Glu
        675                 680              685

Asp Lys Ser Pro Ile Thr Pro Gly Ser Arg Gly Arg Tyr Ser Arg Asp
    690                 695             700

Arg Ala Cys Phe Leu Leu Thr Asp Tyr Ala Pro Ser Pro Asp Gly Ser
705                 710                 715                 720

Ile Arg Lys Ala Thr Gly Ala Pro Pro Leu Pro Pro Gln Asp Trp Arg
                725             730                 735

Lys Pro Gly Pro Pro Ser Phe Leu Pro Asp Leu Asn Ala Asn Ala Ala
            740             745                 750

Ala Trp Ile Ser Pro
        755
```